(12) United States Patent
Kono et al.

(10) Patent No.: US 9,129,412 B2
(45) Date of Patent: Sep. 8, 2015

(54) IMAGE PROCESSING APPARATUS, IMAGE PROCESSING METHOD, AND COMPUTER-READABLE RECORDING DEVICE

(71) Applicant: OLYMPUS CORPORATION, Tokyo (JP)

(72) Inventors: Takashi Kono, Tachikawa (JP); Yamato Kanda, Hino (JP); Makoto Kitamura, Hachioji (JP); Masashi Hirota, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/288,733

(22) Filed: May 28, 2014

(65) Prior Publication Data
US 2014/0270499 A1 Sep. 18, 2014

Related U.S. Application Data

(63) Continuation of application No. PCT/JP2012/081989, filed on Dec. 10, 2012.

(30) Foreign Application Priority Data

Dec. 8, 2011 (JP) ................................. 2011-269055

(51) Int. Cl.
*G06K 9/00* (2006.01)
*G06T 7/40* (2006.01)
*A61B 1/00* (2006.01)
*A61B 1/04* (2006.01)
*G06T 7/00* (2006.01)

(52) U.S. Cl.
CPC . *G06T 7/408* (2013.01); *A61B 1/00* (2013.01); *A61B 1/00009* (2013.01); *A61B 1/04* (2013.01);

(Continued)

(58) Field of Classification Search
CPC ..... G06K 9/00; G06K 9/4604; G06K 9/4652; G06K 2209/053; G06T 7/0012; G06T 7/0081; G06T 7/0083; G06T 7/0087; G06T 7/408; G06T 2207/10024; G06T 2207/10068; G06T 2207/20036; G06T 2207/20076; G06T 2207/20141; G06T 2207/20224; G06T 2207/30028; G06T 2207/30092; A61B 1/00; A61B 1/00009; A61B 1/0002; A61B 1/04; A61B 1/041; G02B 23/2484
See application file for complete search history.

(56) References Cited

U.S. PATENT DOCUMENTS

| | | | |
|---|---|---|---|
| 8,682,048 B2 * | 3/2014 | Hirota et al. | 382/128 |
| 8,837,821 B2 * | 9/2014 | Hirota et al. | 382/164 |

(Continued)

FOREIGN PATENT DOCUMENTS

| | | |
|---|---|---|
| JP | 2006-122502 A | 5/2006 |
| JP | 2007-175434 A | 7/2007 |

(Continued)

OTHER PUBLICATIONS

International Search Report dated Mar. 12, 2013 issued in PCT/JP2012/081989.

*Primary Examiner* — Jose Couso
(74) *Attorney, Agent, or Firm* — Scully, Scott, Murphy & Presser, PC

(57) ABSTRACT

An image processing apparatus includes: a color feature data calculation unit configured to calculate color feature data of each pixel in an intraluminal image or color feature data of each small region obtained by dividing the intraluminal image into a plurality of small regions; a residue candidate distribution determination unit configured to determine, from among the color feature data, color feature data distributed on a side comparatively strong in redness to be a mucosa distribution and determine color feature data distributed on a side comparatively weak in redness to be a residue candidate distribution; and a residue distribution determination unit configured to determine, from among distributions of the color feature data determined to be the residue candidate distribution, a residue candidate distribution distributed on a side strong in yellowness with reference to the mucosa distribution to be a residue distribution.

32 Claims, 39 Drawing Sheets

(52) U.S. Cl.
CPC ............... *A61B 1/041* (2013.01); *G06T 7/0081* (2013.01); *G06T 7/0087* (2013.01); *G06T 2207/10024* (2013.01); *G06T 2207/10068* (2013.01); *G06T 2207/20076* (2013.01); *G06T 2207/30028* (2013.01)

(56) References Cited

U.S. PATENT DOCUMENTS

| | | |
|---|---|---|
| 8,989,467 B2 * | 3/2015 | Hirota et al. .................. 382/130 |
| 2007/0165932 A1 | 7/2007 | Nishimura et al. |
| 2007/0191677 A1 | 8/2007 | Nishimura et al. |
| 2010/0119110 A1 | 5/2010 | Kanda |
| 2010/0124365 A1 | 5/2010 | Kanda |
| 2011/0311133 A1 | 12/2011 | Hirota et al. |
| 2014/0270377 A1 * | 9/2014 | Kanda et al. .................. 382/103 |

FOREIGN PATENT DOCUMENTS

| | | |
|---|---|---|
| JP | 2010-113616 A | 5/2010 |
| JP | 2010-115413 A | 5/2010 |
| JP | 2011-234931 A | 11/2011 |

* cited by examiner

IMAGE PROCESSING APPARATUS, IMAGE PROCESSING METHOD, AND COMPUTER-READABLE RECORDING DEVICE

CROSS-REFERENCE TO RELATED APPLICATIONS

This application is a continuation of PCT international application Ser. No. PCT/JP2012/031989 filed on Dec. 10, 2012 which designates the United States, incorporated herein by reference, and which claims the benefit of priority from Japanese Patent Application No. 2011-269055, filed on Dec. 8, 2011, incorporated herein by reference.

BACKGROUND OF THE INVENTION

1. Field of the Invention

The present invention relates to an image processing apparatus, an image processing method, and a computer-readable recording device for detecting, from an image, which is obtained by imaging inside of a subject's body, a region unnecessary for diagnosis.

2. Description of the Related Art

Conventionally, endoscopes have been widely spread as medical observation devices that are introduced inside subjects such as patients and observe noninvasively inside living bodies. In recent years, swallowing type endoscopes (capsule endoscopes) have been developed, which accommodate imaging devices, communication devices, and the like inside capsule-shaped casings and wirelessly transmit image data acquired by capturing images with the imaging devices to outside of bodies.

However, observation and diagnosis of the image (intraluminal image) captured by such a medical observation device inside a lumen of a living body require much experience. Therefore, medical diagnosis support functions for assisting the diagnosis by doctors are desired. As one of image recognition techniques realizing such a function, a technique has been proposed, which is for automatically detecting a region to be noted from an intraluminal image, and extracting and presenting the region to be noted, or on the contrary, excluding the region to be noted from a target to be diagnosed for presentation.

As a method of determining whether a region in an intraluminal image is a region to be noted or not, for example, a method is known, which uses, based on a plurality of images (teacher data) having coordinate information given beforehand on various regions (for example, a mucosa region and a lesion region), a color feature data space having components that are color feature data (for example, G/R values and B/G values) based on pixel values (R-value, G-value, and B-value) of each pixel. In this method, to the color feature data space, for example, a determination threshold value is set between a color feature data distribution of pixels belonging to the region to be noted and a color feature data distribution of pixels belonging to a region other than the region to be noted, and by threshold processing color feature data of each pixel of the intraluminal image to be determined with the determination threshold value, whether or not each pixel belongs to the region to be noted is determined.

However, a range in which various regions are distributed in a color feature data space may largely vary among intraluminal images and thus there is a problem that a detection accuracy in the above described method becomes low. Therefore, in Japanese Laid-open Patent Publication No. 2010-113616, in a color feature data space, by performing clustering on color feature data distribution of pixels of an intraluminal image (or small regions obtained by dividing the intraluminal image), comparing a representative value, such as a centroid, calculated from each cluster, with the above mentioned determination threshold value to determine whether or not each cluster belongs to each region, reduction in a detection accuracy caused by variation in distributions among images is suppressed.

SUMMARY OF THE INVENTION

In some embodiments, an image processing apparatus for distinguishing, from an intraluminal image obtained by imaging inside of a lumen of a subject, a residue region where a residue is photographed, is presented. The image processing apparatus includes: a color feature data calculation unit configured to calculate color feature data of each pixel in the intraluminal image or color feature data of each small region obtained by dividing the intraluminal image into a plurality of small regions; a residue candidate distribution determination unit configured to determine, from among the color feature data, color feature data distributed on a side comparatively strong in redness to be a mucosa distribution and determine color feature data distributed on a side comparatively weak in redness to be a residue candidate distribution; and a residue distribution determination unit configured to determine, from among distributions of the color feature data determined to be the residue candidate distribution, a residue candidate distribution distributed on a side strong in yellowness with reference to the mucosa distribution to be a residue distribution.

In some embodiments, an image processing method of distinguishing, from an intraluminal image obtained by imaging inside of a lumen of a subject, a residue region where a residue is photographed, is presented. The image processing method includes: calculating color feature data of each pixel in the intraluminal image or color feature data of each small region obtained by dividing the intraluminal image into a plurality of small regions; determining, from among the color feature data, color feature data distributed on a side comparatively strong in redness to be a mucosa distribution and determining color feature data distributed on a side comparatively weak in redness to be a residue candidate distribution; and determining, from the residue candidate distribution, a residue candidate distribution distributed on a side strong in yellowness with reference to the mucosa distribution to be a residue distribution.

In some embodiments, a computer-readable recording device with an executable program stored thereon is presented. The program instructs a processor for distinguishing, from an intraluminal image obtained by imaging inside of a lumen of a subject, a residue region where a residue is photographed, to execute: calculating color feature data of each pixel in the intraluminal image or color feature data of each small region obtained by dividing the intraluminal image into a plurality of small regions; determining, from among the color feature data, color feature data distributed on a side comparatively strong in redness to be a mucosa distribution and determining color feature data distributed on a side comparatively weak in redness to be a residue candidate distribution; and determining, from the residue candidate distribution, a residue candidate distribution distributed on a side strong in yellowness with reference to the mucosa distribution to be a residue distribution.

In some embodiments, an image processing apparatus for distinguishing, from an intraluminal image obtained by imaging inside of a lumen of a subject, a residue region where a residue is photographed, is presented. The image processing apparatus includes: a color feature data calculation unit configured to calculate color feature data of each pixel in the intraluminal image or color feature data of each small region obtained by dividing the intraluminal image into a plurality of small regions; a residue candidate distribution determination unit configured to assign, on a first determination axis of color feature data for determining redness, one or more distribution models to a distribution of the color feature data, and determine, based on redness of the one or more distribution models, color feature data representing a residue candidate; and a residue distribution determination unit configured to assign, on a second determination axis of color feature data for determining yellowness, one or more distribution models to the color feature data determined to represent the residue candidate by the residue candidate distribution determination unit and determine, based on yellowness of the one or more distribution models, color feature data representing a residue.

In some embodiments, an image processing method of distinguishing, from an intraluminal image obtained by imaging inside of a lumen of a subject, a residue region where a residue is photographed, is presented. The image processing method includes: calculating color feature data of each pixel in the intraluminal image or color feature data of each small region obtained by dividing the intraluminal image into a plurality of small regions; assigning, on a first determination axis of color feature data for determining redness, one or more distribution models to a distribution of the color feature data and determining, based on redness of the one or more distribution models, color feature data representing a residue candidate; and assigning, on a second determination axis of color feature data for determining yellowness, one or more distribution models to the color feature data determined to represent the residue candidate, and determining, based on yellowness of the one or more distribution models, color feature data representing a residue.

In some embodiments, a computer-readable recording device with an executable program stored thereon is presented. The program instructs a processor for distinguishing, from an intraluminal image obtained by imaging inside of a lumen of a subject, a residue region where a residue is photographed, to execute: calculating color feature data of each pixel in the intraluminal image or color feature data of each small region obtained by dividing the intraluminal image into a plurality of small regions; assigning, on a first determination axis of color feature data for determining redness, one or more distribution models to a distribution of the color feature data and determining, based on redness of the one or more distribution models, color feature data representing a residue candidate; and assigning, on a second determination axis of color feature data for determining yellowness, one or more distribution models to the color feature data determined to represent the residue candidate, and determining, based on yellowness of the one or more distribution models, color feature data representing a residue.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, an image processing apparatus, an image processing method, and an image processing program according to embodiments of the present invention will be described with reference to the drawings. The present invention is not limited by these embodiments. Further, in describing the drawings, the same portions are appended with the same reference signs.

In the following embodiments, as an example, description will be made on image processing of distinguishing a residue region from an intraluminal image (hereinafter, also referred to as "image") acquired by imaging inside of a lumen of a subject with a medical observation device such as an endoscope. In the following embodiments, the intraluminal image to be a target of the image processing is a color image having pixel levels (pixel values) for respective red (R), green (G), and blue (B) color-components (wavelength components) at each pixel position.

First Embodiment

Figure 1:
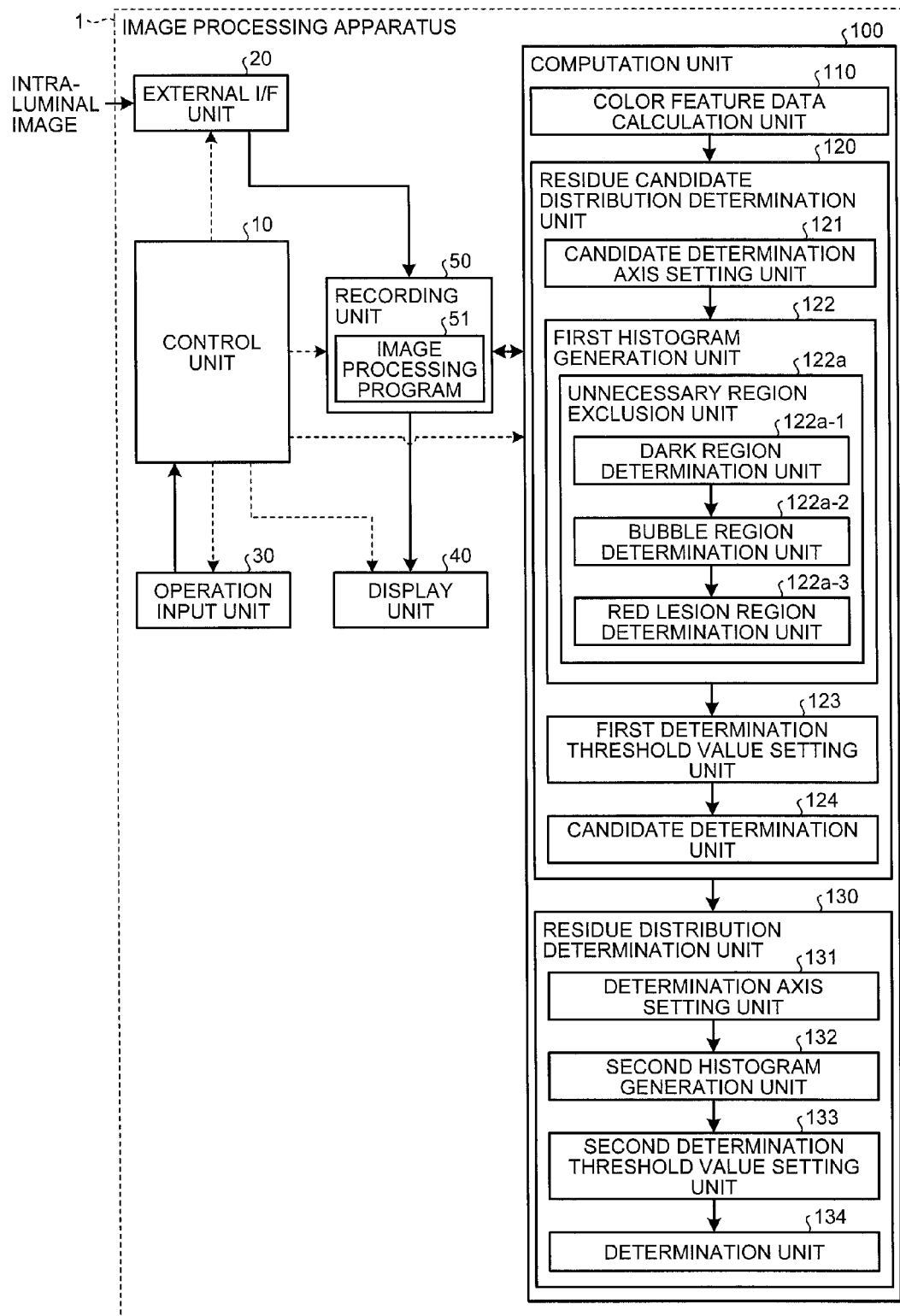
FIG. 1 is a block diagram illustrating a configuration of an image processing apparatus according to a first embodiment of the present invention.

FIG. 1 is a block diagram illustrating a configuration of an image processing apparatus according to a first embodiment of the present invention. In FIG. 1, a line that transmits data of an image signal or the like is indicated by a solid line, and a line that transmits a control signal is indicated by a broken line.

As illustrated in FIG. 1, an image processing apparatus 1 according to the first embodiment includes: a control unit 10 that controls operations of the whole image processing apparatus 1; an external interface (I/F) unit 20 that serves as an image acquiring unit that acquires image data corresponding to an image captured by a medical observation device such as a capsule endoscope; an operation input unit 30 that generates an input signal by an operation from outside; a display unit 40 that displays various information; a recording unit 50 that records therein various programs and the image data acquired via the external interface unit 20; and a computation unit 100 that executes specified image processing with respect to the image data.

The control unit 10 is realized by hardware such as a CPU, and by reading the various programs recorded in the recording unit 50, performs transfer or the like of instructions and data to respective units included in the image processing apparatus 1 according to the image data input from the external interface unit 20 or an operation signal or the like input from the operation input unit 30 and comprehensively controls the operations of the whole image processing apparatus 1.

The external interface unit 20 is the image acquiring unit that takes the image data into the image processing apparatus from an external device or a recording medium. To the external interface unit 20, various external devices are connected, depending on modes of a system including the medical observation device. For example, if the medical observation device is a capsule endoscope and a portable recording medium is used in receiving and sending the image data from and to the medical observation device, a reader device, in which this recording medium is detachably placed and which reads out the image data of the intraluminal image recorded in the recording medium, is connected to the external interface unit 20. Further, if a server to store the image data of the intraluminal image captured by the medical observation device is installed, a communication device or the like that performs data communications with the server is connected to the external interface unit 20 and by the data communications, the image data are fetched into the image processing apparatus 1. Or, the medical observation device such as an endoscope may be connected to the external interface unit 20 via a cable and an image signal may be directly fetched into the image processing apparatus 1 from the medical observation device.

The operation input unit 30 is realized by an input device such as a keyboard, a mouse, a touch panel, or various switches, for example, and outputs, to the control unit 10, an input signal received.

The display unit 40 is realized by a display device, such as an LCD or an EL display, and under control of the control unit 10, displays various screens including the intraluminal image.

The recording unit 50 is realized by various IC memories including a ROM and a RAM, such as a rewritable flash memory, a hard disk that is built therein or connected via a data communication terminal, or an information recording medium such as a CD-ROM, and a reading device therefor or the like. The recording unit 50 records therein the image data of the intraluminal image acquired via the external interface unit 20, as well as a program for causing the image processing apparatus 1 to operate and causing the image processing apparatus 1 to execute various functions and data or the like to be used during the execution of this program. Specifically, the recording unit 50 records therein an image processing program 51 for causing the image processing apparatus 1 to execute image processing of distinguishing a residue region from the intraluminal image and a determination threshold value or the like used during the execution of the image processing program.

The computation unit 100 is realized by hardware such as a CPU, performs the image processing on the image data corresponding to the intraluminal image by reading the image processing program 51, and performs various computation processes for distinguishing the residue region from the intraluminal image.

Next, a detailed configuration of the computation unit 100 is described.

The computation unit 100 includes: a color feature data calculation unit 110 that calculates color feature data of each pixel in the intraluminal image and generates a distribution; a residue candidate distribution determination unit 120 that determines color feature data distributed on a side comparatively strong in redness to be a mucosa distribution, and determines color data distributed on a side comparatively weak in redness to be a residue candidate distribution, from among the distribution of the color feature data; and a residue distribution determination unit 130 that determines, from among the residue candidate distribution, a residue candidate distribution distributed on a side having strong yellowness with reference to the mucosa distribution to be a residue distribution.

Of these, the residue candidate distribution determination unit 120 includes a candidate determination axis setting unit 121 that sets a determination axis, which distinguishes between the mucosa distribution and the residue candidate distribution and determines whether or not each distribution is a residue candidate distribution, as a candidate determination axis; a first histogram generation unit 122 that generates, with respect to the candidate determination axis, a histogram representing a frequency distribution of the color feature data that respective pixels have; a first determination threshold value setting unit 123 that sets on the candidate determination axis a determination threshold value (hereinafter, also referred to as "candidate determination threshold value") for extracting a range of color feature data corresponding to a mucosa region; and a candidate determination unit 124 that determines, based on this determination threshold value, the mucosa distribution and the residue candidate distribution.

Of these, the candidate determination axis setting unit 121 sets an axis corresponding to color feature data that at least change in strength of redness, as the candidate determination axis.

Further, the first histogram generation unit 122 includes an unnecessary region exclusion unit 122a that detects at least one of a bubble region, a dark region, and a red lesion region from the intraluminal image, determines it to be a region unnecessary for distinction of the residue region, and excludes it. In more detail, the unnecessary region exclusion unit 122a includes a dark region determination unit 122a-1, a bubble region determination unit 122a-2, and a red lesion region determination unit 122a-3.

The first determination threshold value setting unit 123 sets, based on the histogram generated by the first histogram generation unit 122, the candidate determination threshold value. In more detail, the first determination threshold value setting unit 123 evaluates a bimodal shape of the histogram, approximates, based on a result of this evaluation, the histogram by one normal distribution or two normal distributions, and sets, based on a relation or relations between the approximated normal distribution/distributions and the mucosa distribution and residue distribution, the candidate determination threshold value. Or, if the histogram is evaluated to have no bimodality, the first determination threshold value setting unit 123 may not approximate the histogram by a normal distribution and may set the candidate determination threshold value based on the histogram itself.

The residue distribution determination unit 130 includes a determination axis setting unit 131 that sets a determination axis used in determining whether or not the residue candidate distribution corresponds to a residue distribution; a second histogram generation unit 132 that generates a histogram representing a frequency distribution of color feature data included in the residue candidate distribution with respect to the determination axis; a second determination threshold value setting unit 133 that sets, on the determination axis, a determination threshold value for determining whether or not the residue candidate distribution corresponds to a residue distribution; and a determination unit 134 that determines the residue candidate distribution present on a side stronger in yellowness than the determination threshold value to be a residue distribution.

Of these, the determination axis setting unit 131 sets an axis corresponding to color feature data that change in strength of yellowness as the determination axis.

Further, the second determination threshold value setting unit 133 sets, based on the histogram generated by the second histogram generation unit 132, the determination threshold value. In more detail, the second determination threshold value setting unit 133 evaluates a bimodal shape of the histogram, approximates, based on a result of this evaluation, the histogram by one normal distribution or two normal distributions, and sets, based on a relation between the approximated normal distribution/distributions and the mucosa distribution, the determination threshold value. Or, if the histogram is evaluated to have no bimodality, the second determination threshold value setting unit 133 may not approximate the histogram by a normal distribution and may set the determination threshold value based on the histogram itself.

Figure 2:
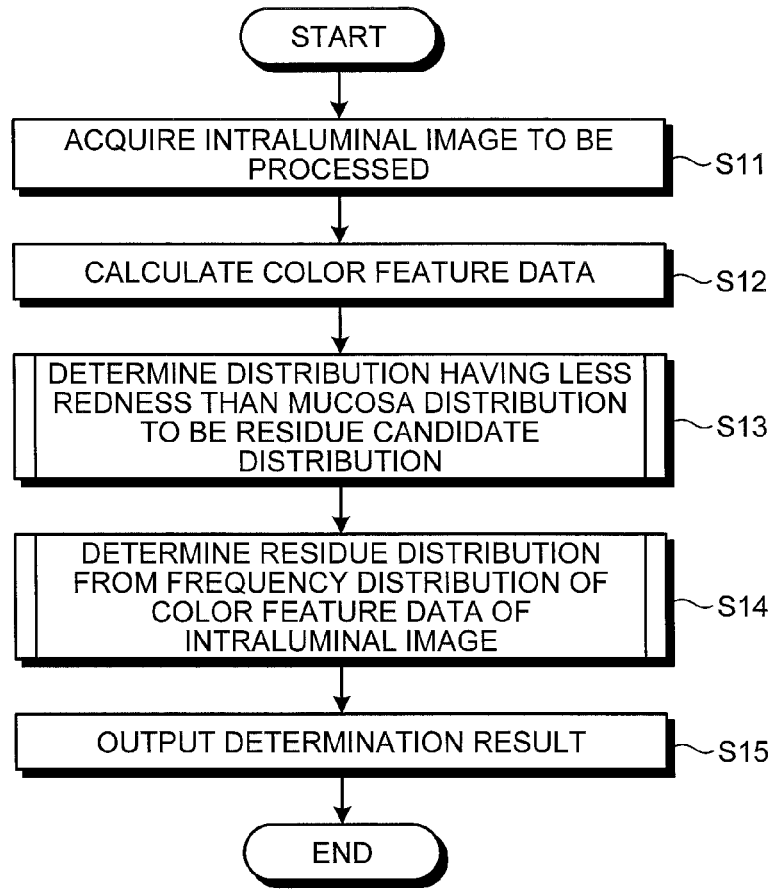
FIG. 2 is a flow chart illustrating operations of the image processing apparatus illustrated in FIG. 1.
Figure 3:
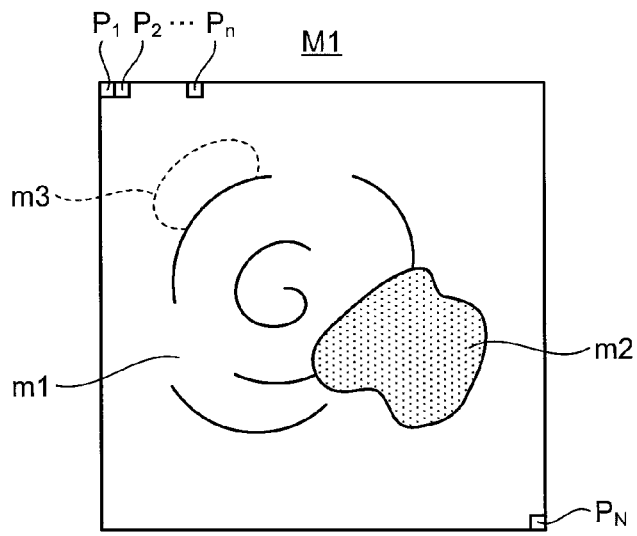
FIG. 3 is a schematic diagram illustrating an example of an intraluminal image to be processed by the image processing apparatus illustrated in FIG. 1.

Next, operations of the image processing apparatus 1 are described. FIG. 2 is a flow chart illustrating the operations of the image processing apparatus 1. Further, FIG. 3 is a schematic diagram illustrating an example of the intraluminal image to be processed by the image processing apparatus 1. In an image M1 exemplified in FIG. 3, a mucosa region m1 in the lumen, a residue region m2 captured on the front side of this mucosa region m1, and a white lesion region m3 where a part of the mucosa is whitened, are displayed.

First, at step S11, the image processing apparatus 1 acquires an intraluminal image of a subject via the external interface unit 20 and records it in the recording unit 50. The computation unit 100 reads images to be processed (for example, the image M1 illustrated in FIG. 3) from the recording unit 50 in sequence.

Subsequently, at step S12, the color feature data calculation unit 110 calculates color feature data from pixel values (R-component, G-component, and B-component) of each pixel in the intraluminal image. In the first embodiment, as a first color feature data, a G/R value, which is a ratio of the G-component to the R-component, and as a second color feature data, a B/G value, which is a ratio of the B-component to the G-component, are calculated.

Figure 4:
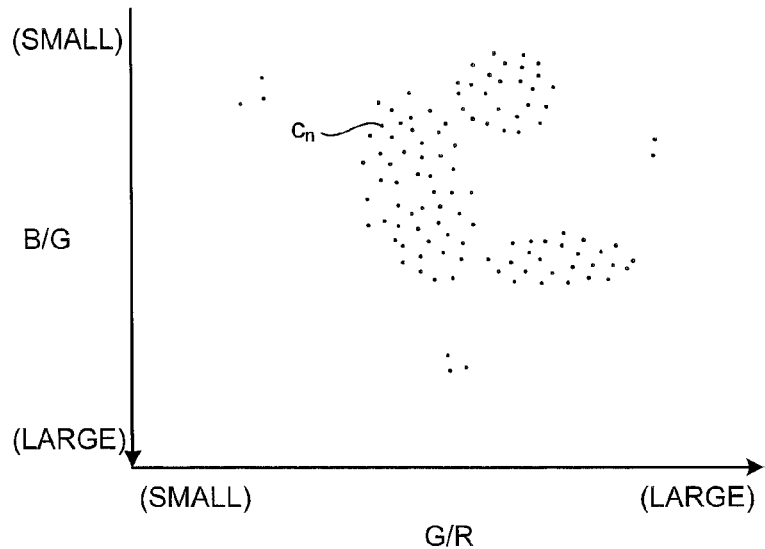
FIG. 4 is a diagram illustrating a distribution of color feature data plotted in a color feature data space.

At step S13, the residue candidate distribution determination unit 120 determines, from among a distribution of color feature data of the intraluminal image as illustrated in FIG. 4, for example, a distribution having a weaker redness than a mucosa distribution to be a residue candidate distribution.

Figure 5:
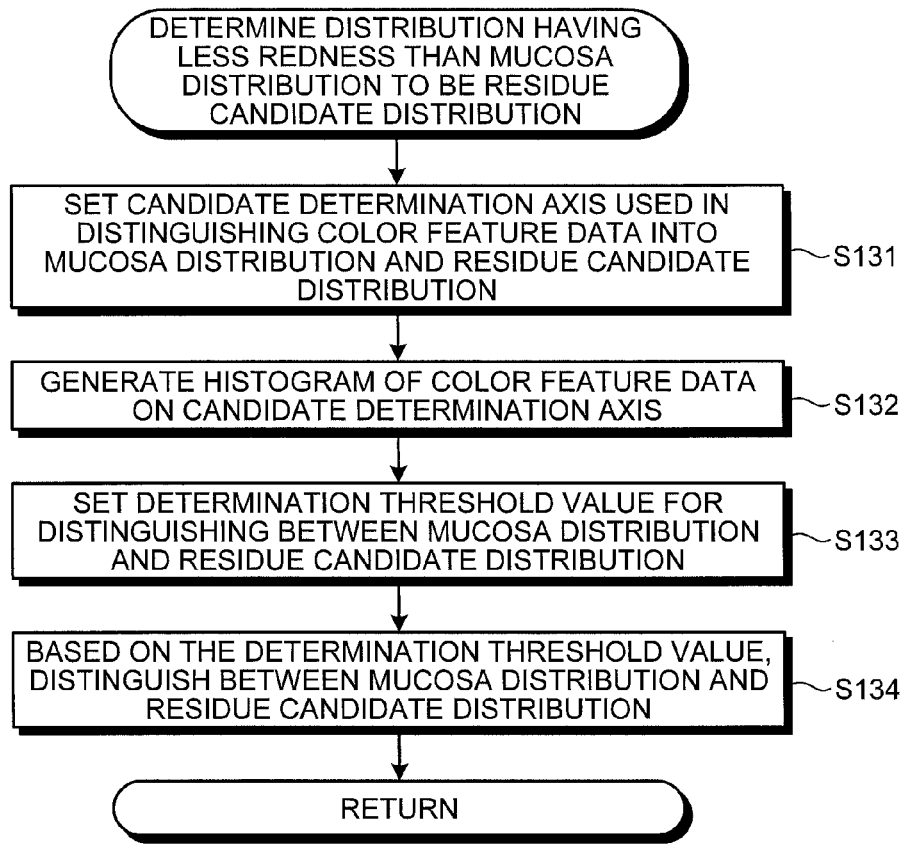
FIG. 5 is a flow chart illustrating operations of a residue candidate distribution determination unit illustrated in FIG. 1.

FIG. 5 is a flow chart illustrating detailed operations of the candidate distribution determination unit.

At step S131, the candidate determination axis setting unit 121 sets, as a candidate determination axis used in distinguishing the color feature data into the mucosa distribution and the residue candidate distribution, an axis corresponding to the G/R value (G/R axis). In an intraluminal image acquired with its respective R, G, and B-components being stable without being saturated in luminance among pixel levels between 0 to 255, variation of the mucosa distribution is sufficiently small in the G/R value. Therefore, setting the candidate determination axis correspondingly with the G/R value, allows, at later stage threshold processing, separation between the mucosa region and the residue candidate distribution, which is the distribution of color feature data weak in redness with respect to the mucosa region, to be easy.

At step S132, the first histogram generation unit 122 generates, with respect to the candidate determination axis, a histogram that represents a frequency distribution of the color feature data of each pixel of the intraluminal image.

In order to do so, first, the unnecessary region exclusion unit 122a excludes a region unnecessary in distinguishing between the mucosa distribution and the residue candidate distribution. Examples of the unnecessary region include, for example, a dark region where observation of the subject is difficult, a bubble region where a digestive fluid has become a bubble in the lumen, and a red lesion region that is definitely not a residue.

In more detail, the dark region determination unit 122a-1 determines a region of pixels each having a luminance value "Y" (reference: Computer Graphic Arts Society, "Digital Image Processing", page 299) or a specified pixel value (for example, an "R" value) that is less than a specified threshold value to be the dark region. The "R" value is used because an "R" color-component has the least absorption in the intraluminal image and mostly reflected at a surface of the subject, and thus reflects structural information of the mucosa most well.

Further, the bubble region determination unit 122a-2 determines a region of pixels each having a frequency component of the luminance value "Y" that is higher than a specified threshold value and a chroma (Reference: Computer Graphics Arts Society, "Digital Image Processing", page 64) that is less than a specified threshold value to be the bubble region. The frequency component is able to be found by calculating a coefficient obtained after performing DCT conversion (discrete cosine transform) on the intraluminal image, or a difference value between the original intraluminal image and its average image. Further, the determination based on the chroma is possible by performing threshold processing on color ratio information (G/R value and B/G value).

Further, the red lesion region determination unit 122a-3 performs clustering of the frequency distribution of color feature data in the color feature data space by performing watershed processing or the like for each mountain of the frequency distribution, extracts a distribution (cluster) not in a main distribution having a high frequency (for example, a largest cluster), and determines, from the cluster not in the main distribution, a region of pixels corresponding to color feature data in a cluster having an absolute position or relative position positioned on a side stronger in redness than the main distribution, to be the red lesion region.

If these unnecessary regions are detected, the unnecessary region exclusion unit 122a generates a flagged image by adding flags (for example: "0" for other; "1" for the dark region, "2" for the bubble region, and "3" for the red lesion region) to pixels included in each unnecessary region.

Figure 6:
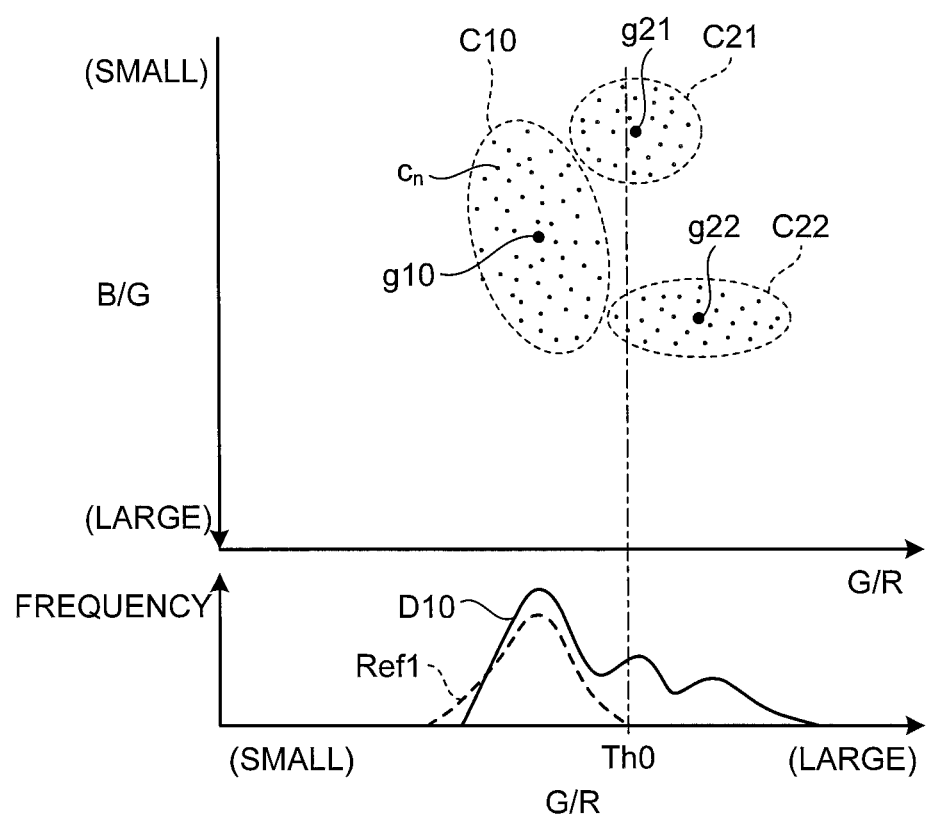
FIG. 6 is a diagram illustrating the distribution of the color feature data plotted in the color feature data space and a frequency distribution of the color feature data generated with respect to a candidate determination axis.

Based on this flagged image, the first histogram generation unit 122 excludes the unnecessary regions such as the dark region, the bubble region, and the red lesion region, and generates a histogram representing a frequency distribution of color feature data of pixels in a region remaining as result of the exclusion, with respect to the candidate determination axis. The first histogram generation unit 122 further excludes, from the generated histogram, a distribution having a frequency equal to or less than a specified value as a noise. Or, after normalizing the histogram such that a sum (integrated value) of the histogram is "1", a distribution having a proportion equal to or less than a specified value may be excluded as a noise. A distribution D10 illustrated in FIG. 6 illustrates a frequency distribution of color feature data in an intraluminal image after any unnecessary regions have been removed from the intraluminal image. The above described process of excluding the noise is not essential and may be omitted.

At step S133, the first determination threshold value setting unit 123 sets the determination threshold value (candidate determination threshold value) for distinguishing between the mucosa distribution and the residue candidate distribution. In more detail, if a representative value of each cluster used by the candidate determination unit 124 in the determination at later described step S134 is a minimum value, the first determination threshold value setting unit 123 generates a distribution of minimum values of each cluster of the mucosa distribution and the residue distribution according to the teacher data, and calculates and keeps, beforehand, a value around a boundary between both of these distributions as the candidate determination threshold value. Further, if the representative value of each cluster used by the candidate determination unit 124 in its determination is a centroid position, from a distribution of respective centroids of the mucosa distribution and residue distribution, a value around a boundary between both of these distributions is kept as the candidate determination threshold value.

At step S134, the candidate determination unit 124 distinguishes, based on the determination threshold value, between the mucosa distribution and the residue candidate distribution. In more detail, the candidate determination unit 124 performs clustering on the distribution of color feature data in the color feature data space, calculates a representative value (for example, a centroid position) of each cluster, compares this representative value with a candidate determination threshold value Th0, to thereby determine whether each cluster is a mucosa distribution or a residue candidate distribution. Specifically, as illustrated in FIG. 6, a cluster C10 having a centroid position g10 on a side stronger in redness than the candidate determination threshold value Th0 (on a side smaller in G/R value) is determined to be a mucosa distribution, and clusters C21 and C22 having centroid positions g21 and g22 that are on a side weaker in redness than the candidate determination threshold value Th0 (a side larger in G/R value) are determined to be residue candidate distributions. As a method of clustering, a known method is usable, such as watershed processing, a hierarchy process, a k-means method (Reference: Computer Graphic Arts Society, "Digital Image Processing", pages 231 to 232), an expectation maximization algorithm (EM algorithm), or self-organizing mapping. Further, as a representative value of a cluster, other than a centroid position, an average value, a mode value, a minimum value, or the like may be used. Further, although in FIG. 6, as the cluster corresponding to a mucosa distribution, only the cluster C10 is illustrated, a plurality of clusters corresponding to mucosa distributions may be generated.

Or, the candidate determination unit 124 may determine in which of a mucosa distribution and a residue candidate distribution each color feature data $c_n$ is included by comparing each color feature data $c_n$ with the candidate determination threshold value Th0.

Thereafter, the operations of the image processing apparatus 1 return to a main routine.

At step S14 subsequent to step S13, the residue distribution determination unit 130 receives information on the color feature data $c_n$ belonging respectively to the mucosa distribution and the residue candidate distribution from the residue candidate distribution determination unit 120 and distinguished the residue distribution. Specifically, a residue candidate distribution distributed on a side strong in yellowness with reference to a mucosa distribution is determined as a residue distribution.

Figure 7:
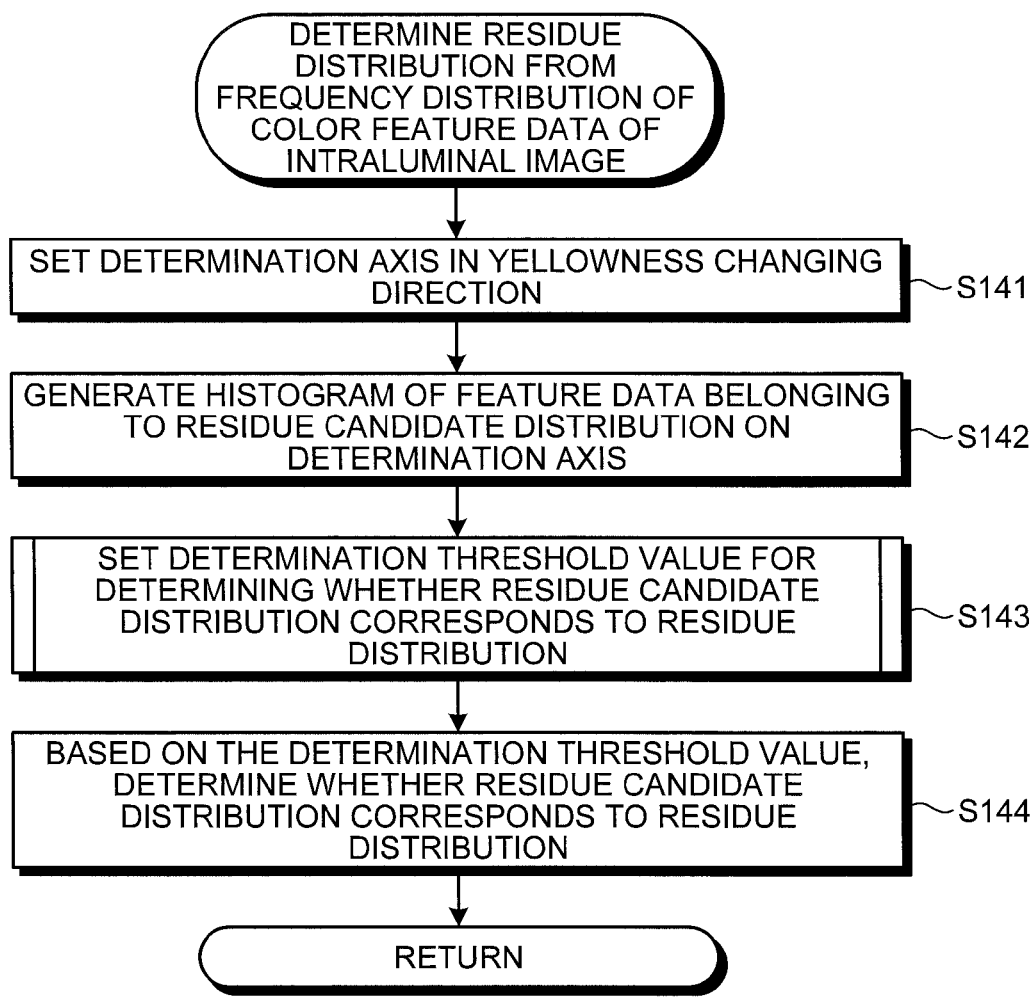
FIG. 7 is a flow chart illustrating operations of a distribution determination unit illustrated in FIG. 1.

FIG. 7 is a flow chart illustrating detailed operations of the residue distribution determination unit 130.

At step S141, the determination axis setting unit 131 sets an axis (B/G axis) corresponding to B/G values as a determination axis to be used in determining whether or not the residue candidate distribution corresponds to a residue distribution. The B/G value becomes smaller as the yellowness becomes stronger.

Figure 8:
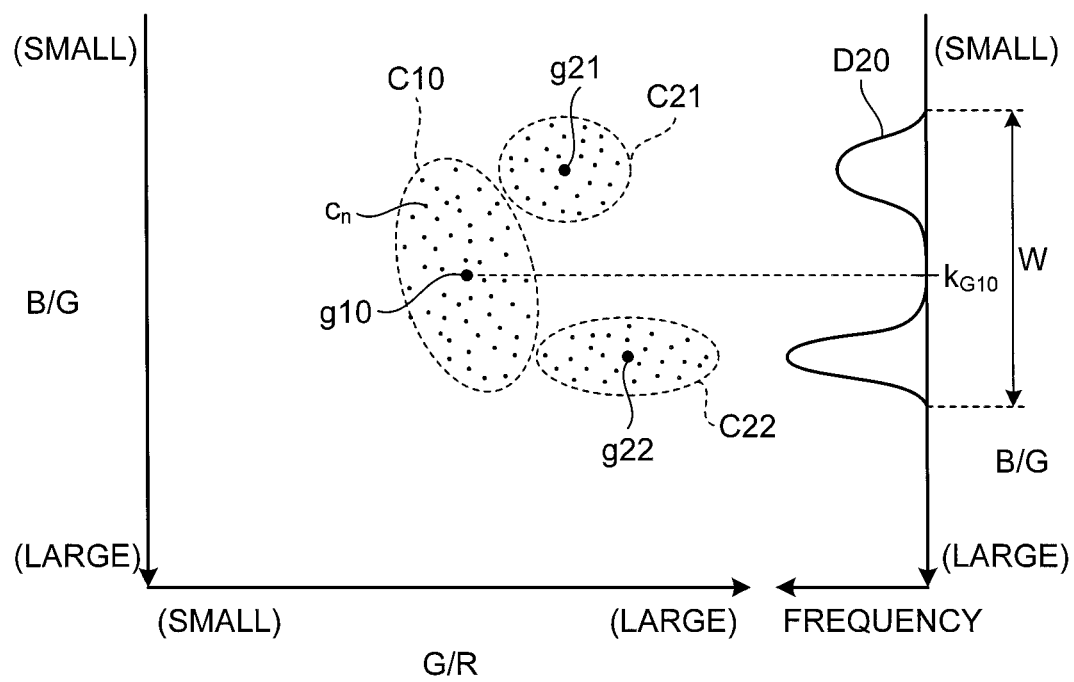
FIG. 8 is a diagram illustrating the color feature data plotted in the color feature data space and a frequency distribution of the color feature data generated with respect to a determination axis.

At step S142, the second histogram generation unit 132 generates, with respect to the determination axis, a histogram representing a frequency distribution of the color feature data $c_n$ belonging to the residue candidate distribution and further, excludes from the generated histogram, a distribution of a frequency equal to or less than a specified value, as a noise. Or, after normalizing the histogram such that a sum (integrated value) of the histogram becomes "1", a distribution having a proportion equal to or less than a specified value may be excluded as a noise. For example, a distribution D20 illustrated in FIG. 8 represents distributions of the color feature data $c_n$ included in the clusters C21 and C22 determined to be the residue candidate distributions. The above described process of excluding the noise is not essential and may be omitted.

At step S143, the second determination threshold value setting unit 133 sets a determination threshold value for determining whether or not the residue candidate distribution corresponds to a residue distribution.

Figure 9:
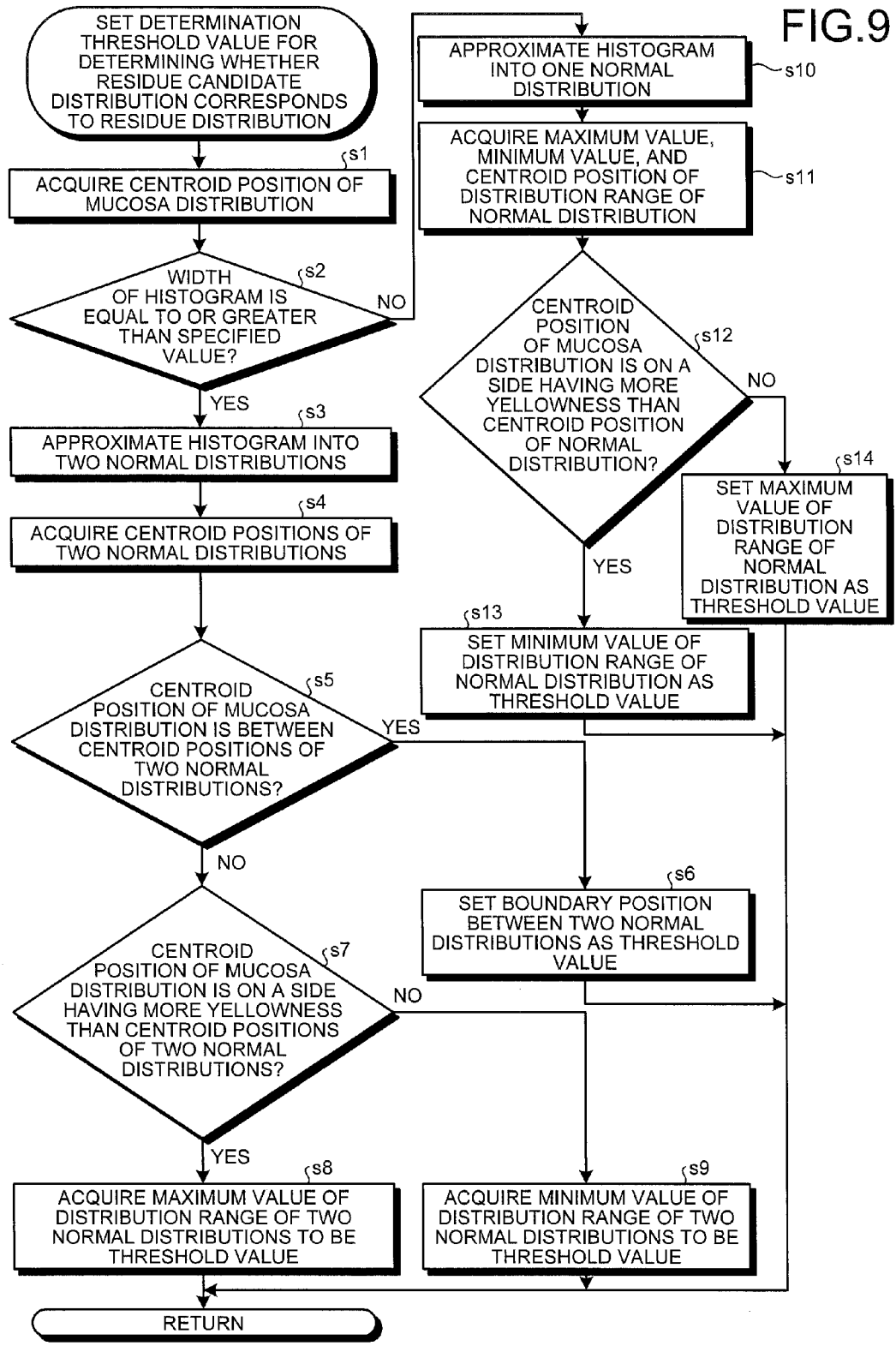
FIG. 9 is a flow chart illustrating operations of a second determination threshold value setting unit illustrated in FIG. 1.

FIG. 9 is a flow chart illustrating detailed operations of the second determination threshold value setting unit 133. Hereinafter, description is made while illustrating specific examples in FIG. 8 and FIG. 10 to FIG. 13. In the following description, a centroid position is used as the representative value of each distribution, but as the representative value, an average value, a mode value, or the like may be used instead.

First, at step s1, the second determination threshold value setting unit 133 obtains a centroid position $k_{G10}$, which is a projection on the determination axis (B/G axis) of the centroid g10 of the mucosa distribution (cluster C10).

Subsequently, at step s2, the second determination threshold value setting unit 133 determines whether or not a width "W" of the histogram (distribution D20) generated in step S142 is equal to or greater than a specified value.

If the width "W" is equal to or greater than the specified value (step s2: Yes), the second determination threshold value setting unit 133 approximates the distribution D20 by two normal distributions (step s3). As a method of approximating by two normal distributions, an expectation maximization algorithm (EM algorithm) may be used, for example.

Figure 10:
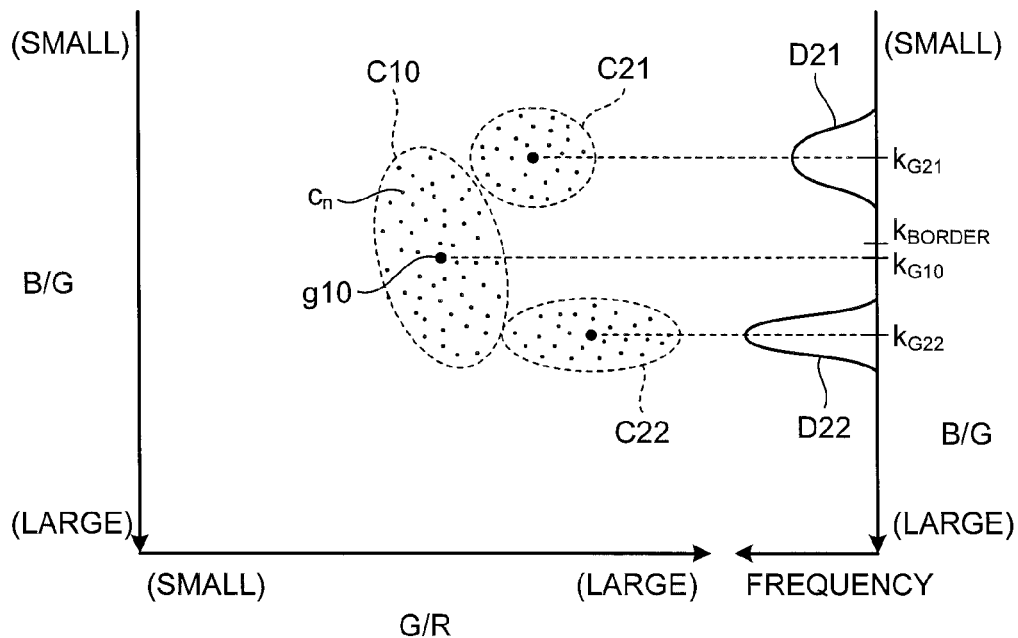
FIG. 10 is a diagram illustrating a method of setting a determination threshold value of a residue distribution.

Thereby, as illustrated in FIG. 10, a boundary position $k_{BORDER}$ in the distribution D20 and two normal distributions D21 and D22 are obtained.

Subsequently, at step s4, the second determination threshold value setting unit 133 obtains centroid positions $k_{G21}$ and $k_{G22}$ of the two normal distributions D21 and D22 respectively.

At step s5, the second determination threshold value setting unit 133 determines whether or not the centroid position $k_{G10}$ of the mucosa distribution is between the centroid positions $k_{G21}$ and $k_{G22}$ of the two normal distributions D21 and D22.

As illustrated in FIG. 10, if the centroid position $k_{G10}$ of the mucosa distribution is between the centroid positions $k_{G21}$ and $k_{G22}$ of the two normal distributions D21 and D22 (step s5: Yes), the second determination threshold value setting unit 133 sets the boundary position $k_{BORDER}$ as a determination threshold value (step s6).

On the contrary, if the centroid position $k_{G10}$ of the mucosa distribution is not between the centroid positions $k_{G21}$ and $k_{G22}$ of the two normal distributions D21 and D22 (step s5: No), subsequently, the second determination threshold value setting unit 133 determines whether or not the centroid position $k_{G10}$ of the mucosa distribution is on a side stronger in yellowness (a side smaller in B/G value) than the centroid positions $k_{G21}$ and $k_{G22}$ of the two normal distributions D21 and D22 (step s7).

Figure 11:
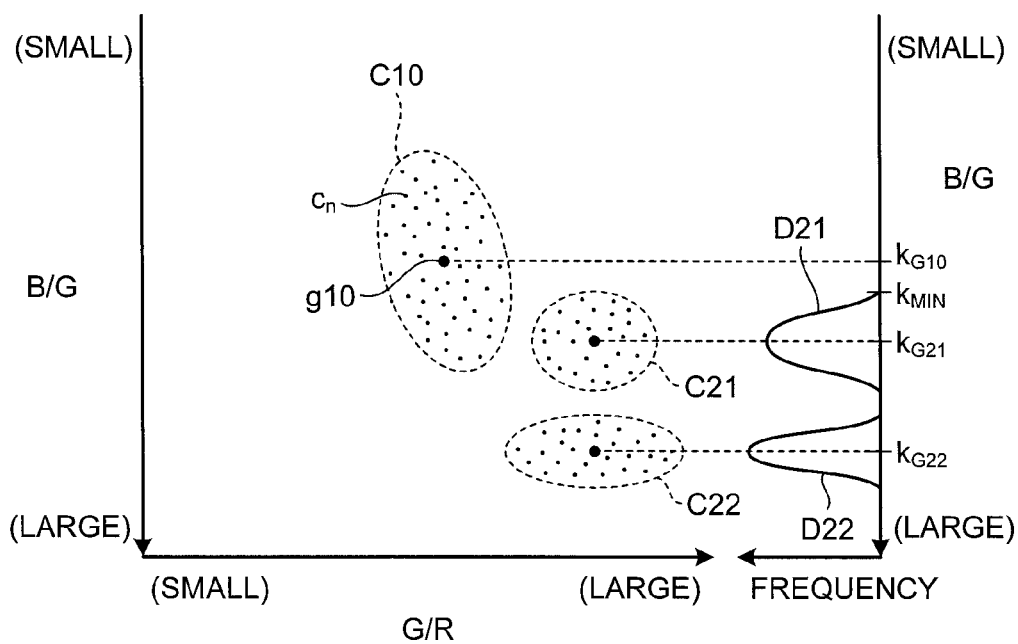
FIG. 11 is a diagram illustrating the method of setting the determination threshold value of the residue distribution.

As illustrated in FIG. 11, if the centroid position $k_{G10}$ of the mucosa distribution is on the side stronger in yellowness (the side smaller in B/G value) than the centroid positions $k_{G21}$ and $k_{G22}$ (step s7: Yes), the second determination threshold value setting unit 133 obtains a minimum value $k_{Min}$ of a distribution range of the two normal distributions D21 and D22 and sets the minimum value $k_{Min}$ as the determination threshold value (step s8).

Figure 12:
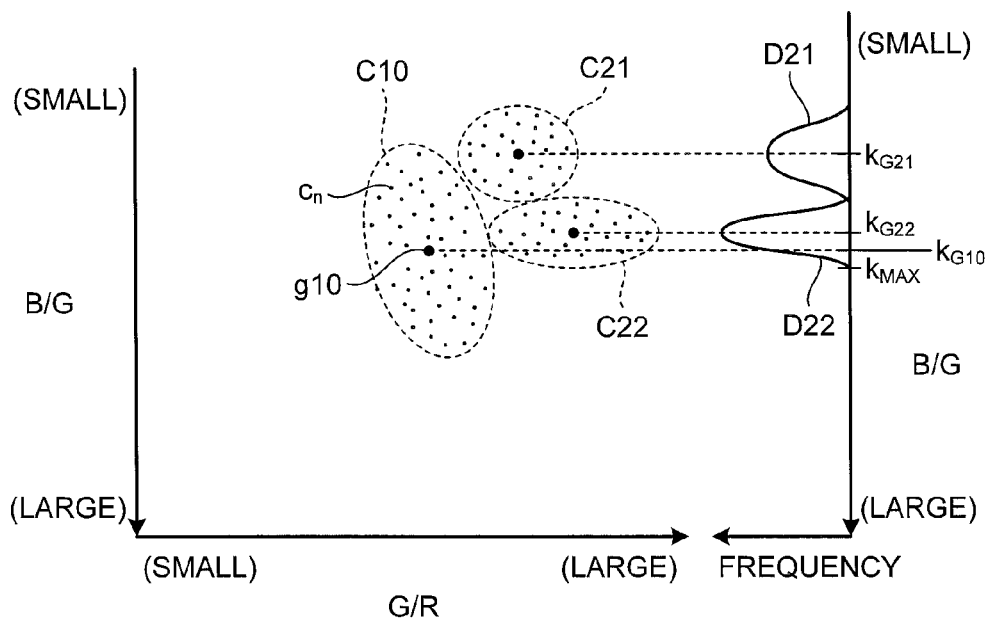
FIG. 12 is a diagram illustrating the method of setting the determination threshold value of the residue distribution.

On the contrary, as illustrated in FIG. 12, if the centroid positions $k_{G21}$ and $k_{G22}$ of the two normal distributions D21 and D22 are on a side stronger in yellowness (a side smaller in B/G value) than the centroid position $k_{G10}$ of the mucosa distribution (step s7: No), the second determination threshold value setting unit 133 obtains a maximum value $k_{Max}$ of the distribution range of the two normal distributions D21 and D22 and sets the maximum value $k_{Max}$ as the determination threshold value (step s9).

Figure 13:
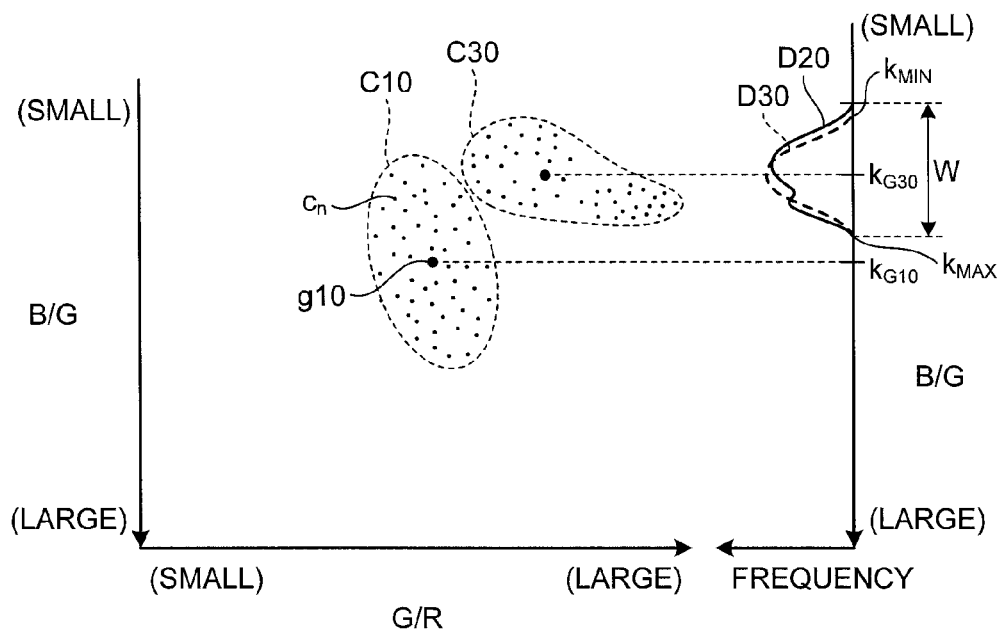
FIG. 13 is a diagram illustrating the method of setting the determination threshold value of the residue distribution.

Further, at step s2, if the width "W" of the histogram (distribution D20) is determined to be smaller than the specified value as illustrated in FIG. 13 (step s2: No), the second determination threshold value setting unit 133 approximates the histogram by one normal distribution D30 (step s10). The distribution C30 represented in a feature data space is a distribution of the color feature data $c_n$ corresponding to the normal distribution D30.

At step s11, the second determination threshold value setting unit 133 obtains a maximum value $k_{MAX}$, a minimum value $k_{MIN}$, and a centroid position $k_{30}$ of a distribution range of the normal distribution D30. When this is done, the second determination threshold value setting unit 133 may obtain the maximum value $k_{MAX}$, the minimum value $k_{MIN}$, and the centroid position $k_{30}$ of the distribution range, directly from the original histogram (the distribution D20 illustrated in FIG. 1), instead of from the normal distribution D30. In that case, step s10 may be omitted.

At step s12, the second determination threshold value setting unit 133 determines whether or not the centroid position $k_{G10}$ of the mucosa distribution is on a side stronger in yellowness than the centroid position $k_{G30}$ of the normal distribution D30.

If the centroid position $k_{G10}$ of the mucosa distribution is on the side stronger in yellowness (a side small in B/G value) than the centroid position $k_{G30}$ of the normal distribution D30 (step s12: Yes), the second determination threshold value setting unit 133 sets the minimum value $k_{Min}$ of the distribution range of the normal distribution D30 as the determination threshold value (step s13).

On the contrary, as illustrated in FIG. 13, if the centroid position $k_{G10}$ of the mucosa distribution is on a side weaker in yellowness (a side larger in B/G value) than the centroid position $k_{G30}$ of the normal distribution D30 (step s12: No, a case illustrated in FIG. 13), the second determination threshold value setting unit 133 sets the maximum value $k_{Max}$ of the distribution range of the normal distribution D30 as the determination threshold value (step s14).

Thereafter, the operations of the residue distribution determination unit 130 return to a sub-routine illustrated in FIG. 7.

At step S144 subsequent to step S143, the determination unit 134 determines, based on the determination threshold value, whether or not the residue candidate distribution corresponds to a residue distribution. In more detail, the determination unit 134 compares the representative value (for example, the centroid position) of each distribution that is the residue candidate with the determination threshold value, and determines a distribution having a representative value on a side stronger in yellowness than the determination threshold value to be a residue distribution and determines a distribution having a representative value on a side weaker in yellowness than the determination threshold value to be not a residue distribution. For example, in FIG. 10, the cluster C21 stronger in yellowness (smaller in B/G value) at the centroid position $k_{G21}$ than the boundary position $k_{BORDER}$ set as the determination threshold value is determined to be a residue distribution, and the cluster C22 weaker in yellowness (larger in B/G value) at the centroid position $k_{G22}$ than the boundary position $k_{BORDER}$ is determined to be not a residue distribution. Pixels having the color feature data determined to be the residue distribution as described above, are determined to be pixels of a residue region.

The determination unit 134 may determine whether or not each color feature data $c_n$ is included in a residue distribution by comparing each color feature data $c_n$ included in the residue candidate distribution with the determination threshold value.

Thereafter, the operations of the image processing apparatus 1 return to the main routine.

At step S15 subsequent to step S14, the computation unit 100 outputs a result of the determination in step S14. Accordingly, the control unit 10 causes the recording unit 50 to record therein the result of the determination and the display unit 40 to display the result of the determination.

As described above, in the first embodiment, on the candidate determination axis representing the color feature data that change in the strength of redness, the mucosa distribution and the residue distribution are distinguished, and subsequently, on the determination axis representing the color feature data that change in the strength of yellowness, the residue distribution is determined according to the relative relation between the residue candidate distribution and the mucosa distribution. That is, according to the first embodiment, because a residue distribution is distinguished by using a threshold value adaptively set based on a relative relation of color feature data in an intraluminal image to be processed, instead of a threshold value set beforehand by learning, a residue region is able to be detected more accurately than conventionally.

In particular, a residue region is large in variation in distributions of color feature data among intraluminal images and thus by adaptively setting a determination threshold value for each intraluminal image to be processed, detection accuracy of a residue region in each intraluminal image is able to be improved.

Modified Example 1-1

Next, a modified example 1-1 is described.

In the above described embodiment, the color feature data calculation unit 110 calculates the color feature data of each pixel in the intraluminal image to generate the distribution of the color feature data. However, the color feature data calculation unit 110 may divide an intraluminal image into a plurality of small regions and calculate color feature data in small region units. The small regions in which the intraluminal image is divided may be rectangular regions, each of a preset size. Or, by performing watershed processing or the like on a pixel value (R-value or G-value) of the intraluminal image or a luminance value "Y" calculated from the pixel value (Reference: Luc Vincent and Pierre Soille, "Watersheds in Digital Spaces An Efficient Algorithm Based on Immersion Simulations", IEEE Transactions on Pattern Analysis and Machine Intelligence, Vol. 13, No. 6, pp. 583-598, June 1991), the intraluminal image may be divided into a plurality of small regions. As a color feature data of the small region unit, for example, an average value of color feature data of pixels included in each small region is used.

In that case, the residue candidate distribution determination unit 120 and the residue distribution determination unit 130 perform the above described process, based on a distribution of the color feature data calculated in the small region units.

According to the modified example 1-1, by calculating the color feature data in small region units, influence by noises are able to be suppressed, and thus determination accuracy of unnecessary regions is able to be improved.

Modified Example 1-2

Next, a modified example 1-2 is described.

The candidate determination axis setting unit 121 may set the candidate determination axis, which is to be used in distinguishing between the mucosa region and the residue candidate region, correspondingly with color feature data small in variation of mucosa distributions among a plurality of intraluminal images. Accordingly, detection errors for mucosa regions are able to be decreased. In this case, by executing, for example, a least squares method, a regression method, an eigenvalue method, or the like using a linear function, in a color feature data space, which is a plot of color feature data in a mucosa region obtained beforehand from a plurality of intraluminal images, the candidate determination axis setting unit 121 detects a direction in which variance becomes minimum and sets color feature data corresponding to that direction as the candidate determination axis.

Modified Example 1-3

Next, a modified example 1-3 is described.

The determination axis setting unit 131 may set the determination axis, which is to be used in determining whether or not the residue candidate distribution corresponds to a residue distribution, correspondingly with color feature data large in a fluctuation range of residue candidate regions among intraluminal images. This is done, because a residue candidate distribution includes a plurality of distributions other than residue distributions, like a distribution corresponding to a white lesion region or a distribution corresponding to a halation region, in order to allow clear separation of these distributions. In this case, the determination axis setting unit 131 detects a direction in which variance becomes maximum, in a color feature data space, which is a plot of color feature data in a residue region obtained beforehand from a plurality of intraluminal images, and sets a coordinate axis related to color feature data corresponding to that direction as the determination axis.

Figure 14:
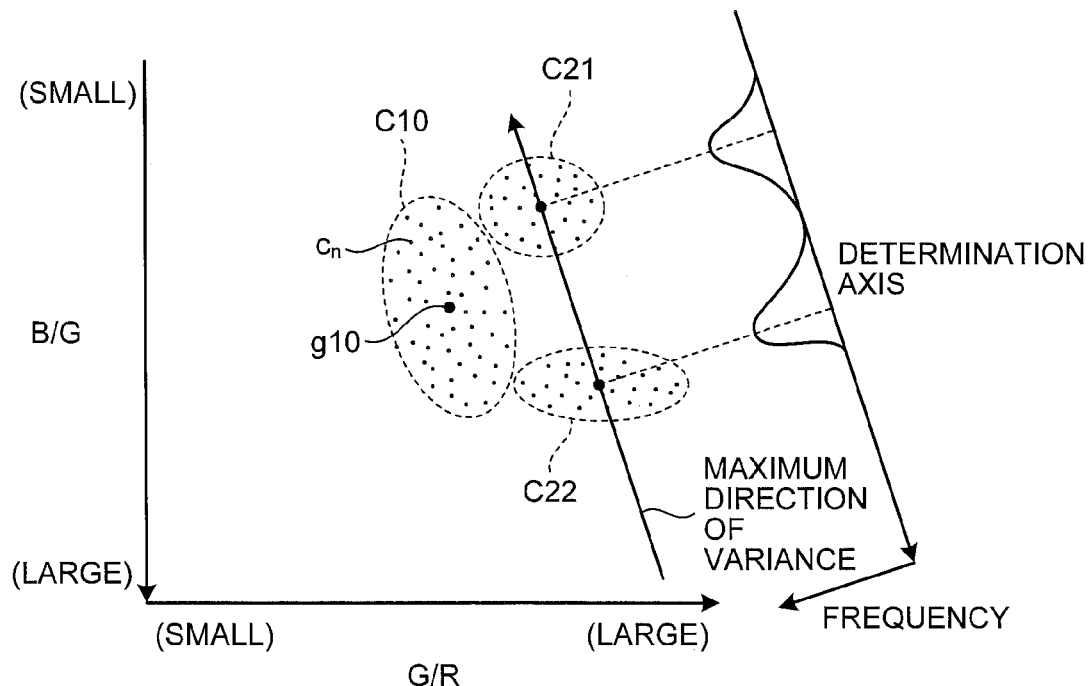
FIG. 14 is a diagram illustrating a determination axis in a modified example 1-3.

FIG. 14 illustrates an example in which a determination axis set correspondingly with color feature data large in variance among residue candidate distributions is displayed being overlapped with a color feature data space, which is a plot of color feature data of pixels in an intraluminal image to be processed. As illustrated in FIG. 14, if the set determination axis is not parallel with the axis of the color feature data space (that is, if the color feature data corresponding to the determination axis is different from both the G/R value and B/R value), the color feature data of the intraluminal image to be processed may preferably be plotted first in a color feature data space having G/R value and B/G value components and a frequency distribution of the color feature data may be accumulated with respect to the set determination axis.

Or, in another modified example, simply, a determination axis representing color feature data corresponding to an axis orthogonal to a candidate determination axis in a color feature data space may be set.

Modified Example 1-4

Next, a modified example 1-4 is described.

The first determination threshold value setting unit 123 may set the candidate determination threshold value to be used in distinguishing between a mucosa region and a residue candidate region, based on a distribution of color feature data obtained beforehand from a plurality of intraluminal images. In order to do so, first, the first determination threshold value setting unit 123 generates a frequency distribution of color feature data (for example, G/R values) of pixels in a mucosa region, for each intraluminal image, and divides the frequency distribution by watershed processing into mountains. Thereafter, a centroid position of each distribution obtained by the division into mountains is calculated. Subsequently, the first determination threshold value setting unit 123 generates a frequency distribution of centroid positions obtained from the plurality of intraluminal images. In this frequency distribution of the centroid positions, a value on a candidate determination axis, at which the frequency is minimum or locally minimum for the first time when a side weak in redness (for example, a side large in G/R value) is seen from a color feature data of the maximum frequency, is set as the candidate determination threshold value.

Modified Example 1-5

Next, a modified example 1-5 is described.

The candidate determination unit 124 may determine whether or not each cluster corresponds to a residue candidate distribution for respective clusters obtained by clustering color feature data of an intraluminal image to be processed. As a method of clustering, as described above, a known method, such as watershed processing, a hierarchy method, a k-means method, an EM algorithm, or self-organizing mapping may be used.

Figure 15:
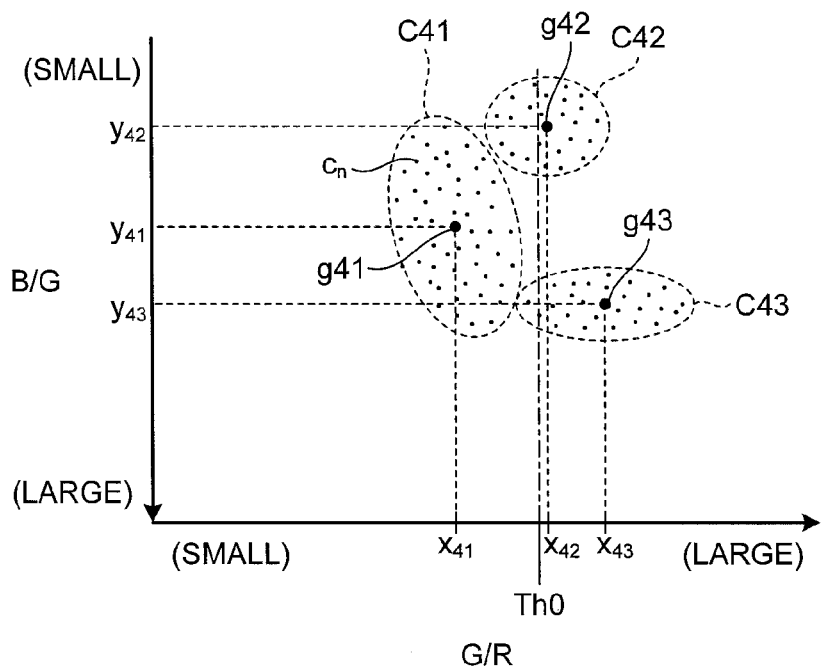
FIG. 15 is a diagram illustrating a method of determining a residue candidate distribution and a residue distribution in a modified example 1-5.

In this case, the candidate determination unit 124, as illustrated in FIG. 15, for example, obtains centroid positions g41 ($x_{41}$, $y_{41}$), g42 ($x_{44}$, $y_{42}$), and g43 ($x_{43}$, $y_{43}$) of respective clusters C41 to C43 obtained by clustering a distribution of color feature data in a color feature data space. The values $x_{41}$, $x_{42}$, and $x_{43}$ are centroid components on a candidate determination axis (G/R axis) of the centroid positions g41, g42, and g43, and values $y_{41}$, $y_{42}$, and $y_{43}$ are centroid components on a determination axis (B/G axis) of the centroid positions g41, g42, and g43.

The candidate determination unit 124 compares the centroid components $x_{41}$, $x_{42}$, and $x_{43}$ with the candidate determination threshold value Th0, and determines the cluster C41 having the centroid position on a side stronger in redness (side smaller in G/R value) than the candidate determination threshold value Th0 to be a mucosa distribution and determines the clusters C42 and C43 having the centroid positions on a side weaker in redness (side larger in G/R value) than the candidate determination threshold value Th0 to be residue candidate distributions.

Further, the determination unit 134 may determine whether or not each cluster corresponds to a residue distribution for the residue candidate distribution. In this case, as illustrated in FIG. 15, for example, the determination unit 134 compares the centroid components $y_{42}$ and $y_{43}$ of the clusters C42 and C43 determined to be the residue candidate distributions with the centroid component $y_{41}$ of the cluster C41 determined to be the mucosa distribution, and determines that the cluster C42 having the centroid position on a side stronger in yellowness (side smaller in B/G value) than the centroid position of the cluster C41 of the mucosa distribution to be a residue distribution and determines the cluster C43 having the centroid position on a side weaker in yellowness (side larger in B/G value) than the centroid position of the cluster C41 of the mucosa distribution to be not a residue distribution.

Or, if a determination threshold value, which is to be used in determining whether or not the residue candidate distribution corresponds to a residue distribution, has been obtained by the method described in the embodiment, the determination unit 134 may make the determination by comparing the centroid components $y_{42}$ and $y_{43}$ of the clusters C42 and C43 with this determination threshold value.

Modified Example 1-6

Next, a modified example 1-6 is described.

The first determination threshold value setting unit 123 may evaluate a bimodal shape of a histogram, similarly to the second determination threshold value setting unit 133, calculate a boundary position in the histogram based on a result of this evaluation, and set this boundary position as the determination threshold value.

That is, the first determination threshold value setting unit 123 approximates the histogram by two normal distributions by a method like an EM algorithm, if the histogram of the feature data generated with respect to the candidate determination axis has a width equal to or greater than a specified value. Subsequently, the first determination threshold value setting unit 123, based on a representative value (for example, a centroid position) of each normal distribution, on the candidate determination axis, makes comparison with a centroid position of a mucosa histogram obtained from teacher data, for example, and determines to which of a mucosa distribution and a residue candidate distribution each normal distribution corresponds. If the two normal distributions are determined to be corresponding to mucosa distributions, the first determination threshold value setting unit 123 sets a maximum value of a range of the two normal distributions as the determination threshold value. Further, if the two normal distributions are determined to be corresponding to residue candidate distributions, the first determination threshold value setting unit 123 sets a minimum value of the range of the two normal distributions as the determination threshold value. Furthermore, if one of the two normal distributions is determined to be corresponding to a mucosa distribution while the other is determined to be corresponding to a residue candidate distribution, the first determination threshold value setting unit 123 sets a boundary position between the two normal distributions as the determination threshold value.

Further, if the width of the histogram is equal to or less than the specified value, the first determination threshold value setting unit 123 approximates the histogram by one normal distribution. Subsequently, the first determination threshold value setting unit 123, based on a representative value (for example, a centroid position) of the normal distribution on the candidate determination axis, makes comparison with a centroid position of a mucosa histogram obtained from teacher data, for example, and determines to which of a mucosa distribution and a residue candidate distribution that normal distribution corresponds. If the normal distribution is determined to be corresponding to a mucosa distribution, the first determination threshold value setting unit 123 sets a maximum value in a range of the normal distribution as the determination threshold value. On the contrary, if the normal distribution is determined to be corresponding to a residue candidate distribution, the first determination threshold value setting unit 123 sets a minimum value in the range of the normal distribution as the determination threshold value.

Modified Example 1-7

Next, a modified example 1-7 is described.

Figure 16:
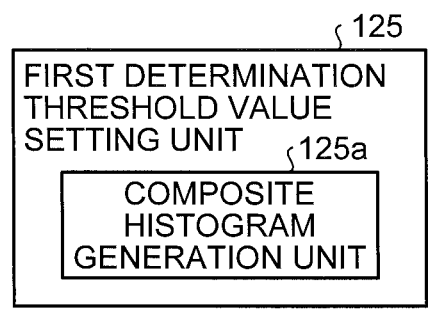
FIG. 16 is a block diagram illustrating a configuration of a first determination threshold value setting unit in a modified example 1-7.

In the modified example 1-7, instead of the first determination threshold value setting unit 123 illustrated in FIG. 1, as illustrated in FIG. 16, a first determination threshold value setting unit 125 including a composite histogram generation unit 125*a* may be utilized.

Figure 17:
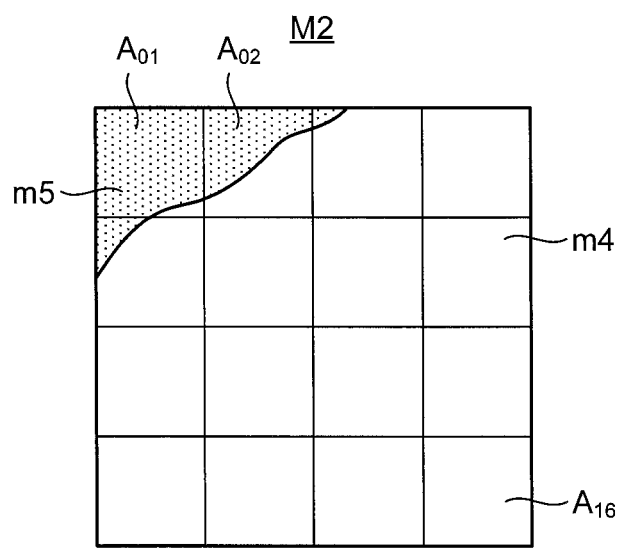
FIG. 17 is a diagram illustrating operations of a composite histogram generation unit illustrated in FIG. 16.

If, as exemplified as an image M2 of FIG. 17, one of regions (for example, a mucosa region m4) to be determined is photographed in a large portion of the intraluminal image, the other of the regions to be determined (for example, a residue region m5) is only barely captured, and one histogram is generated by using color feature data of pixels of the whole intraluminal image, there is a risk that frequencies corresponding to the small region are buried in noises and a mucosa distribution and a residue distribution corresponding to both of the regions are not able to be distinguished appropriately.

Figure 18:
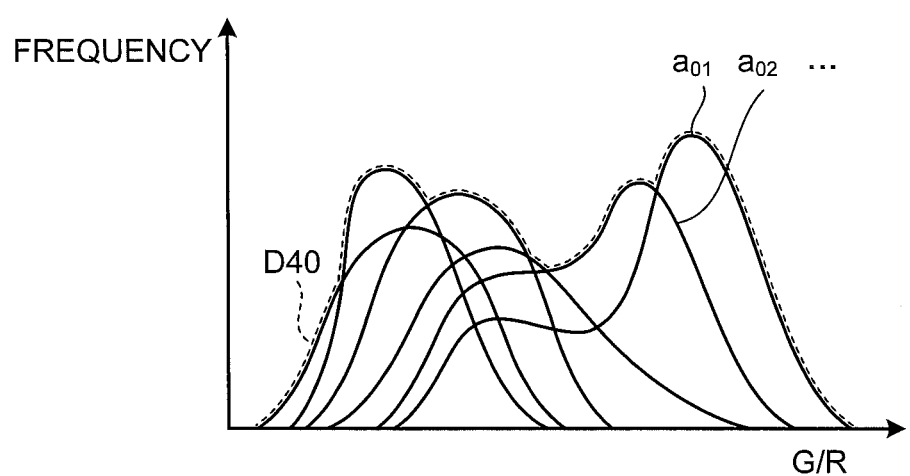
FIG. 18 is a diagram illustrating a composite histogram.

In such a case, the composite histogram generation unit 125*a* first divides the intraluminal image into a plurality of rectangular regions each of a specified size, and for each rectangular region, generates a histogram representing a frequency distribution of color feature data of pixels with respect to the candidate determination axis. For example, in FIG. 17, one image M2 is divided into 16 rectangular regions $A_{01}$ to $A_{16}$, and for each of rectangular regions $A_{01}$ to $A_{16}$, 16 histograms $a_{01}$ to $a_{16}$ illustrated in FIG. 18 are generated. Subsequently, the composite histogram generation unit 125*a* generates a composite histogram composed of these histograms. As illustrated in FIG. 18, a composite histogram D40 is formed by extracting and combining maximum values of frequency among the histograms $a_{01}$ to $a_{16}$ for each color feature data. Or, instead of the maximum values, mode values may be extracted to generate the composite histogram.

According to this modified example 1-7, even if any of a mucosa region and a residue region is extremely small, in a composite histogram generated with respect to a candidate determination axis, characteristics of a distribution corresponding to a ratio between the mucosa region and the residue region in each rectangular region are expressed. Therefore, an appropriate determination threshold value is settable and a mucosa region and a residue candidate region are distinguishable.

Second Embodiment

Next, a second embodiment of the present invention will be described.

Figure 19:
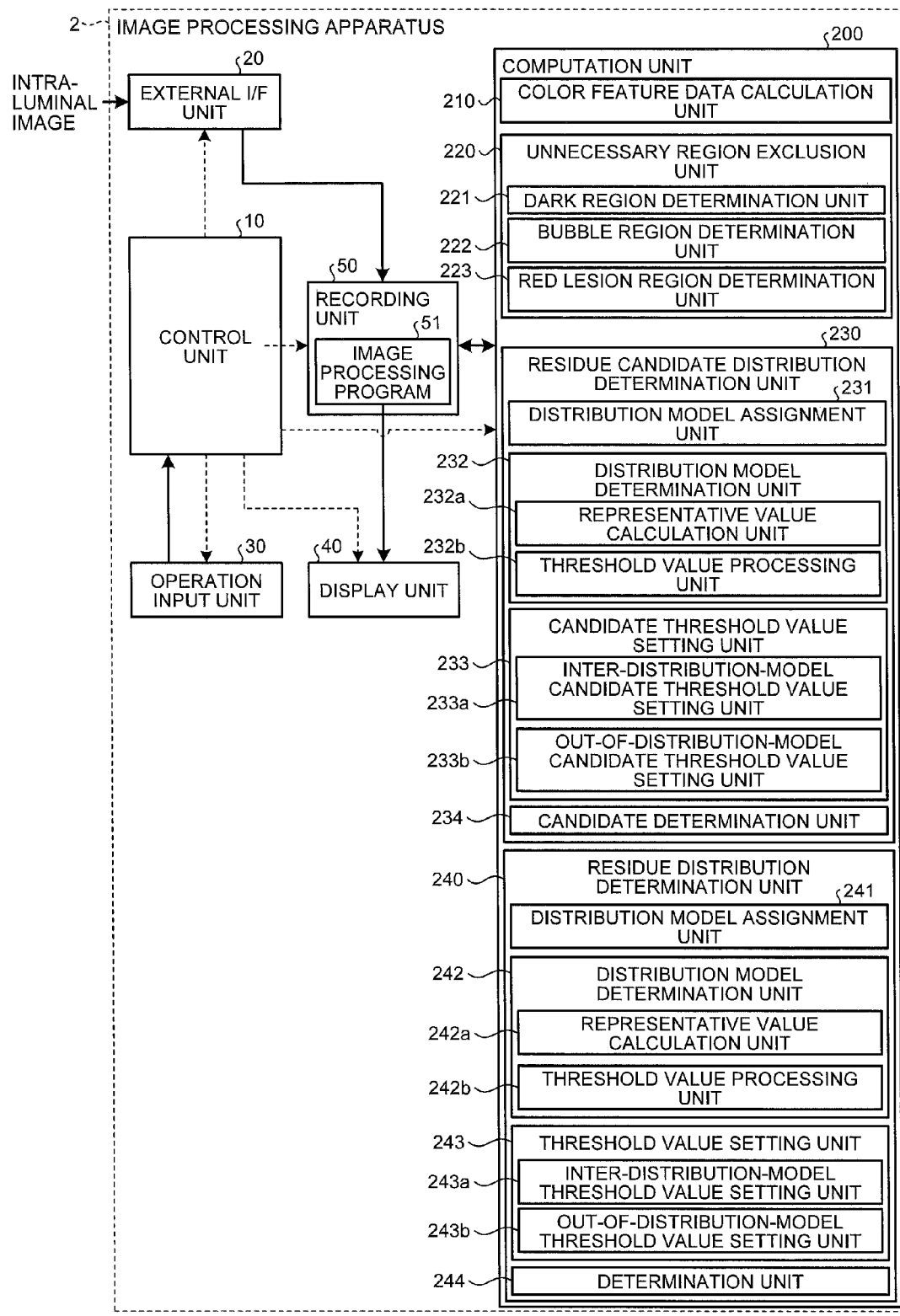
FIG. 19 is a block diagram illustrating a configuration of an image processing apparatus according to a second embodiment of the present invention.

FIG. 19 is a block diagram illustrating a configuration of an image processing apparatus according to a second embodiment of the present invention. As illustrated in FIG. 19, an image processing apparatus 2 according to the second embodiment includes a computation unit 200, instead of the computation unit 100 illustrated in FIG. 1. A configuration and operations of each unit other than the computation unit 200 are similar to those of the first embodiment.

The computation unit 200 includes: a color feature data calculation unit 210 that calculates color feature data for each pixel or small region in an intraluminal image to generate a distribution; an unnecessary region exclusion unit 220 that excludes from the intraluminal image a region unnecessary for determination of a residue region; a residue candidate distribution determination unit 230 that determines color feature data representing a residue candidate, based on redness of color feature data in the intraluminal image; and a residue distribution determination unit 240 that determines color feature data representing a residue, based on yellowness of the color feature data determined to be the residue candidate. Of these, operations of the color feature data calculation unit 210 are similar to those of the color feature data calculation unit 110 illustrated in FIG. 1.

The unnecessary region exclusion unit 220 includes a dark region determination unit 221, a bubble region determination unit 222, and a red lesion region determination unit 223, and by respective ones of these units, excludes regions determined respectively as a bubble region, a dark region, and a red lesion region as unnecessary regions. Operations of the dark region determination unit 221, the bubble region determination unit 222, and the red lesion region determination unit 223 are similar respectively to those of the dark region determination unit 122a-1, the bubble region determination unit 122a-2, and the red lesion region determination unit 122a-3 illustrated in FIG. 1.

The residue candidate distribution determination unit 230 includes a distribution model assignment unit 231, a distribution model determination unit 232, a candidate threshold value setting unit 233, and a candidate determination unit 234, and determines color feature data distributed on a side comparatively weak in redness to be a residue candidate distribution. Of these, the distribution model assignment unit 231 assigns one or more distribution models to a distribution of color feature data in the intraluminal image on a candidate determination axis (first determination axis) for determining redness. The distribution model determination unit 232 determines, based on redness of the one or more distribution models, whether or not each distribution model is a residue candidate, by comparing the one or more distribution models with a specified threshold value (fixed value) that is set beforehand. The candidate threshold value setting unit 233 sets, based on a result of the determination by the distribution model determination unit 232, a candidate threshold value for determining color feature data representing a residue candidate. The candidate determination unit 234 determines the color feature data representing a residue candidate, based on the set candidate threshold value.

The distribution model determination unit 232 includes: a representative value calculation unit 232a that calculates a representative value of the one or more distribution models on the candidate determination axis; and a threshold value processing unit 232b that determines, based on a threshold value that is set beforehand on the candidate determination axis correspondingly with the representative value, a distribution model weak in redness to be a residue candidate distribution.

Further, the candidate threshold value setting unit 233 includes: an inter-distribution-model candidate threshold value setting unit 233a that sets, if as a result of the determination by the distribution model determination unit 232, the determination is made resulting differently from one another among a plurality of distribution models, a value among the plurality of distribution models on the candidate determination axis, as a candidate threshold value; and an out-of-distribution-model candidate threshold value setting unit 233b that sets, if the determination is made resulting identically to one another among the plurality of distribution models or if only one distribution is assigned to the color feature data, a value outside of the one or more distribution models on the candidate determination axis setting unit, as the candidate threshold value.

The residue distribution determination unit 240 includes a distribution model assignment unit 241, a distribution model determination unit 242, a threshold value setting unit 243, and a determination unit 244, and determines, from among the color feature data determined to be the residue candidate, color feature data on a side comparatively strong in yellowness to be a residue distribution. Of these, the distribution model assignment unit 241 assigns one or more distribution models to the distribution of the color feature data determined to be the residue candidate, on a determination axis (second determination axis) of color feature data for determining yellowness. The distribution model determination unit 242 determines, based on yellowness of the one or more distribution models, whether or not each distribution model is a residue, by comparing the one or more distribution models with a specified threshold value (fixed value) that is set beforehand. The threshold value setting unit 243 sets, based on a result of the determination by the distribution model determination unit 242, a threshold value for determining color feature data representing a residue. The determination unit 244 determines the color feature data representing a residue, based on the threshold value set by the threshold value setting unit 243.

The distribution model determination unit 242 includes a representative value calculation unit 242a that calculates a representative value of the one or more distribution models on the determination axis; and a threshold value processing unit 242b that determines, based on a threshold value preset on the determination axis correspondingly with the representative value, a distribution model strong in yellowness, to be a residue distribution.

Figure 20:
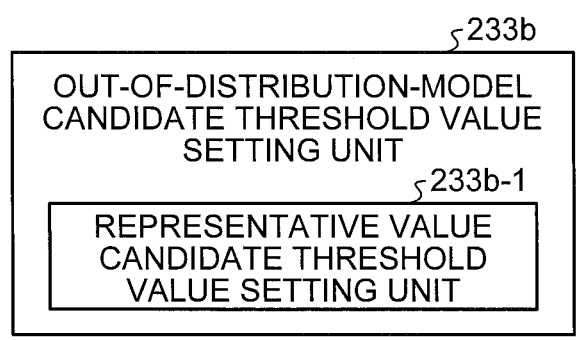
FIG. 20 is a block diagram illustrating a detailed configuration of an out-of-distribution-model candidate threshold value setting unit illustrated in FIG. 19.

FIG. 20 is a block diagram illustrating a detailed configuration of the out-of-distribution-model candidate threshold value setting unit 233b illustrated in FIG. 19. As illustrated in FIG. 20, the out-of-distribution-model candidate threshold value setting unit 233b includes a representative value candidate threshold value setting unit 233b-1 that sets the representative value of the distribution model on the candidate determination axis as the candidate threshold value.

Figure 21:
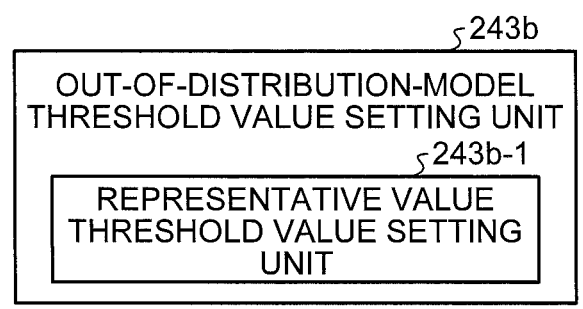
FIG. 21 is a block diagram illustrating a detailed configuration of an out-of-distribution-model threshold value setting unit illustrated in FIG. 19.

FIG. 21 is a block diagram of a detailed configuration of the out-of-distribution-model threshold value setting unit 243b illustrated in FIG. 19. As illustrated in FIG. 21, the out-of-distribution-model threshold value setting unit 243b includes a representative value threshold value setting unit 243b-1 that sets the representative value of the distribution model on the determination axis as the threshold value.

Figure 22:
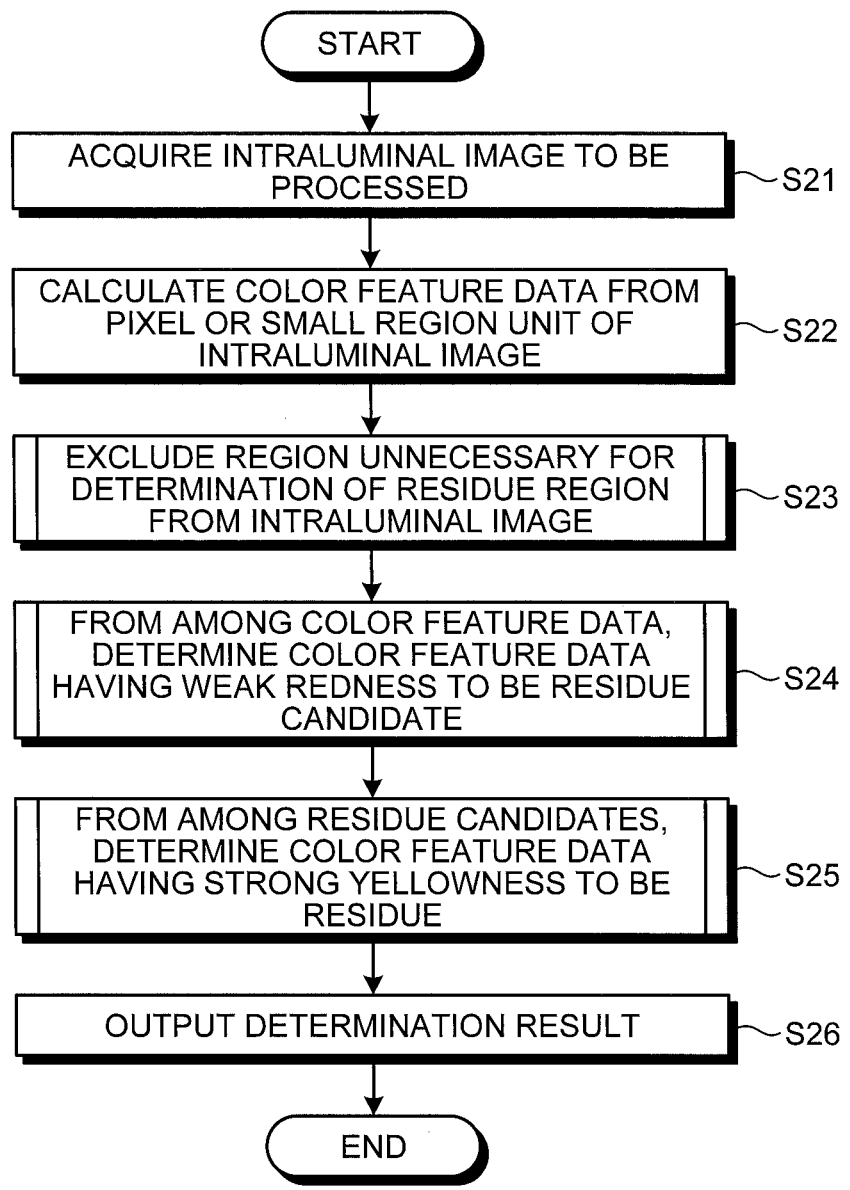
FIG. 22 is a flow chart illustrating operations of the image processing apparatus illustrated in FIG. 19.

Next, operations of the image processing apparatus 2 are described. FIG. 22 is a flow chart illustrating the operations of the image processing apparatus 2. Steps S21 and S26 illustrated in FIG. 22 correspond respectively to steps S11 and S15 illustrated in FIG. 2.

At step S22 subsequent to step S21, the color feature data calculation unit 210 calculates color feature data from pixel values (R-component, G-component, and B-component) of each pixel in an intraluminal image. In the second embodiment, as a color feature data expressing redness, a G/R value, which is a ratio of a G-component to an R-component, is calculated, and as a color feature data expressing yellowness, a B/G value, which is a ratio of a B-component to a G-component, is calculated. In the second embodiment also, similarly to the modified example 1-1, instead of obtaining the color feature data of each pixel, color feature data may be calculated in small region units obtained by dividing the intraluminal image into a plurality of small regions.

Figure 23:
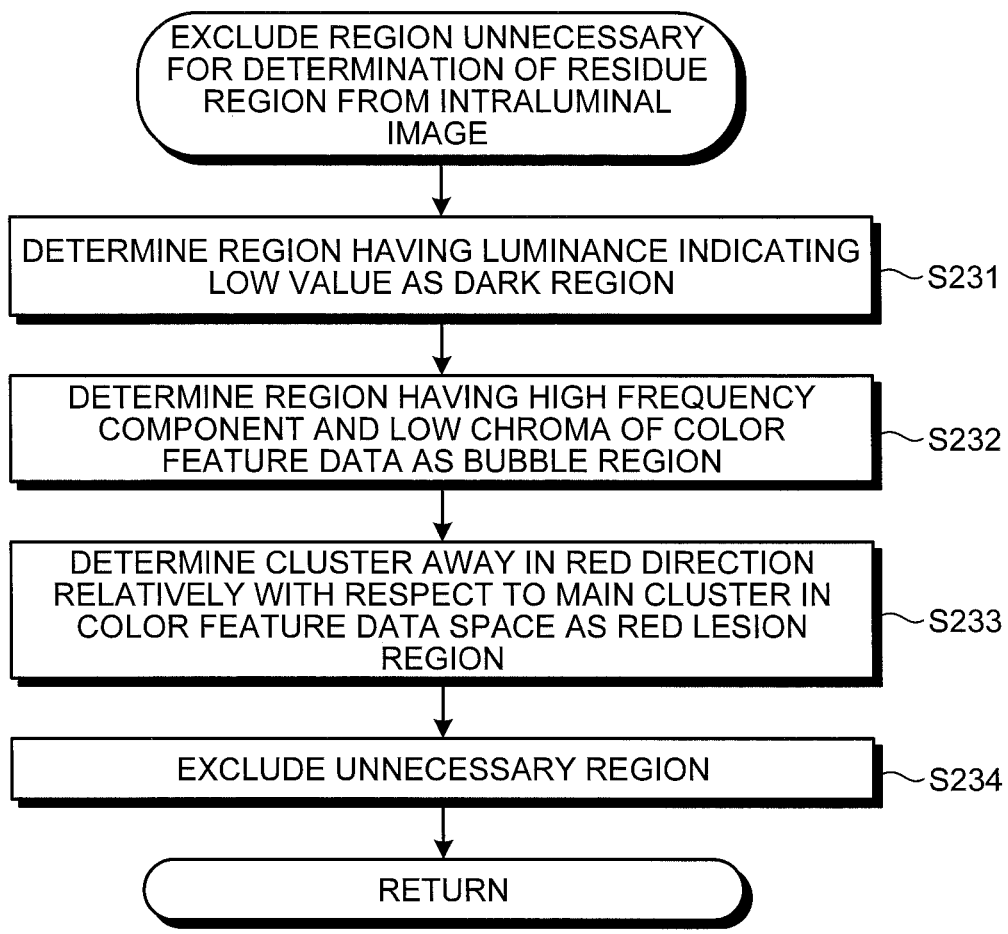
FIG. 23 is a flow chart illustrating operations of an unnecessary region exclusion unit illustrated in FIG. 19.

Subsequently, at step S23, the unnecessary region exclusion unit 220 excludes a region unnecessary for determination of a residue region from the intraluminal image. FIG. 23 is a flow chart illustrating operations of the unnecessary region exclusion unit 220.

First, at step S231, the dark region determination unit 221 determines a region (pixel or small region) having a luminance value less than a specified threshold value to be a dark region. For example, a region having a strength of a red component of the intraluminal image equal to or less than a specified threshold value is determined as the dark region. If the dark region is detected, the dark region determination unit 221 adds a flag (1: dark region) indicating a dark region to that region. The determination is performed based on the red component because a red component is least likely to be absorbed in a lumen and mostly reflected at a surface of a subject (mucosa) and thus represents structural information of the mucosa.

Subsequently, at step S232, the bubble region determination unit 222 determines a region (pixel or small region) having a high frequency component of a luminance value and a low chroma, to be a bubble region. If the bubble region is detected, the bubble region determination unit 222 adds a flag (2: bubble region) indicating a bubble region to that region. The frequency component is able to be found by calculating a coefficient obtained after performing DCT conversion (discrete cosine transform) on the intraluminal image, or a difference value or the like between the original image and its average image. The chroma is able to be determines by determination of whether or not both the G/B value and B/G value are distributed in a specified range or by threshold processing with respect to the luminance value and red component.

Subsequently, at step S233, the red lesion region determination unit 223 performs clustering, in a color feature data space having the G/R values and B/G values as its components, on a distribution of the color feature data, and determines a cluster away in a comparatively red direction with respect to a main cluster (a cluster of high frequency, for example, a largest cluster) to be a red lesion region. The clustering is performed by subjecting the frequency distribution of the color feature data in the color feature data space to watershed processing, mountain by mountain of the frequency distribution. If an absolute position of the cluster away from the main cluster or a comparative position of the cluster away from the main cluster with respect to the main cluster is in the red direction, the red lesion region determination unit 223 adds a flag (3: red lesion region) indicating a red lesion region to the region of the intraluminal image corresponding to that cluster.

To a region not added with any of the flags "1" to "3" in steps S231 to S233, an "other" flag (0: other) is added. At step S234, the unnecessary region exclusion unit 220 excludes, from the pixels or small regions of the intraluminal image, any pixels or small regions added with the flags "1" to "3", as the unnecessary regions. Thereafter, the operations of the computation unit 200 return to the main routine.

Figure 24:
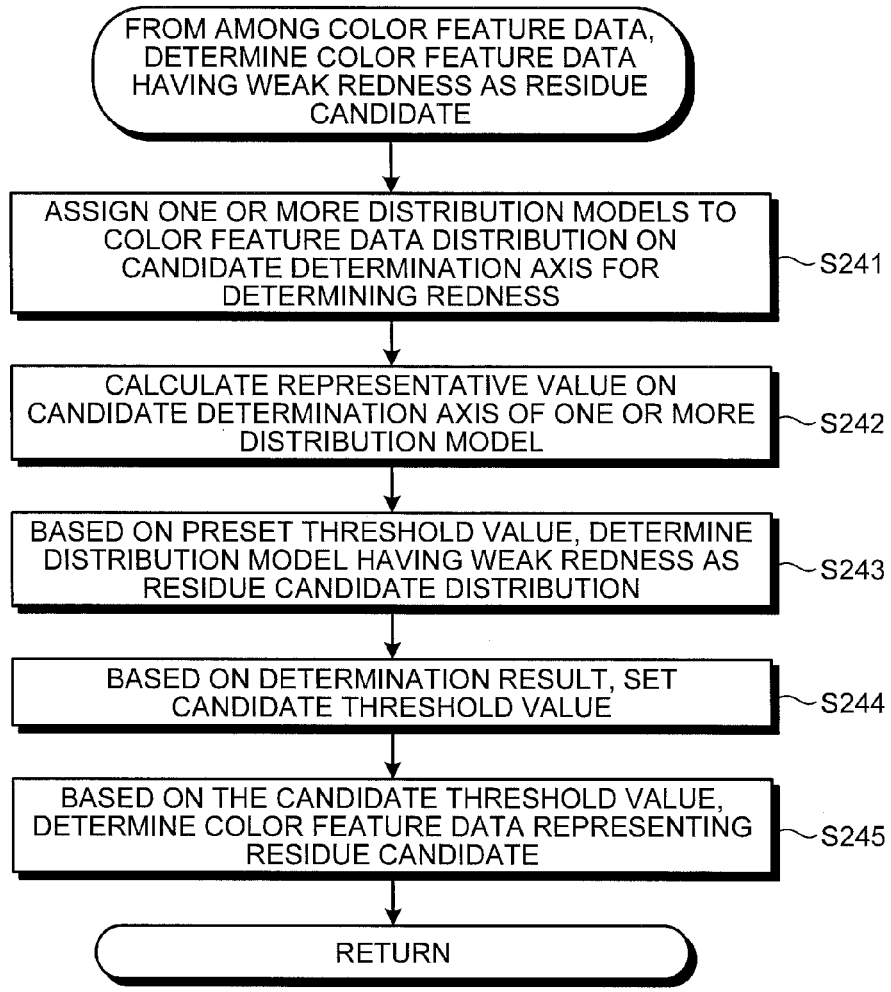
FIG. 24 is a flow chart illustrating operations of a residue candidate distribution determination unit illustrated in FIG. 19.

At step S24 subsequent to step S23, the residue candidate distribution determination unit 230 determines the color feature data weak in redness, from among the color feature data, to be a residue candidate. FIG. 24 is a flow chart illustrating operations of the residue candidate distribution determination unit 230.

First, at step S241, the distribution model assignment unit 231 generates one or more distribution models by assigning a specified distribution model to a distribution of color feature data on a candidate determination axis for determining redness. In the second embodiment, as the candidate determination axis, the G/R value, which becomes stronger in redness as "0" is approached, is set. Further, in the second embodiment, one normal distribution is or two normal distributions are assigned to the distribution of the color feature data.

A normal distribution $f_k(i)$ is given by the following Equation (1).

$$f_k(i) = \omega_k \frac{1}{\sqrt{2\pi\sigma_k^2}} \exp\left\{-\frac{(i-\mu_k)^2}{2\sigma_k^2}\right\} \tag{1}$$

Equation (1) represents a k-th normal distribution assigned to the distribution of the color feature data and in the second embodiment, k=1 or 2. Further, the symbol "i" represents the color feature data, G/R value.

This normal distribution $f_k(i)$ is able to be found by an EM algorithm technique of updating, based on the color feature data, an average $\mu_k$, a variance $\sigma_k^2$, and a mixing ratio $\omega_k$, which are parameters, to find an optimum solution (Reference: J. A. Bilmes, A Gentle Tutorial of the EM Algorithm and its Application to Parameter Estimation for Gaussian Mixture and Hidden Markov Models, "Technical Report TR-97-021, International Computer Science Institute and Computer Science Division, University of California at Berkeley, April 1998).

Hereinafter, with reference to FIG. 25 to FIG. 28B, an outline of an EM algorithm is described.

An EM algorithm is an algorithm in which an E-step (expectation) and an M-step (maximization) described below are repeated with respect to a finite number of data (for example, the color feature data, G/R values) on a certain data axis (for example, the candidate determination axis) and processing is ended when the repeat count or the logarithm likelihood has become close to the maximum value.

<E-step>
(i) Step 1

Figure 25:
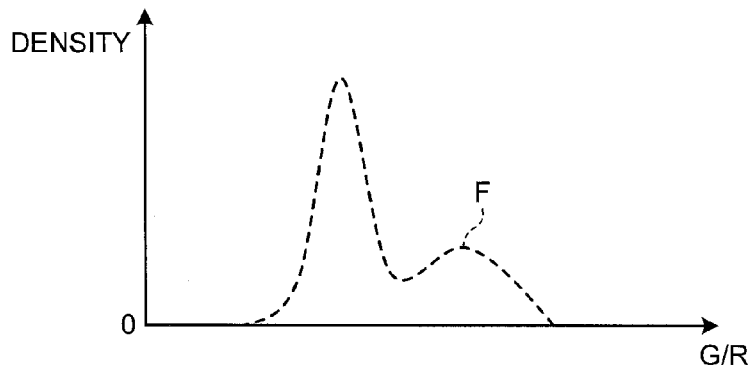
FIG. 25 is a schematic diagram illustrating an outline of an EM algorithm.
Figure 26:
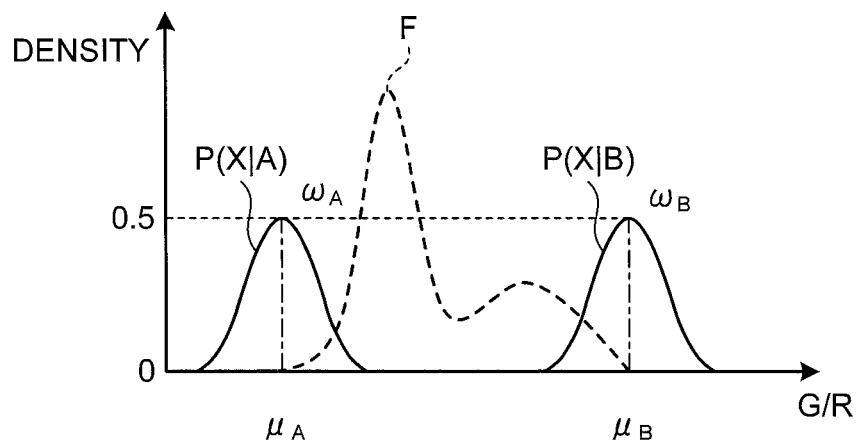
FIG. 26 is a schematic diagram illustrating the outline of the EM algorithm.

For example, as illustrated in FIG. 25, with respect to a density function "F" of "N" ("N" is a natural number) data $X=\{x_i\}$ (i=1, 2, ..., N)" on a certain data axis, a probability model indicating which of distributions "A" and "B" the data "X" belong to is defined by two normal distributions (see FIG. 26). Various parameters of the two normal distributions are defined as follows.

Average: $\mu_A$, $\mu_B$
Variance: $\sigma_A^2$, $\sigma_B^2$
Mixing ratio of distribution "A" and distribution "B" (prior probabilities): $\omega_A$, $\omega_B$.
Probability models (probability densities) for the data "X" belonging to the distributions "A" and "B", $\omega_A P(X|A)$ and $\omega_B P(X|B)$, respectively are given by the next Equations (2) and (3).

$$\omega_A P(X|A) = \omega_A \frac{1}{\sqrt{2\pi\sigma_A^2}} \exp\left\{-\frac{(X-\mu_A)^2}{2\sigma_A^2}\right\} \quad (2)$$

$$\omega_A P(X|B) = \omega_B \frac{1}{\sqrt{2\pi\sigma_B^2}} \exp\left\{-\frac{(X-\mu_B)^2}{2\sigma_B^2}\right\} \quad (3)$$

FIG. 26 illustrates a case in which an initial value of each parameter in Equations (2) and (3) is set as follows.
Average $\mu_A$: a minimum value of the density function "F"
Average $\mu_B$: a maximum value of the density function "F"
Variance $\sigma_A^2$: 1.0
Variance $\sigma_B^2$: 1.0
Mixing ratio $\omega_A$: 0.5
Mixing ratio $\omega_B$: 0.5(=1−$\omega_A$)

(ii) Step 2

Figure 27:
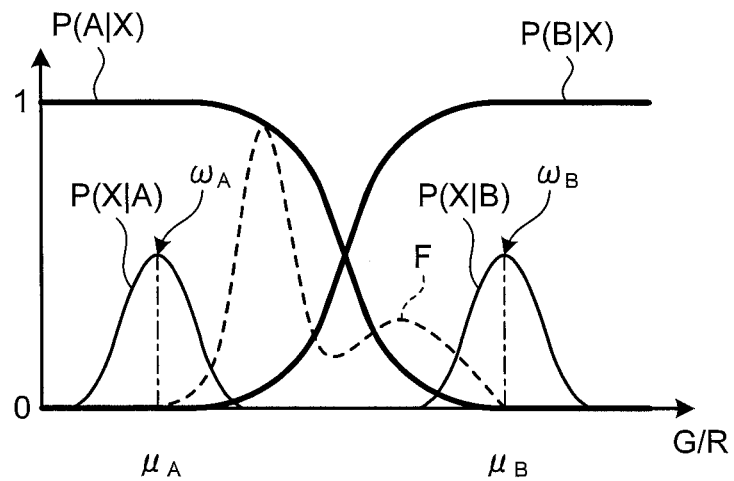
FIG. 27 is a schematic diagram illustrating the outline of the EM algorithm.

From the probability densities expressed in Equations (2) and (3), posterior probabilities P(A|X) and P(B|X) indicating which of the distributions "A" and "B" a position of a certain data on the G/R axis belongs to are calculated using Equations (4) and (5) (See FIG. 27).

$$P(A|X) = \frac{\omega_A P(X|A)}{\omega_A P(X|A) + \omega_B P(X|B)} \quad (4)$$

$$P(B|X) = \frac{\omega_B P(X|B)}{\omega_A P(X|A) + \omega_B P(X|B)} \quad (5)$$

Since the data "X" belongs to one of the distributions "A" and "B", as expressed by the next equation, a sum of the probabilities is "1".

$$P(A|X)+P(B|X)=1$$

(iii) Step 3

Using a likelihood $Q(X|\omega, \mu, \sigma^2)$ expressed by the next Equation (6), whether or not a probability model has been assigned to the density function "F" is evaluated. A logarithmic likelihood is used in the evaluation. The logarithmic likelihood takes a maximum value in a most likely state.

$$Q(X|\omega, \mu, \sigma^2) = \sum_x \{P(A|x) \times \log(P(x|A)) + P(B|x) \times \log(P(x|B))\} \quad (6)$$

<M-Step>
(iv) Step 4

The parameters of the probability models are updated. Updating of the averages $\mu_A$ and $\mu_B$ is performed using Equations (7) and (8), updating of the variances $\sigma_A^2$ and $\sigma_B^2$ is performed using Equations (9) and (10), and updating of the mixing ratios $\omega_A$ and $\omega_B$ is performed using Equations (11) and (12), respectively.

$$\mu_A^{(1)} = \frac{\sum_i \{P(A|X)^{(0)} x_i\}}{\sum_i P(A|X)^{(0)}} \quad (7)$$

$$\mu_B^{(1)} = \frac{\sum_i \{P(B|X)^{(0)} x_i\}}{\sum_i P(B|X)^{(0)}} \quad (8)$$

$$\sigma_A^{(1)2} = \frac{\sum_i \{P(A|X)^{(0)}(x_i - \mu_A^{(1)})^2\}}{\sum_i P(A|X)^{(0)}} \quad (9)$$

$$\sigma_B^{(1)2} = \frac{\sum_i \{P(B|X)^{(0)}(x_i - \mu_B^{(1)})^2\}}{\sum_i P(B|X)^{(0)}} \quad (10)$$

$$\omega_A^{(1)} = \frac{1}{N} \sum_i P(A|X)^{(0)} \quad (11)$$

$$\omega_B^{(1)} = \frac{1}{N} \sum_i P(B|X)^{(0)} \quad (12)$$

The symbol (0) expressed in Equations (7) to (12) indicate that each parameter is of the initial value, and the symbol (1) indicates that each parameter is of a value after the first update. This symbol (j) (j=0, 1, 2, . . . ) is incremented according to the number of updates.

Figure 28A:
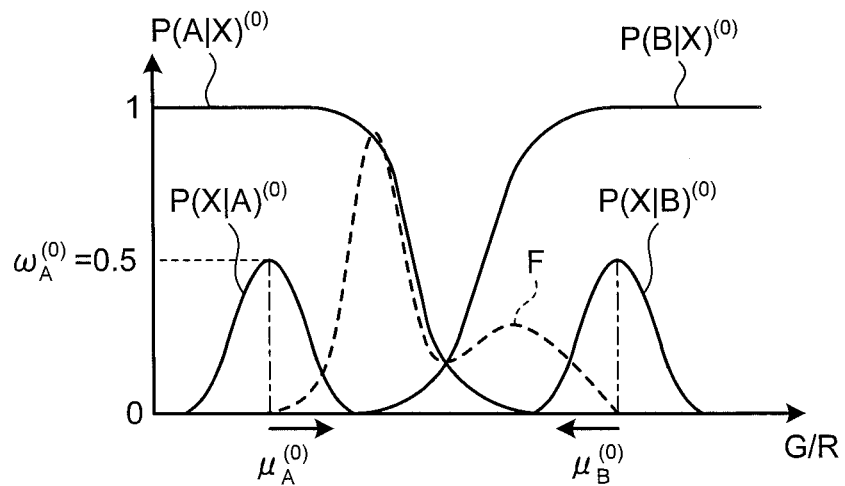
FIG. 28A is a schematic diagram illustrating the outline of the EM algorithm.
Figure 28B:
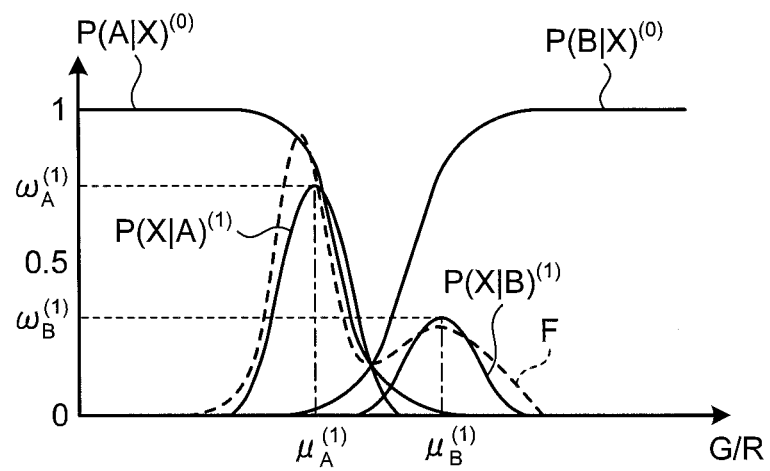
FIG. 28B is a schematic diagram illustrating the outline of the EM algorithm.

For example, as illustrated in FIG. 28A, when an average $\mu_A^{(0)}$, a variance $\sigma G_A^{(0)2}$, a mixing ratio $\omega_A^{(0)}$, which are initial parameters of the distribution "A", are updated once, as illustrated in FIG. 28B, an average $\mu_A^{(1)}$, a variance $\sigma_A^{(1)2}$, a mixing ratio $\omega_A^{(1)}$, which are the updated parameters, are obtained. It is similar for the distribution "B".

By repeating these E-steps and M-steps, optimum parameters of the distributions "A" and "B" are able to be found.

Figure 29:
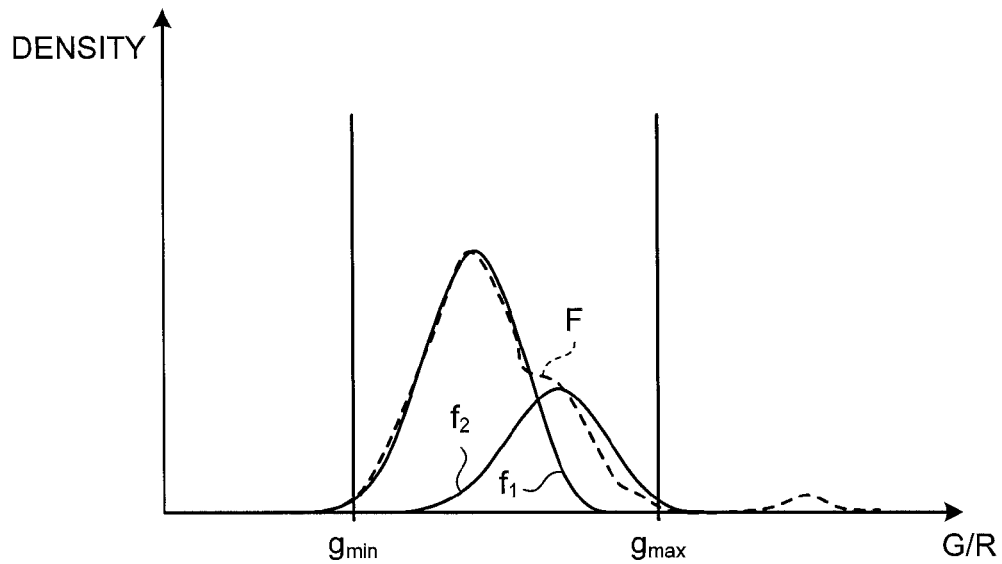
FIG. 29 is a diagram illustrating a representative value of one or more distribution models on a candidate determination axis.

At step S242 subsequent to step S241 (See FIG. 24), the representative value calculation unit 232a of the distribution model determination unit 232 calculates the representative value on the candidate determination axis of the one or more distribution models generated by the distribution model assignment unit 231. Specifically, as illustrated in FIG. 29, as the representative values, a maximum value $g_{max}$ and a minimum value $g_{min}$ of a distribution range of the distribution model are calculated.

Figure 30:
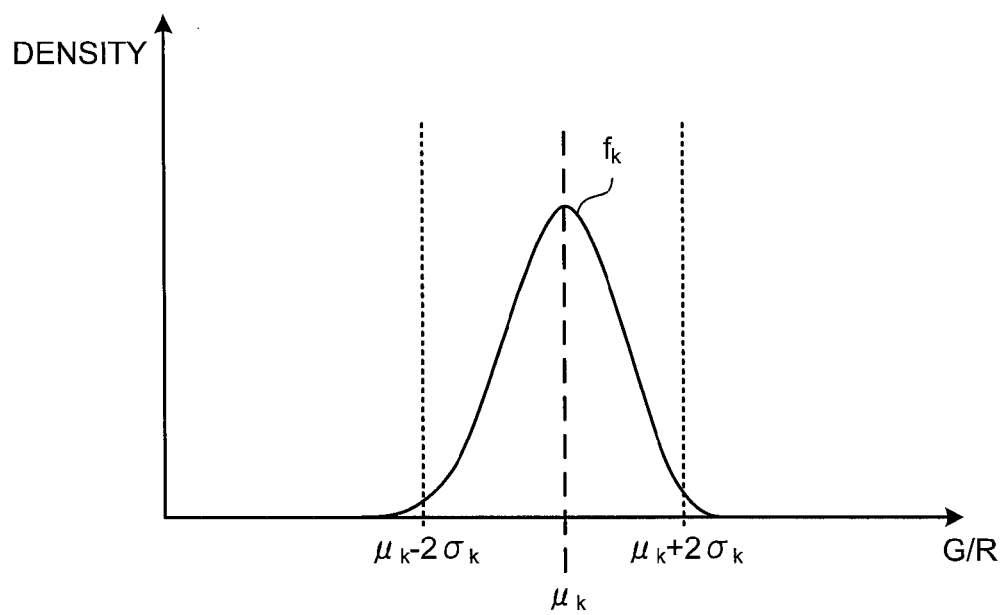
FIG. 30 is a diagram illustrating a method of calculating a representative value of a distribution model.

In more detail, the representative value calculation unit 232a first obtains, as illustrated in FIG. 30, an average $\mu_k$ and a variance $\sigma_k^2$, which are parameters of each normal distribution $f_k$. Thereafter, values of the color feature data away from the average $\mu_k$ by ±2$\sigma_k$ are taken as a maximum value a $g_{max(fk)}$ (=$\mu_k$+2$\sigma_k$) and a minimum value $g_{min(fk)}$ (=$\mu_k$−2$\sigma_k$) of the distribution range of the normal distribution $f_k$.

Figure 31:
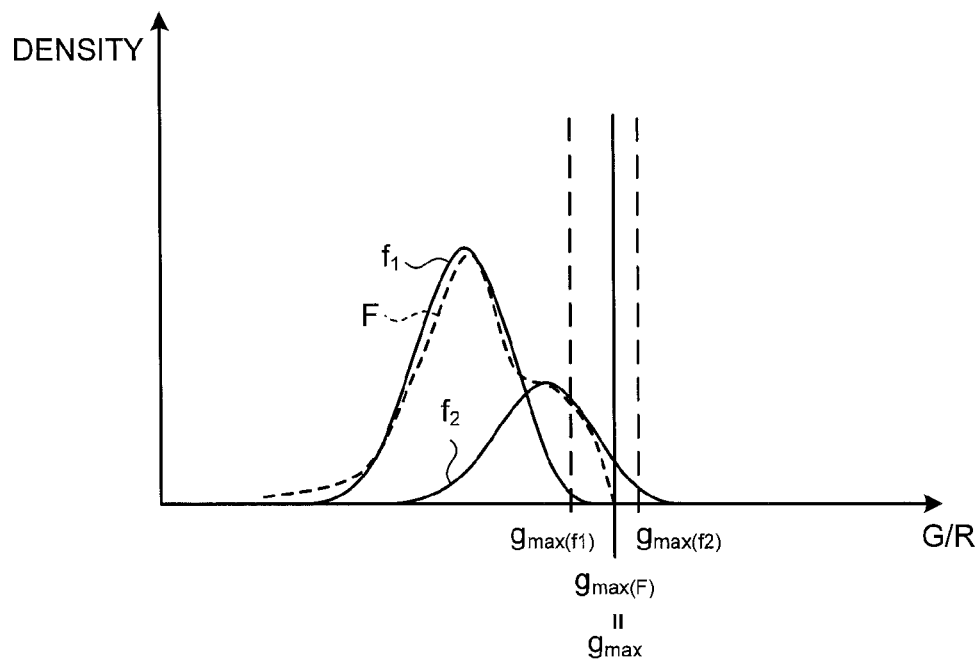
FIG. 31 is a diagram illustrating the method of calculating a representative value of a distribution model.

Subsequently, the representative value calculation unit 232a obtains a maximum value max($g_{max(fk)}$) among the maximum values $g_{max(fk)}$ of the one or more normal distributions $f_k$. For example, if normal distributions $f_1$ and $f_2$ illustrated in FIG. 31 are obtained, the maximum value $g_{max(f2)}$ of the normal distribution $f_2$ is obtained as the maximum value max($g_{max(fk)}$).

Figure 32:
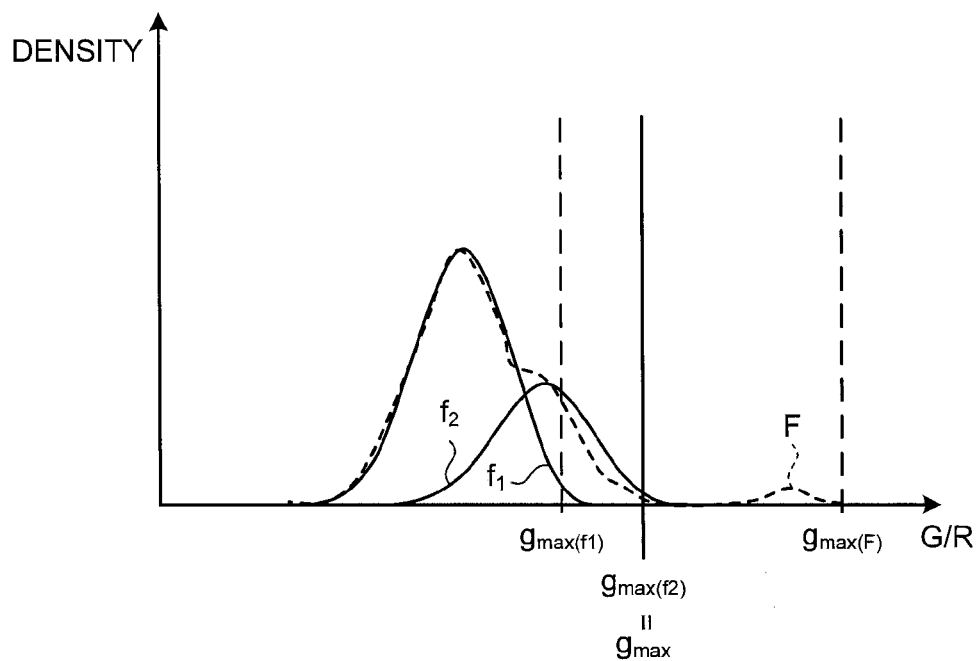
FIG. 32 is a diagram illustrating the method of calculating a representative value of a distribution model.

Subsequently, the representative value calculation unit 232a obtains a maximum value $g_{max(F)}$ of the distribution range of the color feature data, and by comparing it with the maximum value max($g_{max(fk)}$) of the normal distribution $f_k$, sets a smaller one of the compared values as a maximum value $g_{max}$ of the distribution range of the distribution models. For example, in FIG. 31, because the maximum value $g_{max(f2)}$ of the normal distribution $f_2$ is large and over the actual maximum value $g_{max(F)}$ of the density function "F", the maximum value $g_{max(F)}$ of the density function "F" is set as the maximum value $g_{max}$ of the distribution range of the distribution models ($g_{max}=g_{max(F)}$). On the contrary, in FIG. 32, since the maximum value $g_{max(f2)}$ of the normal distribution $f_2$ is smaller than the maximum value $g_{max(F)}$ of the density function "F", the maximum value a $g_{max(f2)}$ of the normal distribution $f_2$ is set as the maximum value $g_{max}$ of the distribution range of the distribution models ($g_{max}=g_{max(f2)}$).

Figure 33:
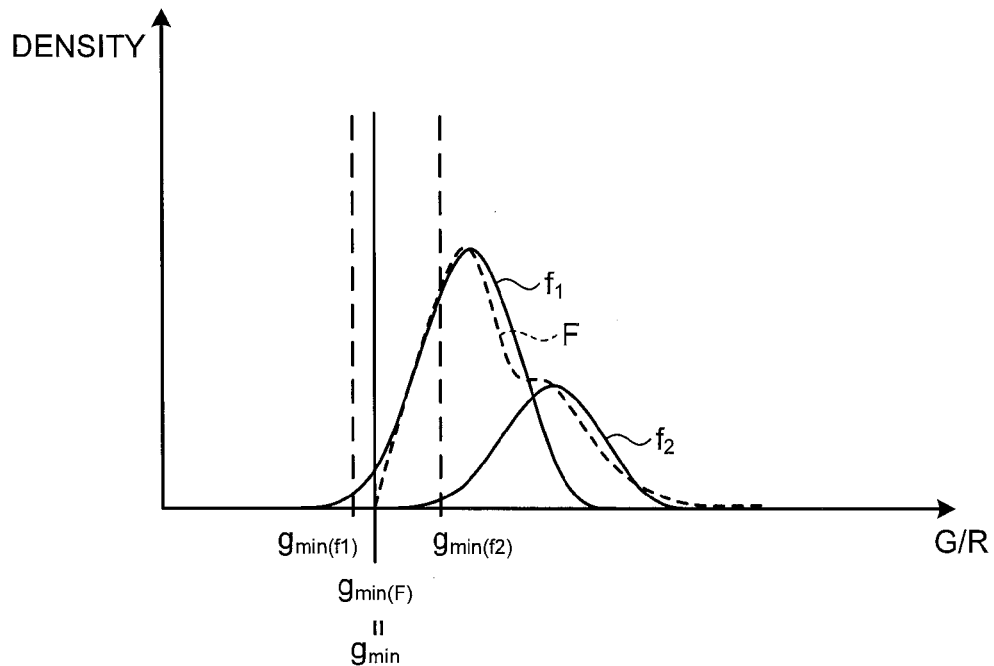
FIG. 33 is a diagram illustrating the method of calculating a representative value of a distribution model.

Further, the representative value calculation unit 232a obtains a minimum value min($g_{min(fk)}$) among the minimum values $g_{min(fk)}$ of the one or more normal distributions $f_k$. For example, in FIG. 33, between the normal distributions $f_1$ and $f_2$, the minimum value $g_{min(f1)}$ of the normal distribution $f_1$ is obtained as the minimum value min ($g_{min(fk)}$).

Figure 34:
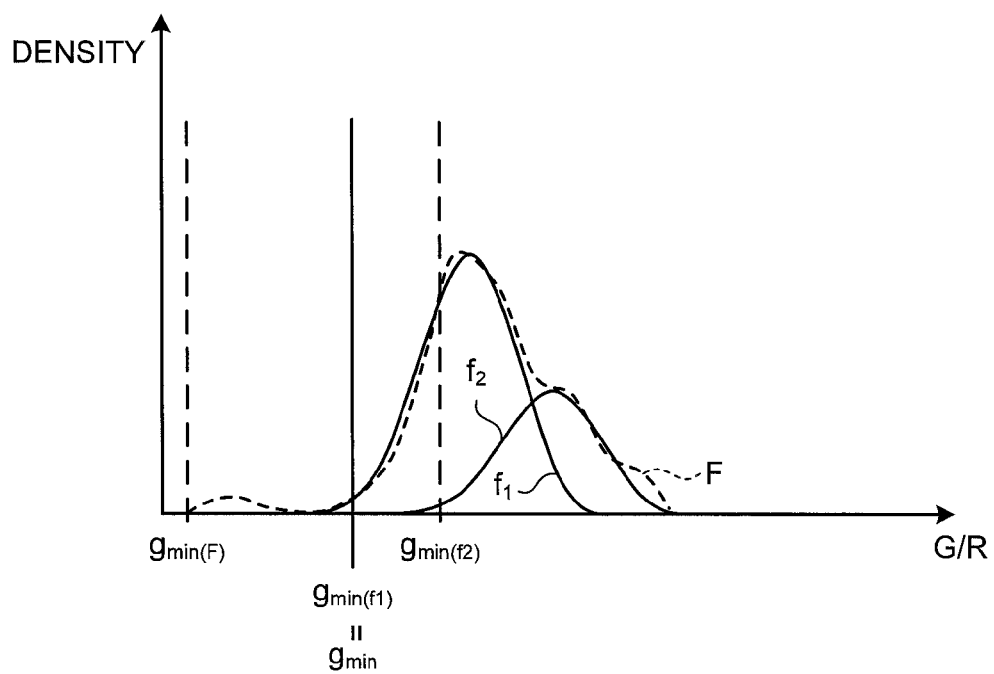
FIG. 34 is a diagram illustrating the method of calculating a representative value of a distribution model.

Subsequently, the representative value calculation unit 232a obtains the minimum value $g_{min(F)}$ of the distribution range of the color feature data, compares it with the minimum value min($g_{min(fk)}$) of the normal distribution $f_k$, and sets a larger one of the compared values as the minimum value $g_{min}$ of the distribution range of the distribution models. For example, in FIG. 33, because a minimum value $g_{min(f1)}$ of the normal distribution $f_1$ is small and less than the actual minimum value $g_{min(F)}$ of the density function "F", the minimum value $g_{min(F)}$ of the density function "F" is set as the minimum value $g_{min}$ of the distribution range of the distribution models ($g_{min}=g_{min(F)}$). On the contrary, in FIG. 34, since the minimum value $g_{min(f1)}$ of the normal distribution $f_1$ is greater than the minimum value $g_{min(F)}$ of the density function "F", the minimum value $g_{min(f1)}$ of the normal distribution $f_1$ is set as the minimum value $g_{min}$ of the distribution range of the distribution models ($g_{min}=g_{min(f1)}$).

If the number of normal distributions assigned to the distribution of the color feature data is one in step S241, the maximum value $\mu+2\mu$ and the minimum value $\mu-2\sigma$ of that normal distribution are respectively compared with the maximum value $g_{max(F)}$ and maximum value $g_{min(F)}$ of the distribution range of the color feature data, and based on a result of the comparison, the maximum value $g_{max}$ and minimum value $g_{min}$ of the distribution range of the distribution model are set.

Subsequently, at step S243, the threshold value processing unit 232b determines, based on the threshold value preset on the candidate determination axis, a distribution model weak in redness to be a residue candidate distribution. On the candidate determination axis, a mucosa threshold value Th(M) for determining presence or absence of mucosa and a residue candidate threshold value Th(R)(Th(R)>Th(M)) for determining presence or absence of residue candidate are set beforehand.

Figure 35:
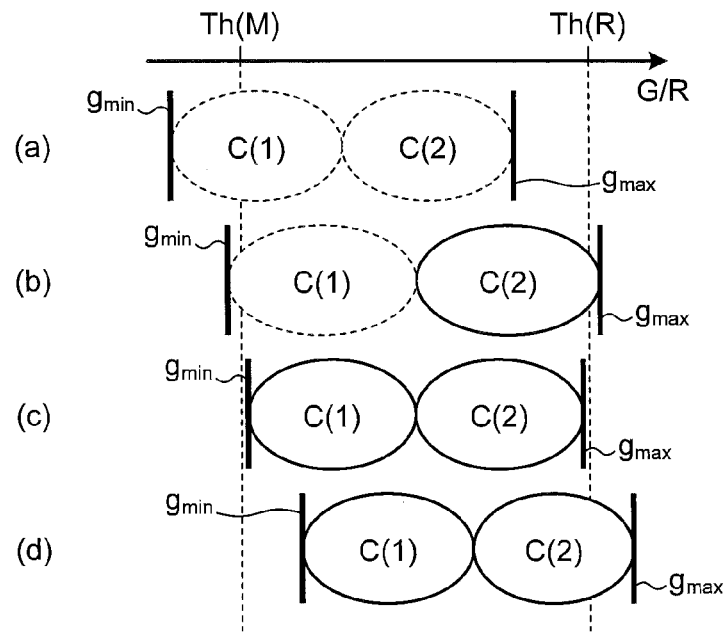
FIG. 35 is a schematic diagram illustrating a method of determining a residue candidate distribution for clusters of color feature data.
Figure 36:
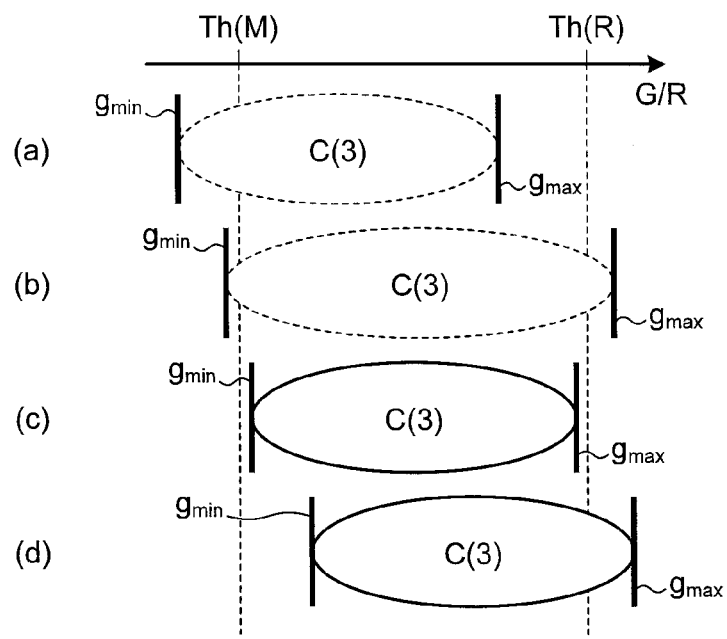
FIG. 36 is a schematic diagram illustrating the method of determining a residue candidate distribution for a cluster of color feature data.

FIG. 35 and FIG. 36 illustrate clusters generated by clustering the color feature data based on the one or more distribution models generated in step S241. The clustering is able to be performed, for example, by generating a frequency distribution of color feature data of an intraluminal image in a color feature data space, and subjecting the frequency distribution to watershed processing or the like.

Of these, FIG. 35 illustrates two clusters C(1) and C(2) corresponding to a case in which two distribution models are assigned to a distribution of color feature data, and one of these clusters having smaller color feature data (G/R) is defined as the cluster C(1) and the one having larger color feature data is defined as the cluster C(2). On the contrary, FIG. 36 illustrates a cluster C(3) corresponding to a case in which when two distribution models are assigned to a distribution of color feature data, one of the distributions is included in the other one of the distributions. Hereinafter, as an example of a distribution model, a method of determining whether or not these clusters C(1) to C(3) are residue candidate distributions (residue candidate clusters) is described.

As illustrated in FIG. 35(a), if a maximum value of a distribution range of a distribution model (that is, a maximum value of color feature data in clusters, hereinafter, "maximum value of clusters") $g_{max}$ is less than the residue candidate threshold value Th(R) ($g_{max}<$Th(R)), and a minimum value of the distribution range of the distribution model (that is, a minimum value of the color feature data in the clusters, hereinafter, "minimum value of the clusters") $g_{min}$ is equal to or less than the mucosa threshold value Th(M) ($g_{min}\leq$Th(M)), the threshold value processing unit 232b determines that both the clusters C(1) and C(2) are mucosa distributions.

As illustrated in FIG. 35(b), if the maximum value $g_{max}$ of the clusters is equal to or greater than the residue candidate threshold value Th(R) ($g_{max}\geq$Th(R)) and the minimum value $g_{min}$ of the clusters is equal to or less than the mucosa threshold value Th(M) ($g_{min}\leq$Th(M)), the threshold value processing unit 232b determines the cluster C(1) to be a mucosa distribution, and the cluster C(2) to be a residue candidate distribution.

As illustrated in FIG. 35(c), if the maximum value $g_{max}$ of the clusters is less than the residue candidate threshold value Th(R) ($g_{max}<$Th(R)), and the minimum value $g_{min}$ of the clusters is greater than the mucosa threshold value Th(M) ($g_{min}>$Th(M)), the threshold value processing unit 232b determines that both the clusters C(1) and C(2) are residue candidate distributions.

As illustrated in FIG. 35(d), if the maximum value $g_{max}$ of the clusters is equal to or greater than the residue candidate threshold value Th(R) ($g_{max}\geq$Th(R)), and the minimum value $g_{min}$ of the clusters is greater than the mucosa threshold value Th(M) ($g_{min}>$Th(M)), the threshold value processing unit 232b determines both the clusters C(1) and C(2) to be residue candidate distributions.

Further, as illustrated in FIG. 36(a), if the maximum value $g_{max}$ of the clusters is less than the residue candidate threshold value Th(R) ($g_{max}<$Th (R)), and the minimum value $g_{min}$ of the clusters is equal to or less than the mucosa threshold value Th(M) ($g_{min}\leq$Th (M)), the threshold value processing unit 232b determines the cluster C(3) to be a mucosa distribution.

As illustrated in FIG. 36(b), if the maximum value $g_{max}$ of the clusters is equal to or greater than the residue candidate threshold value Th(R) ($g_{max}\geq$Th(R)), and the minimum value $g_{min}$ of the clusters is equal to or less than the mucosa threshold value Th (M) ($g_{min}\leq$Th(M)), the threshold value processing unit 232b determines the cluster C(3) to be a mucosa distribution.

As illustrated in FIG. 36(c), if the maximum value $g_{max}$ of the clusters is less than the residue candidate threshold value Th(R) ($g_{max}<$Th(R)), and the minimum value $g_{min}$ of the clusters is greater than the mucosa threshold value Th(M) ($g_{min}>$Th(M)), the threshold value processing unit 232b determines the cluster C(3) to be residue candidate distribution.

As illustrated in FIG. 36(d), if the maximum value $g_{max}$ of the clusters is equal to or greater than the residue candidate threshold value Th(R) ($g_{max}\geq$Th(R)), and the minimum value $g_{min}$ of the clusters is greater than the mucosa threshold value Th(M) ($g_{min}>$Th(M)), the threshold value processing unit 232b determines the cluster C(3) to be a residue candidate distribution.

Subsequently, at step S244, the candidate threshold value setting unit 233 sets, based on a result of the determination in step S243, the candidate threshold value determining the color feature data representing a residue candidate. In more detail, if determination results different from one another among the plurality of clusters are obtained, the inter-distribution-model candidate threshold value setting unit 233a sets, as the candidate threshold value, a value among the plurality of clusters on the candidate determination axis (G/R axis). On the contrary, if determination results identical to one another among the plurality of clusters are obtained, the out-of-distribution-model candidate threshold value setting unit 233b sets, as the candidate threshold value, a value outside the clusters on the candidate determination axis.

Figure 37:
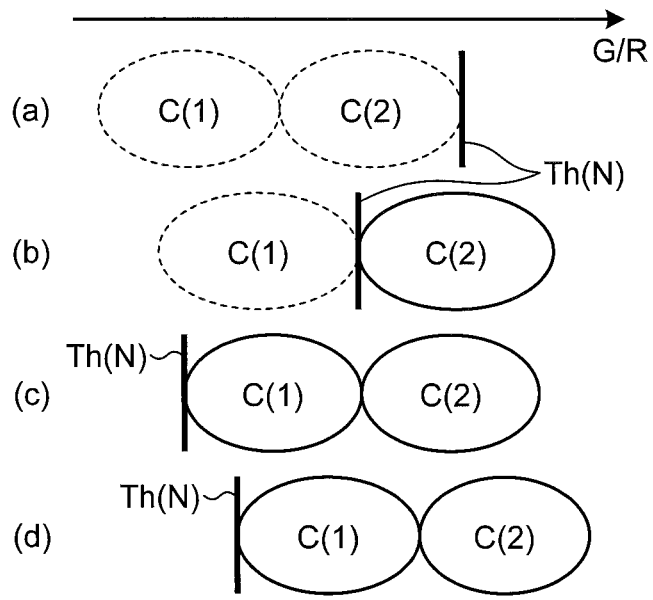
FIG. 37 is a schematic diagram illustrating a method of setting a candidate threshold value that determines color feature data representing a residue candidate.

Specifically, as illustrated in FIG. 35(a), if both of the two clusters C(1) and C(2) are determined to be mucosa distributions, the inter-distribution-model candidate threshold value setting unit 233a sets, as illustrated in FIG. 37(a), as a candidate threshold value Th(N), the maximum value $g_{max}$, which is a value outside the clusters C(1) and C(2) and on a side weak in redness (a side large in G/R value) on the candidate determination axis.

Further, as illustrated in FIG. 35(b), if the cluster C(1) is determined to be a mucosa distribution and the cluster C(2) is determined to be a residue candidate distribution, the out-of-distribution-model candidate threshold value setting unit 233b sets, as illustrated in FIG. 37(b), the color feature data at the boundary position between the clusters C(1) and C(2) on the candidate determination axis (that is, the value of the boundary position of the normal distributions $f_1$ and $f_2$ (see FIG. 29)) as the candidate threshold value Th(N).

Further, as illustrated in FIGS. 35(c) and (d), if the two clusters C(1) and C(2) are both determined to be residue candidate distributions, the out-of-distribution-model candidate threshold value setting unit 233b sets, as illustrated in FIGS. 37(c) and (d), the minimum value $g_{min}$, which is a value outside the clusters C(1) and C(2) and on a side strong in redness of the candidate determination axis (side small in G/R value) as the candidate threshold value Th(N).

On the contrary, if determination with respect to one cluster is made in step S243, the candidate threshold value setting unit 233 sets the candidate threshold value as described below.

Figure 38:
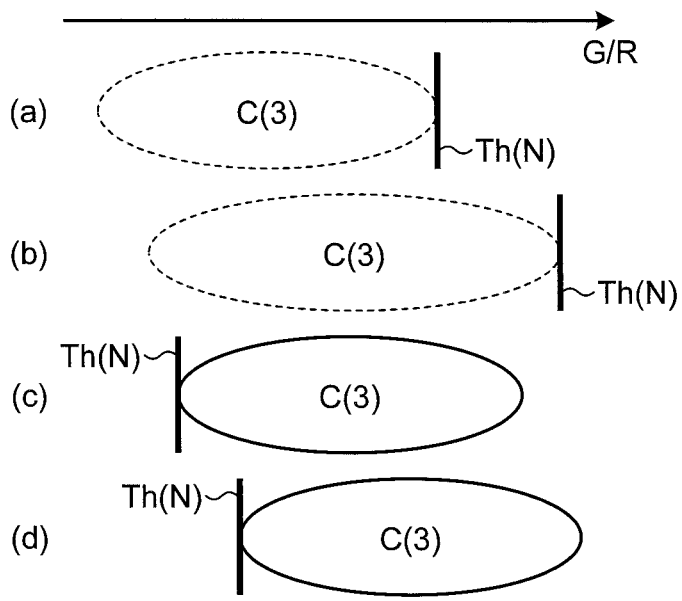
FIG. 38 is a schematic diagram illustrating the method of setting a candidate threshold value that determines color feature data representing a residue candidate.

That is, as illustrated in FIGS. 36(a) and (b), if the cluster C(3) is determined to be a mucosa distribution, the out-of-distribution-model candidate threshold value setting unit 233b sets, as illustrated in FIGS. 38(a) and (b), the maximum value $g_{max}$, which is a value on a side weak in redness on the candidate determination axis (side large in G/R value) as the candidate threshold value Th(N).

Further, as illustrated in FIGS. 36(c) and (d), if the cluster C(3) is determined to be a residue candidate region, the out-of-distribution-model candidate threshold value setting unit 233b sets, as illustrated in FIGS. 38(c) and (d), the minimum value $g_{min}$, which is a value on a side strong in redness on the candidate determination axis (side small in G/R value) as the candidate threshold value Th(N).

Subsequently at step S245, the candidate determination unit 234 determines, based on the candidate threshold value Th(N), the color feature data representing a residue candidate, from among each color feature data in the intraluminal image. Specifically, the candidate determination unit 234 determines, on the candidate determination axis, the color feature data present on a side stronger in redness than the candidate threshold value Th(N) (that is, smaller in G/R value) to represent a mucosa, and determines the color feature data present on a side weaker in redness (that is, larger in G/R value) to represent a residue candidate.

The candidate determination unit 234 may perform the above described determination for each cluster generated by clustering the color feature data in the intraluminal image. In that case, a centroid position of each cluster is calculated, a cluster having a centroid position present on a side stronger in redness than the candidate threshold value Th(N) is determined to be a mucosa distribution, and a cluster having a centroid position present on a side weaker in redness than the candidate threshold value Th(N) is determined to be a residue candidate distribution. Thereafter, the operations of the computation unit 200 return to the main routine.

Figure 39:
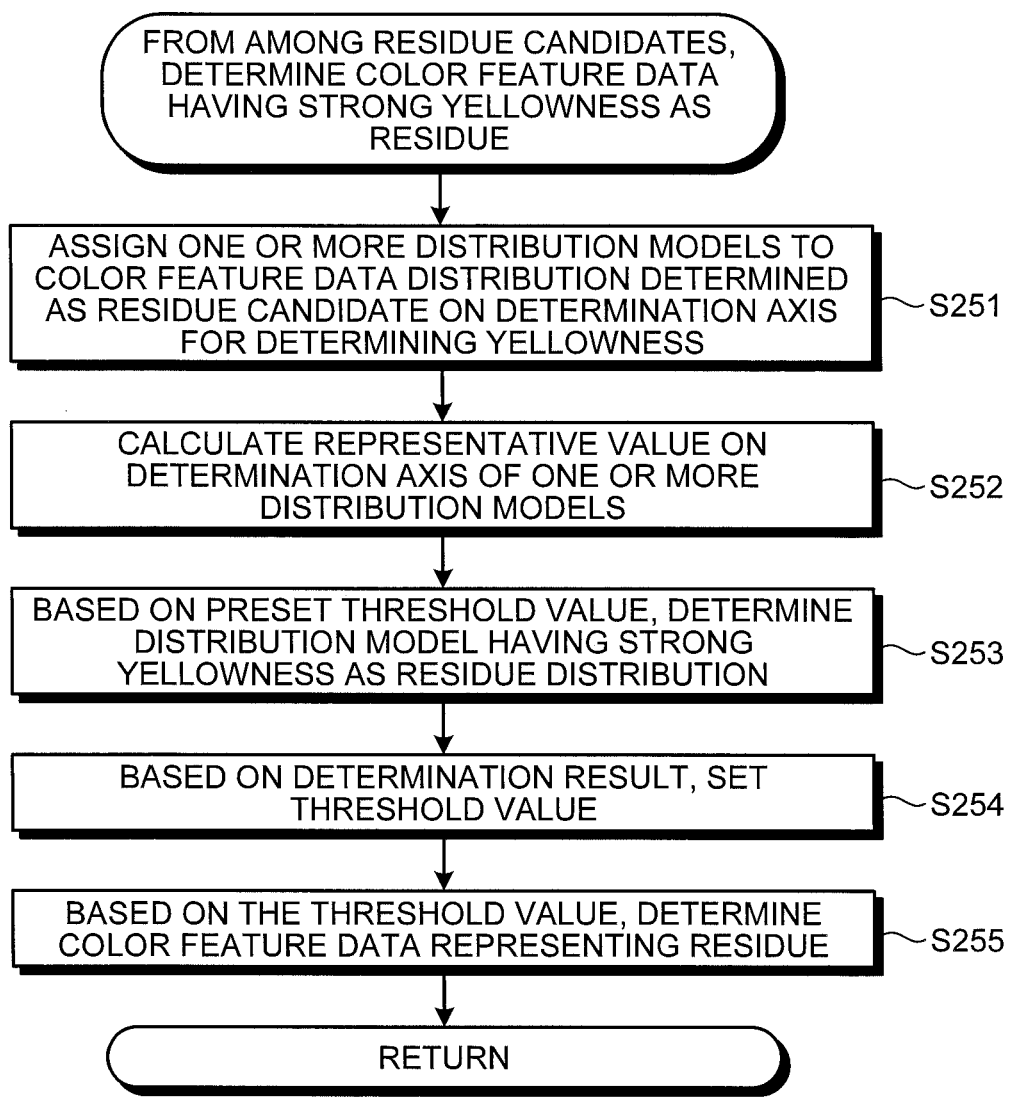
FIG. 39 is a flow chart illustrating operations of a residue distribution determination unit illustrated in FIG. 19.

At step S25 subsequent to step S24 (see FIG. 22), the residue distribution determination unit 240 determines the color feature data strong in yellowness, from among the color feature data determined to be the residue candidate, to be a residue. FIG. 39 is a flow chart illustrating operations of the residue distribution determination unit 240.

First, at step S251, the distribution model assignment unit 241, generates one or more distribution models by assigning, on a determination axis for determining yellowness, a specified distribution model to the distribution of the color feature data determined to be the residue candidate. In the second embodiment, as the determination axis, a B/G axis, which becomes stronger in yellowness as "0" is approached, is set. Further, in the second embodiment, to the distribution of the color feature data determined to be the residue candidate, one normal distribution is or two normal distributions are assigned. Details of a process of assigning the normal distribution/distributions to the distribution of the color feature data are similar to those of step S241 (see FIG. 24).

Subsequently, at step S252, the representative value calculation unit 242a of the distribution model determination unit 242 calculates a representative value on a determination axis of the one or more distribution models generated by the distribution model assignment unit 241. In more detail, similarly to step S242 (see FIG. 24), the maximum value $g_{max}'$ and the minimum value $g_{min}'$ of the distribution range of the distribution model assigned to the distribution of the color feature data determined to be the residue candidate are calculated.

Subsequently, at step S253, the threshold value processing unit 242b determines, based on a threshold value preset on the determination axis, a distribution model strong in yellowness to be a residue distribution. On the determination axis, a residue threshold value Th(R') for determining presence or absence of a residue and a white region threshold value Th(W)(Th(W)>Th(R')) for determining presence or absence of a white region such as a halation region or discolored lesion are set beforehand.

Figure 40:
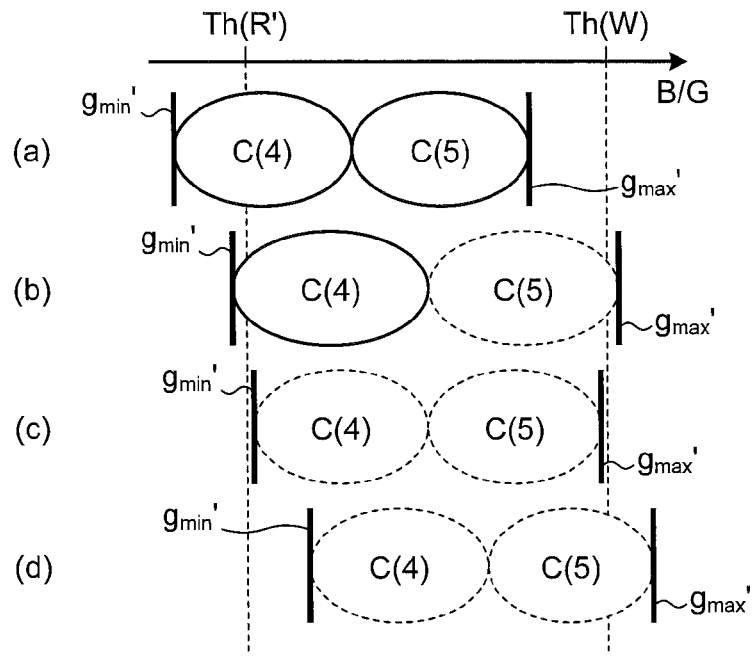
FIG. 40 is a schematic diagram illustrating a method of determining a residue distribution for clusters of color feature data.
Figure 41:
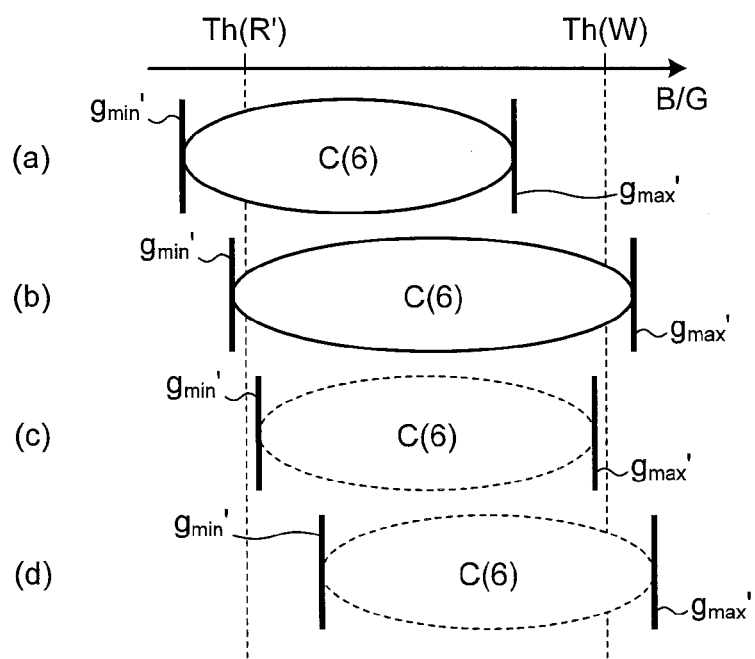
FIG. 41 is a schematic diagram illustrating the method of determining a residue distribution for a cluster of color feature data.

FIG. 40 and FIG. 41 illustrate clusters generated by clustering the color feature data that are residue candidates, based on the one or more distribution models generated in step S251. Of these, FIG. 40 illustrates two clusters C(4) and C(5) corresponding to a case in which two distribution models are assigned to the distribution of the color feature data, and the cluster smaller in the color feature data (B/G) is defined as the cluster C(4) and the cluster larger in the color feature data is defined as the cluster C(5). On the contrary, FIG. 41 illustrates a cluster C(6) corresponding to a case in which when two distribution models are assigned to the distribution of the color feature data, one of the distributions is included in the other one of the distributions. Hereinafter, as an example of a distribution model, a method of determining whether or not these clusters C(4) to C(6) are residue distributions (residue clusters) is described.

As illustrated in FIG. 40(a), if a maximum value $g_{max}'$ of a distribution range of the distribution models (that is, a maximum value of color feature data in the clusters, hereinafter, referred to as "maximum value of clusters") is smaller than the white region threshold value Th(W) ($g_{max}$'<Th(W)) and a minimum value $g_{min}$' of the distribution range of the distribution models (that is, a minimum value of the color feature data in the clusters, hereinafter referred to as "minimum value of the clusters") is equal to or less than the residue threshold value Th(R') ($g_{min}$'≤Th(R')), the threshold value processing unit 242b determines both of the clusters C(4) and C(5) to be residue distributions.

As illustrated in FIG. 40(b), if the maximum value $g_{max}$' of the clusters is equal to or greater than the white region threshold value Th(W) ($g_{max}$'≥Th(W)), and the minimum value $g_{min}$' of the clusters is equal to or less than the residue threshold value Th(R') ($g_{min}$'≤Th(R')), the threshold value processing unit 242b determines the cluster C(4) to be a residue distribution, and the cluster C(5) to be a white region distribution.

As illustrated in FIG. 40(c), if the maximum value $g_{max}$' of the clusters is less than the white region threshold value Th(W) ($g_{max}$'<Th(W)), and the minimum value $g_{min}$' of the clusters is greater than the residue threshold value Th(R') ($g_{min}$'>Th(R')), the threshold value processing unit 242b determines both of the clusters C(4) and C(5) to be white region distributions.

As illustrated in FIG. 40(d), if the maximum value $g_{max}$' of the clusters is equal to or greater than the white region threshold value Th(W) ($g_{max}$'≥Th(W)), and the minimum value $g_{min}$' of the clusters is greater than the residue threshold value Th(R') ($g_{min}$'>Th(R')), the threshold value processing unit 242b determines both of the clusters C(4) and C(5) to be white region distributions.

Further, as illustrated in FIG. 41(a), if the maximum value $g_{max}$' of the cluster is less than the white region threshold value Th(W) ($g_{max}$'<Th(W)), and the minimum value $g_{min}$' of the cluster is equal to or less than the residue threshold value Th(R') ($g_{min}$'≤Th(R')), the threshold value processing unit 242b determines the cluster C(6) to be a residue distribution.

As illustrated in FIG. 41(b), if the maximum value $g_{max}$' of the cluster is equal to or greater than the white region threshold value Th(W) ($g_{max}$'≥Th (W)), and the minimum value $g_{min}$' of the cluster is equal to or less than the residue threshold value Th(R') ($g_{min}$'≤Th(R')), the threshold value processing unit 242b determines the cluster C(6) to be a residue distribution.

As illustrated in FIG. 41(c), if the maximum value $g_{max}$' of the cluster is less than the white region threshold value Th(W) ($g_{max}$'<Th(W)), and the minimum value $g_{min}$' of the cluster is greater than the residue threshold value Th(R') ($g_{min}$'>Th (R')), the threshold value processing unit 242b determines the cluster C(6) to be a white region distribution.

As illustrated in FIG. 41(d), if the maximum value $g_{max}$' of the cluster is equal to or greater than the white region threshold value Th(W) ($g_{max}$'≥Th(W)), and the minimum value $g_{min}$' of the cluster is greater than the residue threshold value Th(R') ($g_{min}$'>Th(R')), the threshold value processing unit 242b determines the cluster C(6) to be a white region distribution.

Subsequently, at step S254, the threshold value setting unit 243 sets, based on a result of the determination in step S253, a threshold value determining color feature data representing a residue. In more detail, if determination results different from one another among the plurality of clusters are obtained, the inter-distribution-model threshold value setting unit 243a sets, as the threshold value, a value among the plurality of clusters on the determination axis (B/G axis). On the contrary, if determination results identical to one another among the plurality of clusters are obtained, the out-of-distribution-model threshold value setting unit 243b sets, as the threshold value, a value outside the clusters on the determination axis.

Figure 42:
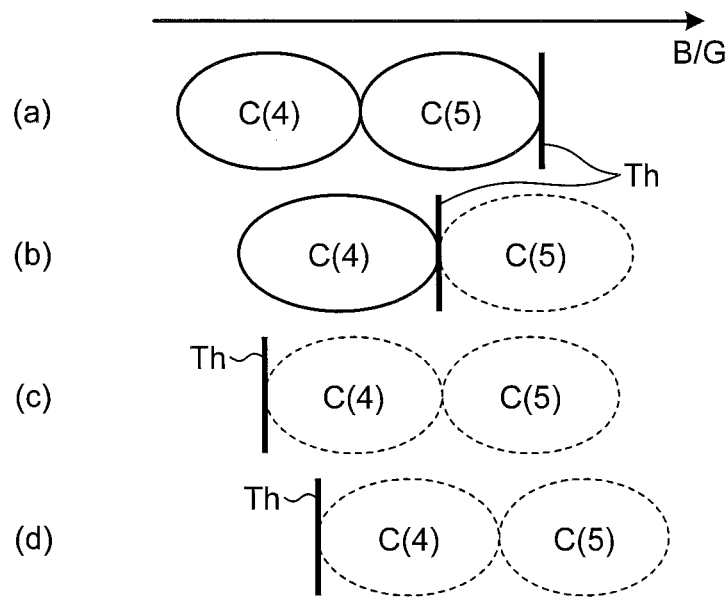
FIG. 42 is a schematic diagram illustrating a method of setting a threshold value that determines color feature data representing a residue.

Specifically, as illustrated in FIG. 40(a), if the two clusters C(4) and C(5) are both determined to be the residue distributions, the out-of-distribution-model threshold value setting unit 243b sets, as illustrated in FIG. 42(a), the maximum value $g_{max}$', which is a value outside the clusters C(4) and C(5) and on a side weak in yellowness of the determination axis (on a side large in B/G value), as the threshold value Th.

Further, as illustrated in FIG. 40(b), if the cluster C(4) is determined to be the residue distribution and the cluster C(5) is determined to be the white region distribution, the inter-distribution-model threshold value setting unit 243a sets, as illustrated in FIG. 42(b), color feature data of a boundary position between the clusters C(4) and C(5) on the determination axis (that is, a value at the boundary position between the normal distributions $f_1$ and $f_2$ (see FIG. 29)) as the threshold value Th.

Further, as illustrated in FIGS. 40(c) and (d), if the two clusters C(4) and C(5) are both determined to be the white region distributions, the out-of-distribution-model threshold value setting unit 243b sets, as illustrated in FIGS. 42(c) and (d), the minimum value $g_{min}$', which is a value outside the clusters C(4) and C(5) and on a side strong in yellowness on the determination axis (side small in B/G value), as the threshold value Th.

On the contrary, if the determination for one cluster is made in step S253, the threshold value setting unit 243 sets the candidate threshold value as described below.

Figure 43:
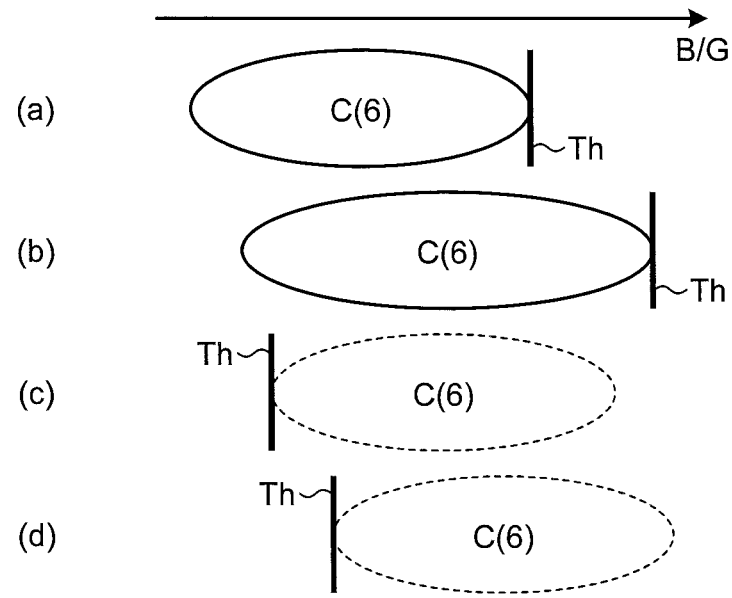
FIG. 43 is a schematic diagram illustrating the method of setting a threshold value that determines color feature data representing a residue.

That is, as illustrated in FIGS. 41(a) and (b), if the cluster C(6) is determined to be the residue distribution, the out-of-distribution-model threshold value setting unit 243b sets, as illustrated in FIGS. 43(a) and (b), the maximum value $g_{max}$', which is a value weak in yellowness on the determination axis (side large in B/G value), as the threshold value Th.

Further, as illustrated in FIGS. 41(c) and (d), if the cluster C(6) is determined to be the white region distribution, the out-of-distribution-model threshold value setting unit 243b sets, as illustrated in FIGS. 43(c) and (d), the minimum value $g_{min}$', which is a value on a side strong in yellowness on the determination axis (side small in B/G value), as the threshold value Th.

Subsequently, at step S255, the determination unit 244 determines, based on the threshold value Th, the color feature data representing the residue. Specifically, the determination unit 244 determines, on the determination axis, any color feature data present on a side stronger in yellowness than the threshold value Th (that is, smaller in B/G value) to represent a residue, and any color feature data present on a side weaker in yellowness than the threshold value Th (that is, larger in B/G value) to represent a white region.

The determination unit 244 may perform the above determination for each cluster generated by clustering the color feature data determined to be the residue candidate. In this case, a centroid position of each cluster is calculated, any cluster having a centroid position present on a side stronger in yellowness than the threshold value Th is determined to be a residue distribution, and any cluster present on a side weaker in yellowness than the threshold value Th is determined to be the white region. Thereafter, the operations of the computation unit 200 return to the main routine.

At step S26 subsequent to step S25 (see FIG. 22), the computation unit 200 outputs a result of the determination in step S24. Accordingly, the control unit 10 causes the recording unit 50 to record therein the result of the determination and the display unit 40 to display the result of the determination.

As described above, according to the second embodiment, even if distributions of color feature data in intraluminal images vary, based on the candidate threshold value Th (N) and threshold value Th, which are references adaptively set, residue regions are able to be determined accurately.

If a processing unit that distinguishes a residue region from an intraluminal image based on a frequency distribution of color feature data is installed in an actual image processing apparatus, any color feature data of a frequency equal to or less than a specified value may be removed as a noise. If a threshold value for removing the noise is not appropriate, results of determination sometimes differ greatly among intraluminal images, which have been captured one after the other within a time series and thus are supposed to have not much change in the subject.

However, in the second embodiment, by assigning a specified distribution model (for example, a normal distribution) to a distribution of color feature data, the distribution of the color feature data is separated into a main distribution and a distribution other than the main distribution, and according to a result of determination of a residue candidate distribution with respect to the distribution model, a threshold value for determining a residue candidate is adaptively set by using a representative value of the distribution model (a maximum value, a minimum value, or a value at a boundary position). Further, a threshold value for determining a residue region is determined similarly. Therefore, according to the second embodiment, more highly accurate distinction of a residue region is possible than conventionally.

Modified Example 2-1

Next, a modified example 2-1 of the second embodiment will be described.

Figure 44:
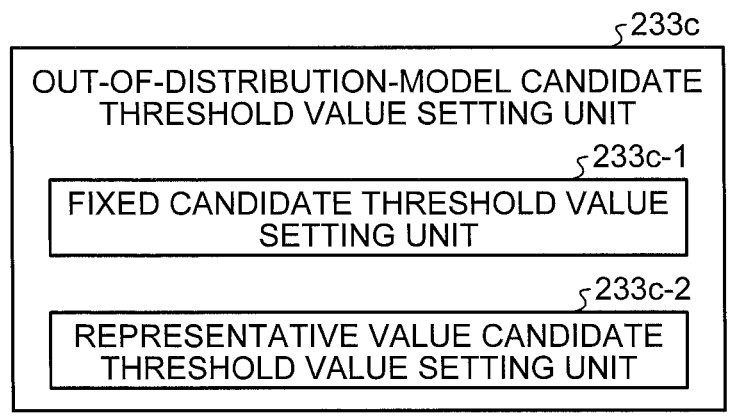
FIG. 44 is a block diagram illustrating a configuration of an out-of-distribution-model candidate threshold value setting unit in a modified example 2-1.
Figure 45:
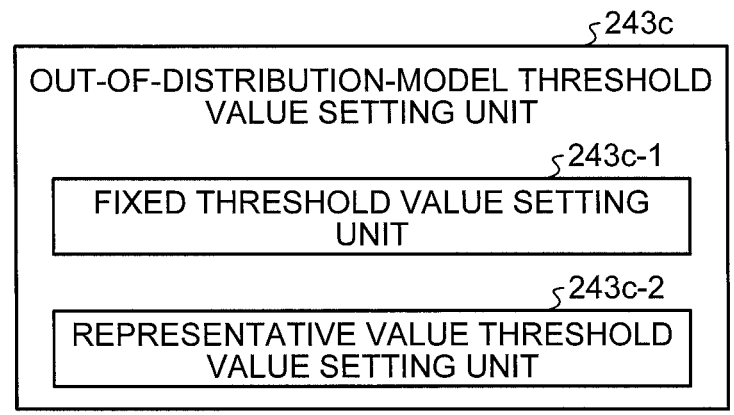
FIG. 45 is a block diagram illustrating a configuration of an out-of-distribution-model threshold value setting unit in the modified example 2-1.
Figure 46:
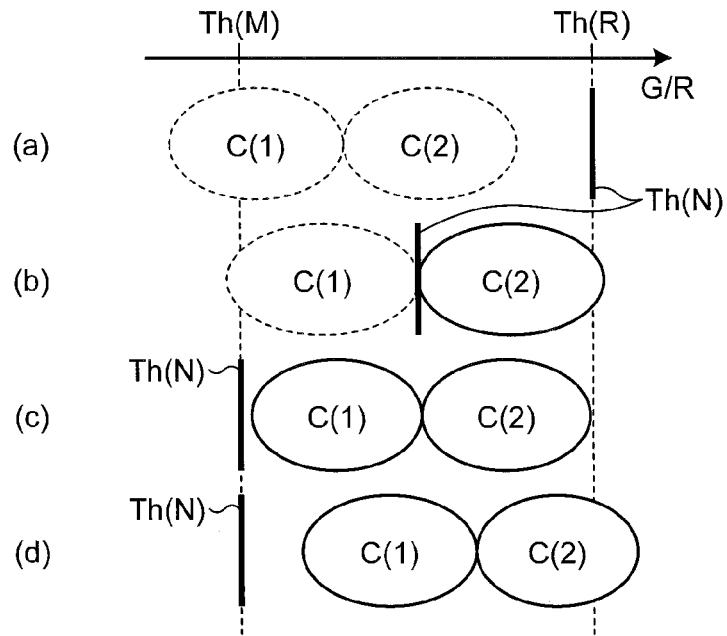
FIG. 46 is a block diagram illustrating operations of an out-of-distribution-model candidate threshold value setting unit illustrated in FIG. 44.
Figure 47:
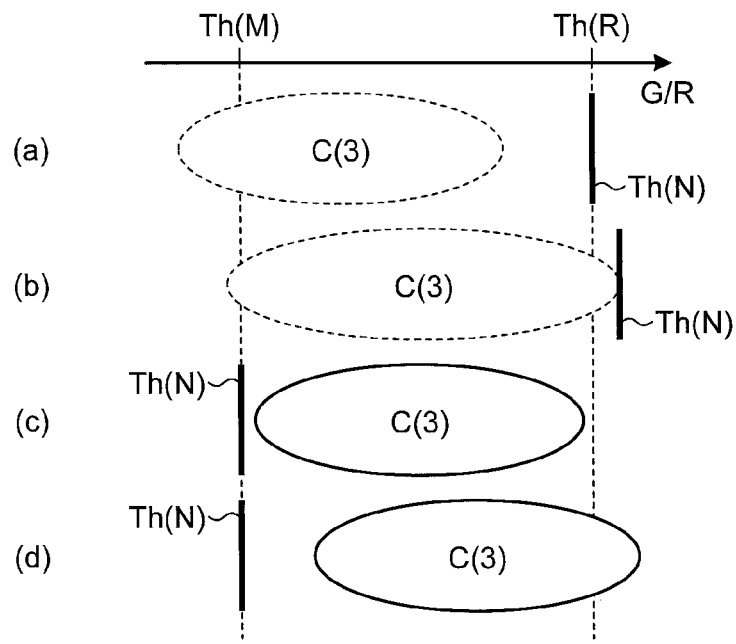
FIG. 47 is a schematic diagram illustrating the operations of the out-of-distribution-model candidate threshold value setting unit illustrated in FIG. 44.
Figure 48:
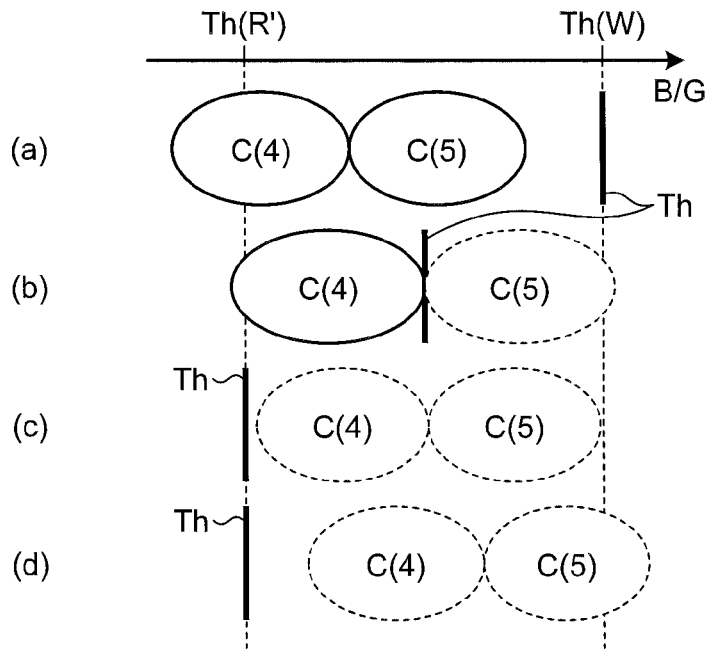
FIG. 48 is a schematic diagram illustrating the operations of the out-of-distribution-model candidate threshold value setting unit illustrated in FIG. 44.
Figure 49:
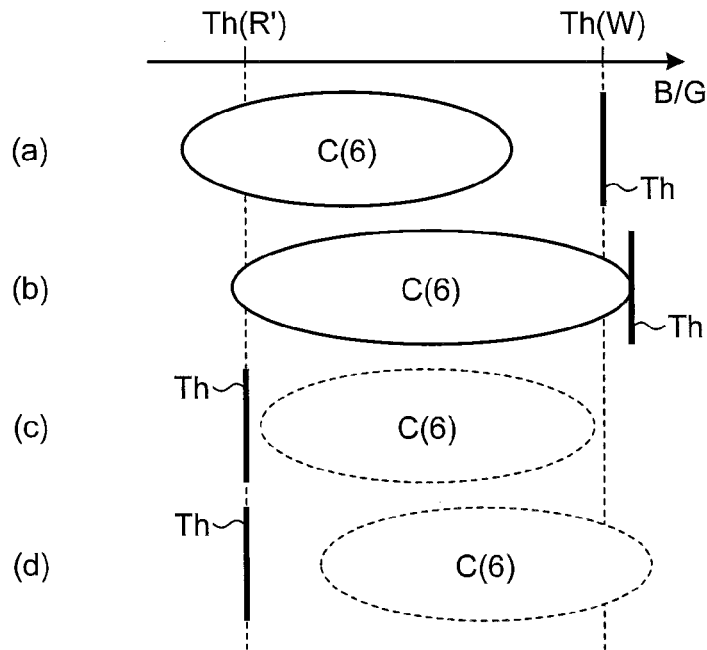
FIG. 49 is a schematic diagram illustrating the operations of the out-of-distribution-model candidate threshold value setting unit illustrated in FIG. 44.

An image processing apparatus according to the modified example 2-1 includes an out-of-distribution-model candidate threshold value setting unit 233c illustrated in FIG. 44 and an out-of-distribution-model threshold value setting unit 243c illustrated in FIG. 45, instead of the out-of-distribution-model candidate threshold value setting unit 233b and the out-of-distribution-model threshold value setting unit 243b of the image processing apparatus 2 illustrated in FIG. 19. Of the image processing apparatus according to the modified example 2-1, a configuration and operations of each unit other than the out-of-distribution-model candidate threshold value setting unit 233c and the out-of-distribution-model threshold value setting unit 243c are similar to those of the second embodiment.

As illustrated in FIG. 44, the out-of-distribution-model candidate threshold value setting unit 233c includes a fixed candidate threshold value setting unit 233c-1 and a representative value candidate threshold value setting unit 233c-2. The fixed candidate threshold value setting unit 233c-1 sets a fixed value defined beforehand on a candidate determination axis as a candidate threshold value. The representative value candidate threshold value setting unit 233c-2 sets a representative value of one or more distribution models as a candidate threshold value. Either one of these units operates according to a distribution range of the one or more distribution models.

As illustrated in FIG. 45, the out-of-distribution-model threshold value setting unit 243c includes a fixed threshold value setting unit 243c-1 and a representative value threshold value setting unit 243c-2. The fixed threshold value setting unit 243c-1 sets a fixed value defined beforehand on a determination axis as a threshold value. The representative value threshold value setting unit 243c-2 sets a representative value of the one or more distribution models as a threshold value. Either one of these units operates according to a distribution range of the one or more distribution models.

Hereinafter, specific operations of the out-of-distribution-model candidate threshold value setting unit 233c and out-of-distribution-model threshold value setting unit 243c are described with reference to FIG. 35, FIG. 36, FIG. 40, FIG. 41, and FIG. 46 to FIG. 49.

As illustrated in FIG. 35(a) and FIG. 36(a), if the maximum value $g_{max}$ of the clusters C(2) and C(3) is less than the residue candidate threshold value Th(R), the fixed candidate threshold value setting unit 233c-1 sets the threshold value Th(R) as the candidate threshold value Th(R) as illustrated in FIG. 46(a) and FIG. 47(a).

Further, as illustrated in FIGS. 35(c) and (d), and FIGS. 36(c) and (d), if the minimum value $g_{min}$ of the clusters C(1) and C(3) is greater than the mucosa threshold value Th(M), the fixed candidate threshold value setting unit 233c-1 sets the threshold value Th(M) as the candidate threshold value Th(N) as illustrated in FIGS. 46(c) and (d), and FIGS. 47(c) and (d).

As illustrated in FIG. 36(b), if the minimum value $g_{min}$ of the cluster C(3) is equal to or less than the threshold value Th(M), and the maximum value $g_{max}$ thereof is equal to or greater than the threshold value Th(R), the representative value candidate threshold value setting unit 233c-2 sets, the maximum value $g_{max}$ of the cluster C(3) as the candidate threshold value Th(N).

As illustrated in FIG. 35(b), if the minimum value $g_{min}$ of the two clusters C(1) and C(2) is equal to or less than the threshold value Th(M), and the maximum value $g_{max}$ thereof is equal to or greater than the threshold value Th(R), similarly to the second embodiment, the inter-distribution-model candidate threshold value setting unit 233a sets the value at the boundary position between the two clusters C(1) and C(2) as the candidate threshold value Th(N) (see FIG. 46(b)).

As illustrated in FIG. 40(a) and FIG. 41(a), if the maximum value $g_{max}'$ of the clusters C(5) and C(6) corresponding to the one or more distribution models is less than the white region threshold value Th(W), the fixed threshold value setting unit 243c-1 sets, as illustrated in FIG. 48(a) and FIG. 49(a), the threshold value Th(W) as the threshold value Th.

Further, as illustrated in FIGS. 40(c) and (d), and FIG. 41(c) and (d), if the minimum value $g_{min}'$ of the clusters C(4) and C(6) is greater than the residue threshold value Th(R'), the fixed threshold value setting unit 243c-1 sets, as illustrated in FIGS. 48(c) and (d), and FIG. 49(c) and (d), a threshold value Th(R') as the threshold value Th.

As illustrated in FIG. 41(b), if the minimum value $g_{min}'$ of the cluster C(6) is equal to or less than the threshold value Th(R') and the maximum value $g_{max}'$ thereof is equal to or greater than the threshold value Th(W), the representative value threshold value setting unit 243c-2 sets the maximum value $g_{max}'$ of the cluster C(6) as the threshold value Th.

As illustrated in FIG. 40(b), if the minimum value $g_{min}'$ of the two clusters C(4) and C(5) is equal to or less than the threshold value Th(R'), and the maximum value $g_{max}'$ thereof is equal to or greater than the threshold value Th(W), similarly to second embodiment, the inter-distribution-model threshold value setting unit 243a sets the value at the boundary position between the two clusters C(4) and C(5) as the threshold value Th (see FIG. 48(b)).

Modified Example 2-2

Next, a modified example 2-2 of the second embodiment will be described.

Figure 50:
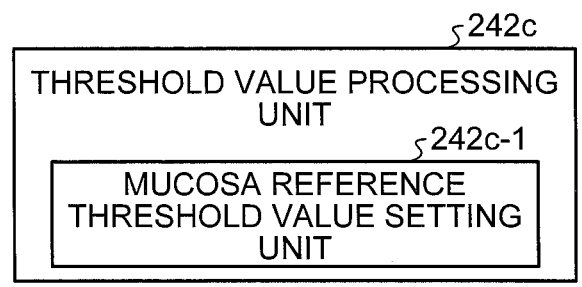
FIG. 50 is a block diagram illustrating a configuration of a threshold value processing unit in a modified example 2-2.

An image processing apparatus according to the modified example 2-2 includes a threshold value processing unit 242c illustrated in FIG. 50, instead of the threshold value processing unit 242c of the image processing apparatus 2 illustrated in FIG. 19. Of the image processing apparatus according to the modified example 2-2, a configuration and operations of each unit other than the threshold value processing unit 242c are similar to those of the second embodiment.

As illustrated in FIG. 50, the threshold value processing unit 242c includes a mucosa reference threshold value setting unit 242c-1 that assumes a distribution of color feature data not determined to be a residue candidate by the residue candidate distribution determination unit 230 as a mucosa distribution, and calculates a representative value of the mucosa distribution on a determination axis.

In more detail, the mucosa reference threshold value setting unit 242c-1 sets the distribution of the color feature data other than the distribution determined to be a residue candidate distribution by the residue candidate distribution determination unit 230 as the mucosa distribution. Thereafter, a centroid $g_M$ of the mucosa distribution on the determination axis (B/G axis) is calculated, and this is set as a representative value of the mucosa distribution.

Figure 51:
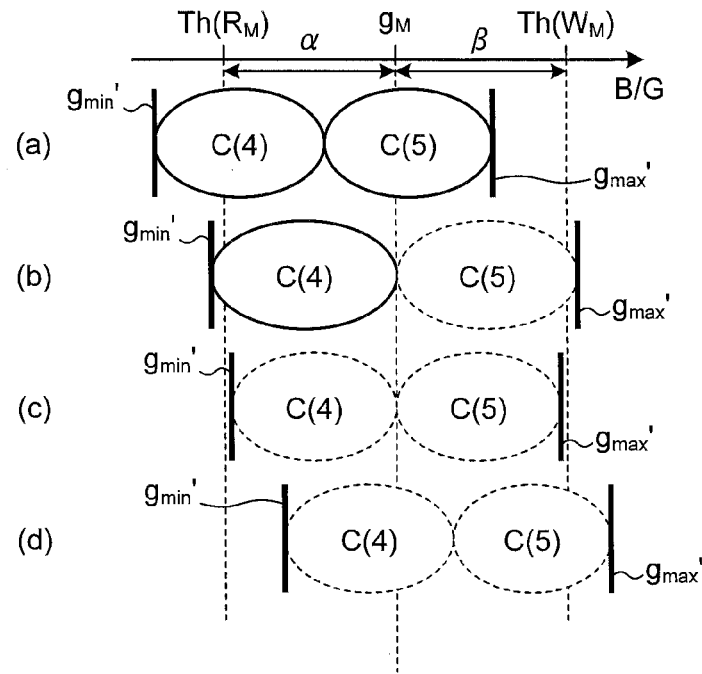
FIG. 51 is a schematic diagram illustrating a method of determining a residue distribution for clusters of color feature data in the modified example 2-2.
Figure 52:
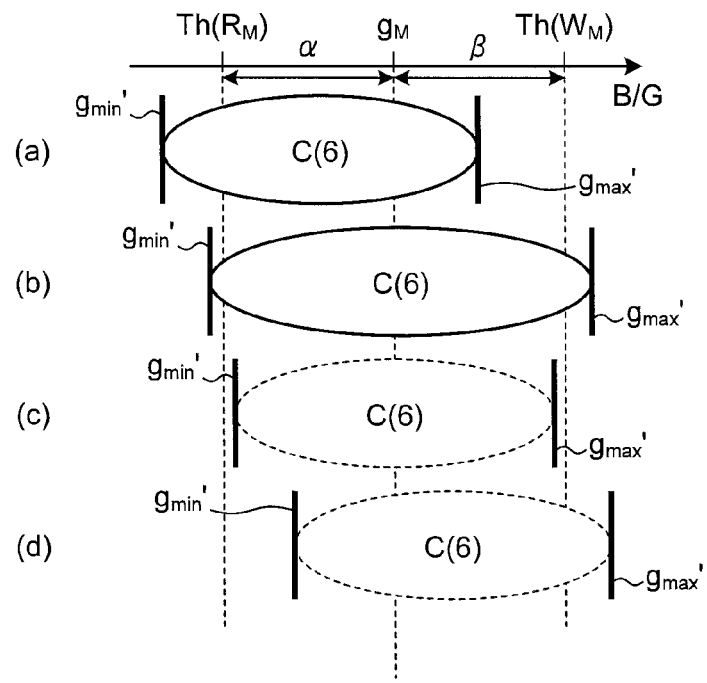
FIG. 52 is a schematic diagram illustrating the method of determining a residue distribution for clusters of color feature data in the modified example 2-2.

Subsequently, the mucosa reference threshold value setting unit 242c-1 sets, as illustrated in FIG. 51 and FIG. 52, on the determination axis, a residue threshold value $Th(R_M)$ for determining presence or absence of a residue and a white region threshold value $Th(W_M)$ for determining a white region, with reference to a centroid $g_M$ of the mucosa distribution. Of these, the residue threshold value $Th(R_M)$ is calculated by subtracting, from the centroid $g_M$, a specified value $\alpha$ obtained from teacher data. The threshold value $Th(W_M)$ is calculated by adding, to the centroid $g_M$, a specified value $\beta$ obtained from teacher data.

The threshold value processing unit 242c determines whether a distribution of respective color feature data is a residue or a white region, based on the residue threshold value $Th(R_M)$ and the white region threshold value $Th(W_M)$, which have been set as described above. Specifically, as illustrated in FIG. 51(*a*), if the maximum value $g_{max}'$ of the clusters is less than the white region threshold value $Th(W_M)$ ($g_{max}'<Th(W_M)$), and the minimum value $g_{min}'$ of the clusters is equal to or less than the residue threshold value $Th(R_M)$ ($g_{min}'\leq Th(R_M)$), the threshold value processing unit 242c determines both of the clusters C(4) and C(5) to be residue distributions.

As illustrated in FIG. 51(*b*), if the maximum value $g_{max}'$ of the clusters is equal to or greater than the white region threshold value $Th(W_M)$ ($g_{max}'\geq Th(W_M)$), and the minimum value $g_{min}'$ of the clusters is equal to or less than the residue threshold value $Th(R_M)$ ($g_{min}'\leq Th(R_M)$), the threshold value processing unit 242c determines the cluster C(4) to be a residue distribution and the cluster C(5) to be a white region.

As illustrated in FIG. 51(*c*), if the maximum value $g_{max}'$ of the clusters is less than the white region threshold value $Th(W_M)$ ($g_{max}'<Th(W_M)$), and the minimum value $g_{min}'$ of the clusters is greater than the residue threshold value $Th(R_M)$ ($g_{min}'>Th(R_M)$), the threshold value processing unit 242c determines both of the clusters C(4) and C(5) to be white regions.

As illustrated in FIG. 51(*d*), if the maximum value $g_{max}'$ of the clusters is equal to or greater than the white region threshold value $Th(W_M)$ ($g_{max}'\geq Th(W_M)$), and the minimum value $g_{min}$ of the clusters is greater than the residue threshold value $Th(R_M)$ ($g_{min}'>Th(R_M)$), the threshold value processing unit 242c determines both of the clusters C(4) and C(5) to be white regions.

Further, as illustrated in FIG. 52(*a*), if the maximum value $g_{max}'$ of the cluster is less than the white region threshold value $Th(W_M)$ ($g_{max}'<Th(W_M)$), and the minimum value $g_{min}'$ of the cluster is equal to or less than the residue threshold value $Th(R_M)$ ($g_{min}'\leq Th(R_M)$), the threshold value processing unit 242c determines the cluster C(6) to be a residue distribution.

As illustrated in FIG. 52(*b*), if the maximum value $g_{max}'$ of the cluster is equal to or greater than the white region threshold value $Th(W_M)$ ($g_{max}'\geq Th(W_M)$), and the minimum value $g_{min}'$ of the cluster is equal to or less than the residue threshold value $Th(R_M)$ ($g_{min}'\leq Th(R_M)$), the threshold value processing unit 242c determines the cluster C(6) to be a residue distribution.

As illustrated in FIG. 52(*c*), if the maximum value $g_{max}'$ of the cluster is less than the white region threshold value $Th(W_M)$ ($g_{max}'<Th(W_M)$), and the minimum value $g_{min}'$ of the cluster is greater than the residue threshold value $Th(R_M)$ ($g_{min}'>Th(R_M)$), the threshold value processing unit 242c determines cluster C(6) to be a white region.

As illustrated in FIG. 52(*d*), if the maximum value $g_{max}'$ of the cluster is equal to or greater than the white region threshold value $Th(W_M)$ ($g_{max}'\ Th(W_M)$), and the minimum value $g_{min}'$ of the cluster is greater than the residue threshold value $Th(R_M)$ ($g_{min}'>Th(R_M)$), the threshold value processing unit 242c determines the cluster C(6) to be a white region.

This modified example 2-2 may be implemented independently, or in combination with the process executed by the threshold value processing unit 242b of the second embodiment. In the latter case, as illustrated in FIG. 40(*c*) and FIG. 41(*b*), if the maximum value $g_{max}'$ of the color feature data is less than the threshold value $Th(W)$, and the minimum value $g_{min}'$ of the clusters/cluster is greater than the threshold value $Th(R')$, the determination is preferably performed again by using the threshold values $Th(W_M)$ and $Th(R_M)$ that are set in the modified example 2-2.

Third Embodiment

Next, a third embodiment of the present invention will be described.

Figure 53:
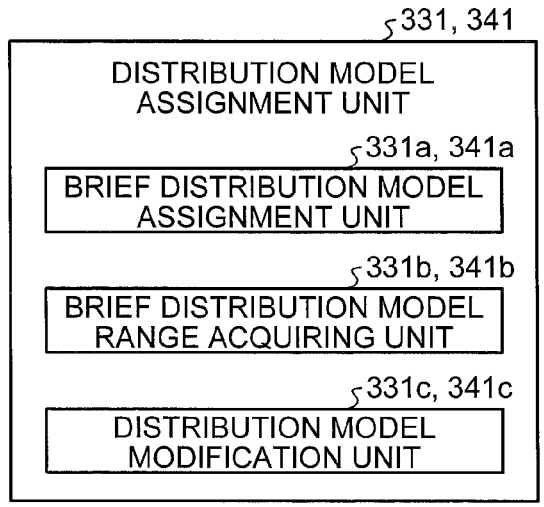
FIG. 53 is a block diagram illustrating a configuration of a distribution model assignment unit included in an image processing apparatus according to a third embodiment of the present invention.

An image processing apparatus according to the third embodiment includes distribution model assignment units 331 and 341 illustrated in FIG. 53, instead of the distribution model assignment units 231 and 241 of the image processing apparatus 2 illustrated in FIG. 19, respectively. Of the image processing apparatus according to the third embodiment, a configuration and operations of each unit other than the distribution model assignment units 331 and 341 are similar to those of the second embodiment.

As illustrated in FIG. 53, the distribution model assignment units 331 and 341 respectively include brief distribution model assignment units 331a and 341a, brief distribution model range acquiring units 331b and 341b, and distribution model modification units 331c and 341c.

Of these, the brief distribution model assignment unit 331a assigns, on a candidate determination axis (for example, G/R axis) of color feature data determining redness, distribution models (hereinafter, referred to as "brief distribution models") fewer than distribution models assignable to the distribution of the color feature data in the intraluminal image. The brief distribution model range acquiring unit 331b acquires a distribution range of the brief distribution models on the candidate determination axis. The distribution model modification unit 331c assigns, in the distribution range of the brief distribution models, one or more distribution models to the distribution of the color feature data.

Further, the brief distribution model assignment unit 341a assigns, on a determination axis (for example, B/G axis) of color feature data determining yellowness, distribution models (hereinafter, referred to as "brief distribution models") fewer than distribution models assignable to the distribution of the color feature data determined to be a residue candidate. The brief distribution model range acquiring unit 341b acquires a distribution range of a brief distribution model on the determination axis. The distribution model modification unit 341c assigns, in the distribution range of the brief distribution models, one or more distribution models to the distribution of the color feature data determined to be the residue candidate.

Next, operations of the image processing apparatus according to the third embodiment will be described. Operations of the image processing apparatus according to the third embodiment as a whole are similar to those illustrated in FIG. 22, FIG. 24, and FIG. 39, and detailed operations of step S241 illustrated in FIG. 24 and step S25 illustrated in FIG. 39 are different.

Figure 54:
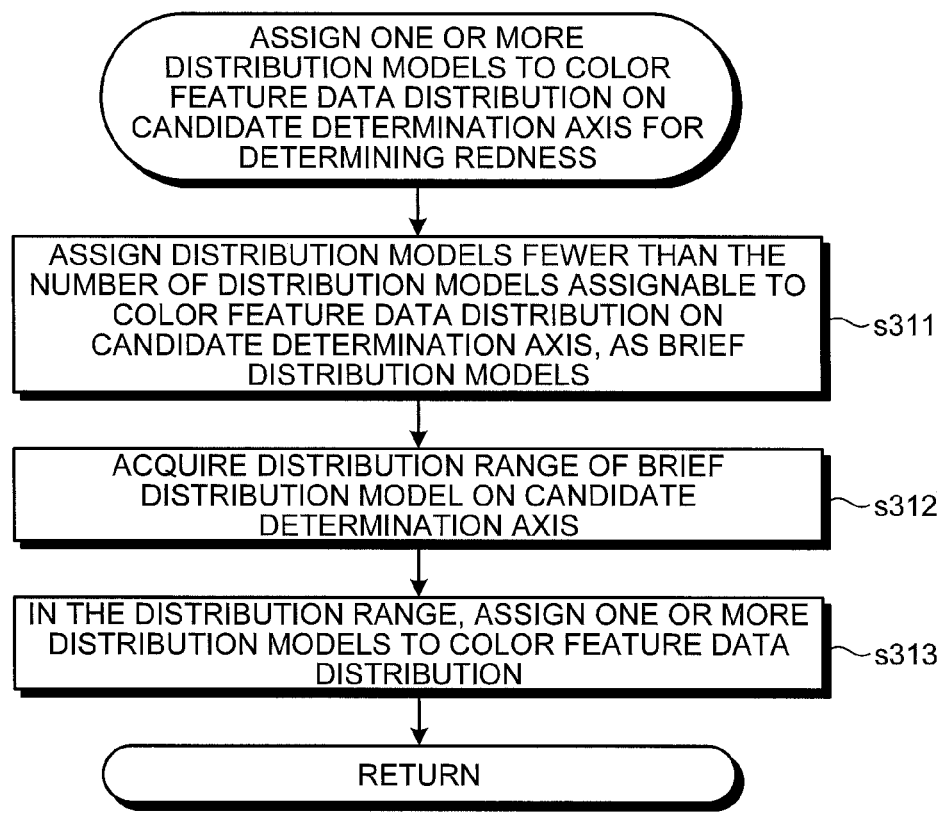
FIG. 54 is a flow chart illustrating operations of the distribution model assignment unit that performs assignment of a distribution model to a distribution of color feature data in an intraluminal image.
Figure 55:
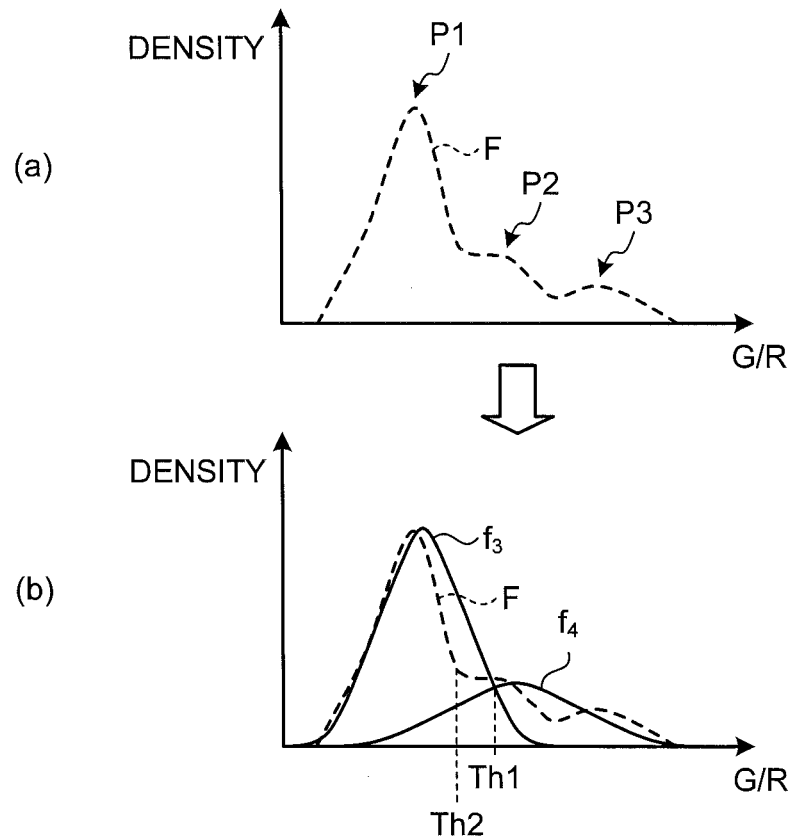
FIG. 55 is a schematic diagram illustrating the operations of the distribution model assignment unit illustrated in FIG. 53.

FIG. 54 is a flow chart illustrating operations of the distribution model assignment unit 331 that performs assignment of a distribution model to a distribution of color feature data in an intraluminal image at step S241 illustrated in FIG. 24. Further, FIG. 55 to FIG. 58 are schematic diagrams illustrating the operations of the distribution model assignment unit 331.

Figure 56:
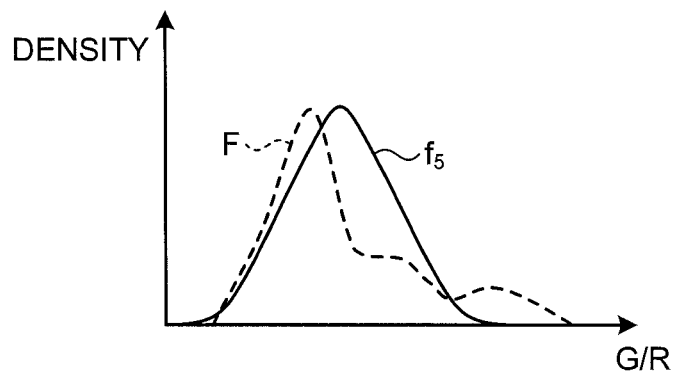
FIG. 56 is a schematic diagram illustrating the operations of the distribution model assignment unit illustrated in FIG. 53.

First, at step s311, the brief distribution model assignment unit 331a, assigns, on the candidate determination axis (G/R axis), distribution models fewer than the number of distribution models assignable to the distribution of the color feature data, as brief distribution models. For example, as illustrated in FIG. 55(a), if two normal distributions $f_3$ and $f_4$ are assignable to a density function "F" corresponding to the distribution of the color feature data, as illustrated in FIG. 56, one normal distribution $f_5$ is assigned as a brief distribution model to the density function "F". The assignment of the normal distribution $f_5$ may be performed by using the EM algorithm described in the second embodiment, for example.

Figure 57:
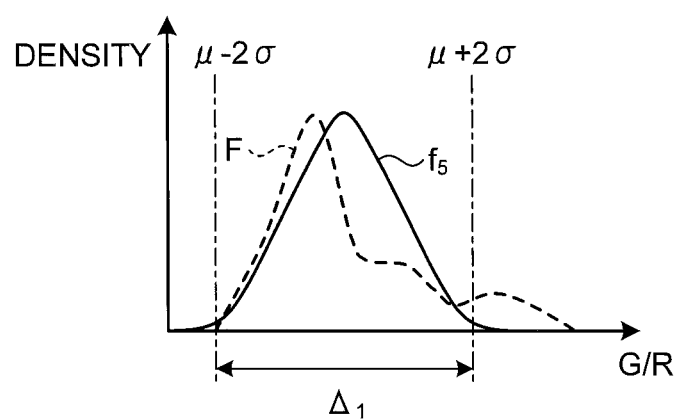
FIG. 57 is a schematic diagram illustrating the operations of the distribution model assignment unit illustrated in FIG. 53.

Subsequently, at step s312, the brief distribution model range acquiring unit 331b acquires a distribution range of the brief distribution models on the candidate determination axis. Specifically, as illustrated in FIG. 57, an average μ and a variance $\sigma^2$, which are parameters of the normal distribution $f_5$, are acquired, and a range of $\mu \pm 2\sigma$ including 95.7% of the color feature data is taken as a distribution rage $\Delta_1$ of the brief distribution model.

Figure 58:
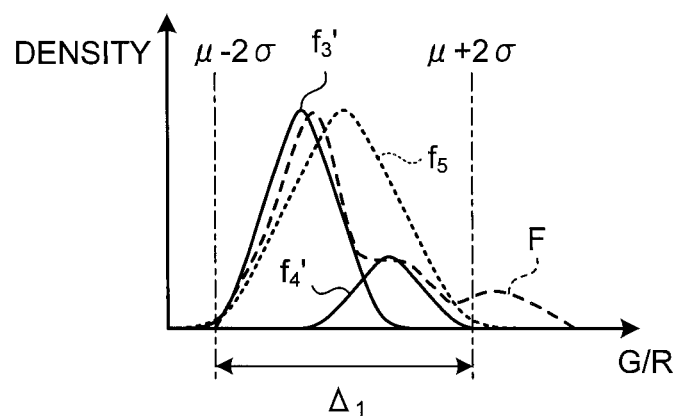
FIG. 58 is a schematic diagram illustrating the operations of the distribution model assignment unit illustrated in FIG. 53.

Subsequently, at step s313, the distribution model modification unit 331c assigns, in the distribution range of the brief distribution model, one or more distribution models to the distribution of the color feature data. Specifically, as illustrated in FIG. 58, to a distribution of color feature data in the distribution range $\Delta_1$, two normal distributions $f_3'$ and $f_4'$ are assigned by an EM algorithm, for example. Thereafter, the operations return to the main routine.

Figure 59:
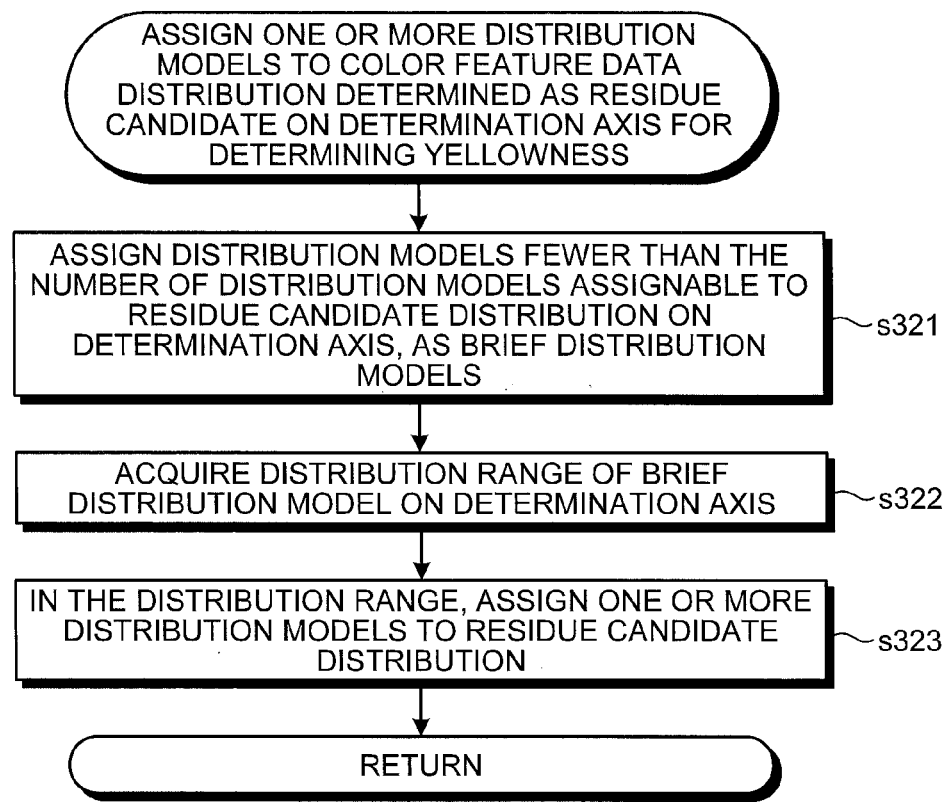
FIG. 59 is a flow chart illustrating the operations of the distribution model assignment unit that performs assignment of a distribution model to a distribution of color feature data determined to be a residue candidate.

FIG. 59 is a flow chart illustrating operations of the distribution model assignment unit 341 that performs assignment of a distribution model to the distribution of the color feature data determined to be the residue candidate at step S251 illustrated in FIG. 39. Hereinafter, while assuming the candidate determination axis (G/R axis) illustrated in FIG. 56 to FIG. 58 to be replaced by a determination axis (B/G axis), description is made with reference to these drawings.

First, at step s321, the brief distribution model assignment unit 341a assigns, on the determination axis (B/G axis), distribution models fewer than the number of distribution models assignable to the distribution of the color feature data determined to be the residue candidate, as brief distribution models. For example, as illustrated in FIG. 56, to a density function "F" corresponding to the distribution of the color feature data determined to be the residue candidate, if two normal distributions are assignable, one normal distribution $f_5$ is assigned.

Subsequently, at step s322, the brief distribution model range acquiring unit 341b acquires a distribution range of the brief distribution models on the determination axis. For example, as illustrated in FIG. 57, the average μ and variance $\sigma^2$, which are parameters of the normal distribution $f_5$, are obtained, and the range of $\mu \pm 2\sigma$ is taken as the distribution range $\Delta_1$ of the brief distribution model.

Subsequently, at step s323, the distribution model modification unit 341c assigns, in the distribution range $\Delta_1$ of the brief distribution model, one or more distribution models to the distribution of the color feature data determined to be the residue candidate. For example, as illustrated in FIG. 58, two normal distributions $f_3'$ and $f_4'$ are assigned to the distribution of the color feature data in the distribution range $\Delta_1$. Thereafter, the operations return to the main routine.

According to the third embodiment described above, even if a plurality of peaks are present in a distribution of color feature data, a distribution model is assignable appropriately. Therefore, accurate identification of a residue region becomes possible.

In an EM algorithm, sometimes a local solution is yielded by becoming dependent on initial values. Therefore, as illustrated in FIG. 55(a) for example, if the two normal distributions $f_3$ and $f_4$ are attempted to be assigned to the density function "F" in which three peaks P1 to P3 are present as illustrated in FIG. 55(b), there is a risk that a boundary Th1 between the normal distributions $f_3$ and $f_4$ deviates from a boundary Th2 of the plurality of distributions included in the actual distribution of the color feature data. In this case, appropriately setting a candidate threshold value (or threshold value) at a later stage becomes impossible.

Thus, in the third embodiment, a stepwise process is performed, in which, after assigning one normal distribution $f_5$ to the density function "F", the two normal distributions $f_3'$ and $f_4'$ are assigned while being limited to the distribution range $\Delta_1$ of the normal distribution $f_5$. Thereby, the boundary Th2' that matches more to the actual distribution of the color feature data is obtainable, and an appropriate candidate threshold value (or threshold value) is settable.

Fourth Embodiment

Next, a fourth embodiment of the present invention will be described.

Figure 60:
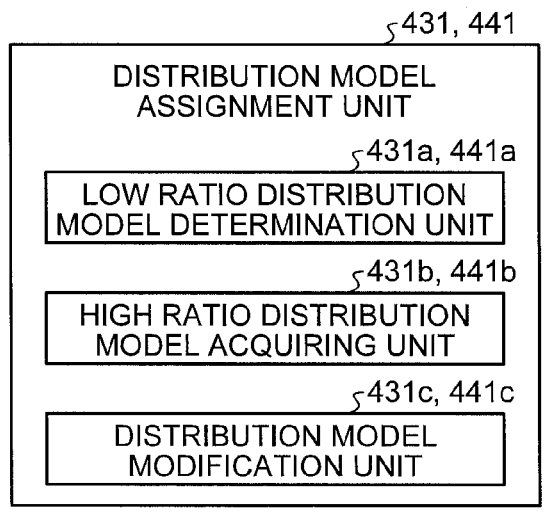
FIG. 60 is a block diagram illustrating a configuration of a distribution model assignment unit included in an image processing apparatus according to a fourth embodiment of the present invention.

An image processing apparatus according to the fourth embodiment includes distribution model assignment units 431 and 441 illustrated in FIG. 60, instead of the distribution model assignment units 231 and 241 of the image processing apparatus 2 illustrated in FIG. 19, respectively. Of the image processing apparatus according to the fourth embodiment, a configuration and operations of each unit other than the distribution model assignment units 431 and 441 are similar to those of the second embodiment.

As illustrated in FIG. 60, the distribution model assignment units 431 and 441 respectively include a low ratio distribution model determination units 431a and 441a, a high ratio distribution model acquiring units 431*b* and 441*b*, and distribution model modification units 431*c* and 441*c*.

Of these, the low ratio distribution model determination unit 431*a* determines, on a candidate determination axis (for example, G/R axis) of color feature data determining redness, whether or not in one or more distribution models assigned to a distribution of color feature data in an intraluminal image, a low ratio distribution model, which has a mixing ratio among the one or more distribution models equal to or less than a specified value, is included. If a low ratio distribution model is included in the one or more distribution models, the high ratio distribution model acquiring unit 431*b* acquires a distribution range on the candidate determination axis over which a distribution model remaining after the exclusion of the low ratio distribution model is distributed. The distribution model modification unit 431*c* performs assignment of one or more distribution models again, to the distribution of the color feature data, in the distribution range acquired by the high ratio distribution model acquiring unit 431*b*.

Further, the low ratio distribution model determination unit 441*a* determines, on a determination axis (for example, B/G axis) of color feature data determining yellowness, whether or not, in the one or more distribution models assigned to the distribution of the color feature data determined to be a residue candidate, a low ratio distribution model, which has a mixing ratio among the one or more distribution models equal to or less than a specified value, is included. If a low ratio distribution model is included in the one or more distribution models, the high ratio distribution model acquiring unit 441*b* acquires a distribution range on the determination axis over which a distribution model remaining after the exclusion of the low ratio distribution model is distributed. The distribution model modification unit 441*c* performs assignment of one or more distribution models again, to the distribution of the color feature data determined to be the residue candidate, in the distribution range acquired by the high ratio distribution model acquiring unit 431*b*.

Next, operations of the image processing apparatus according to the fourth embodiment will be described. The operations of the image processing apparatus according to the fourth embodiment as a whole are similar to those illustrated in FIG. 22, FIG. 24, and FIG. 39, and detailed operations of step S241 illustrated in FIG. 24 and step S25 illustrated in FIG. 39 are different.

Figure 61:
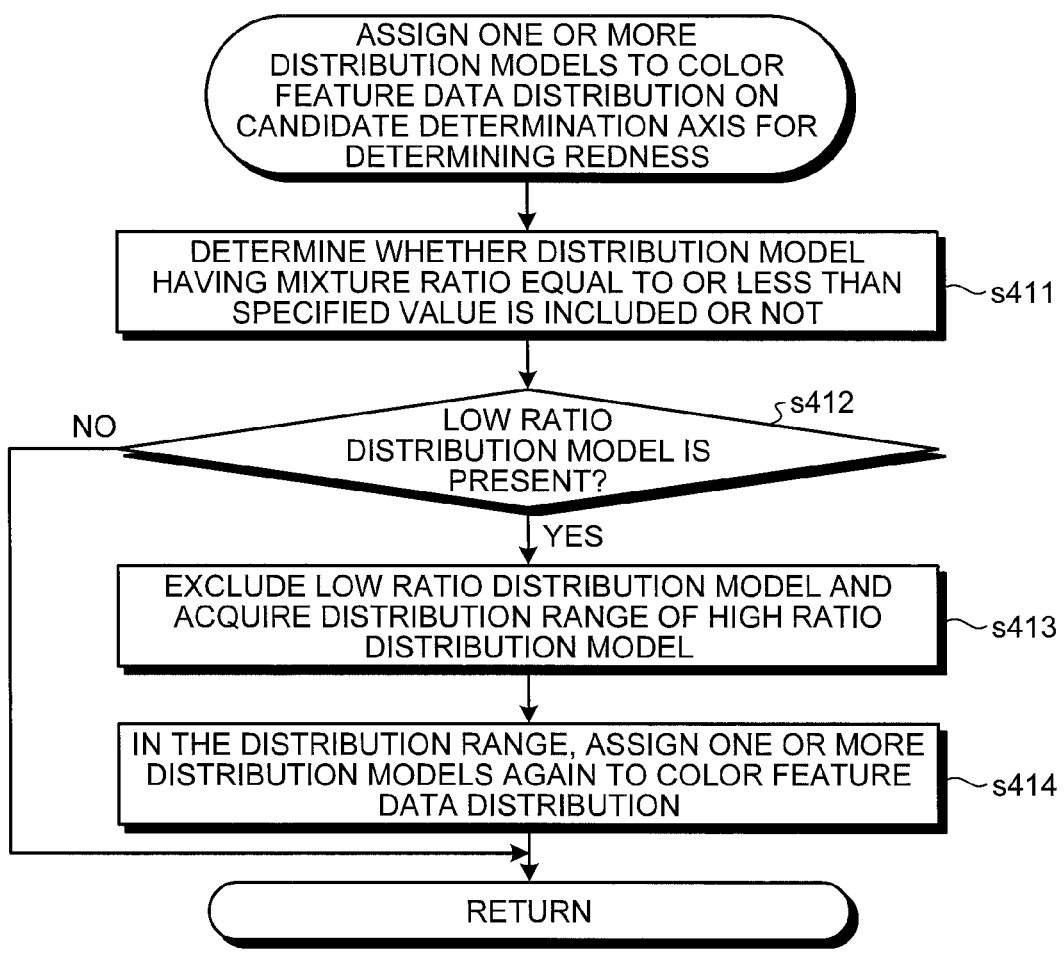
FIG. 61 is a flow chart illustration operations of the distribution model assignment unit that performs assignment of a distribution model to a distribution of color feature data in an intraluminal image.
Figure 62:
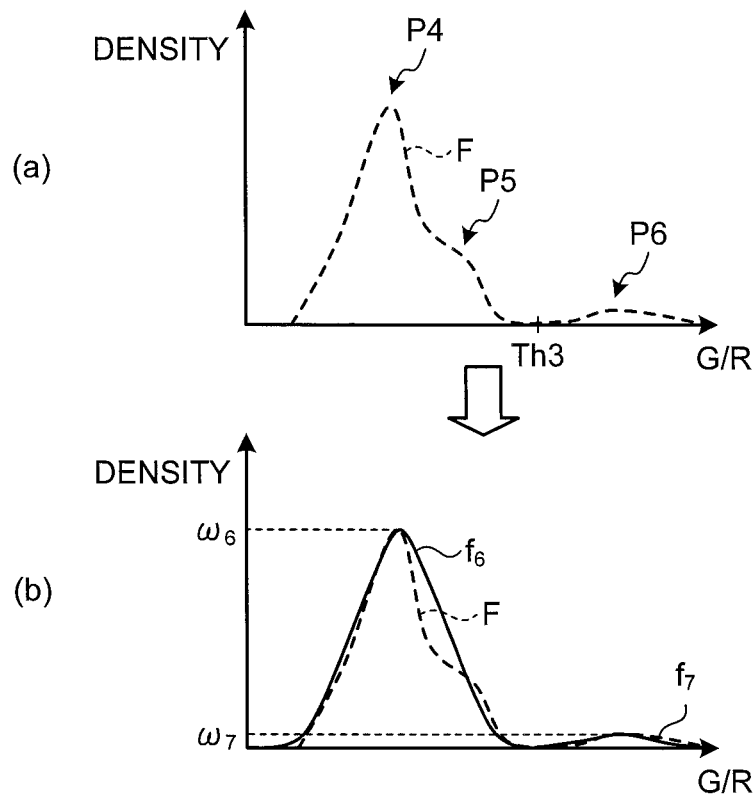
FIG. 62 is a schematic diagram illustrating the operations of the distribution model assignment unit illustrated in FIG. 60.
Figure 63:
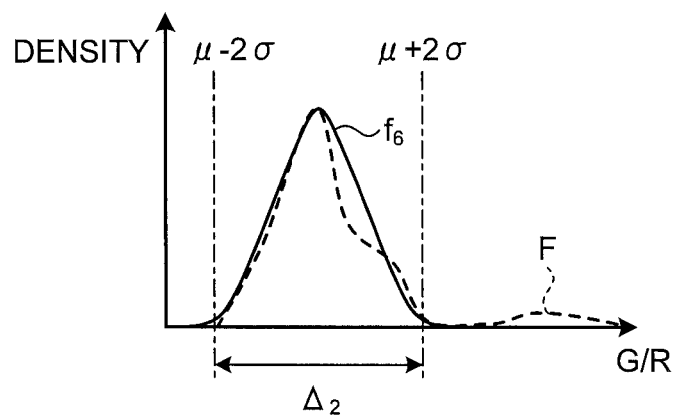
FIG. 63 is a schematic diagram illustrating the operations of the distribution model assignment unit illustrated in FIG. 60.
Figure 64:
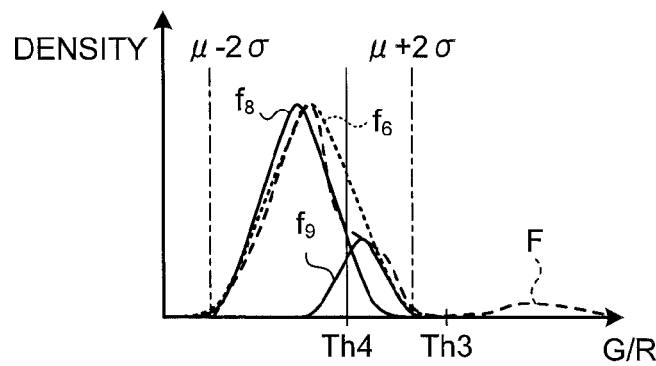
FIG. 64 is a schematic diagram illustrating the operations of the distribution model assignment unit illustrated in FIG. 60.

FIG. 61 is a flow chart illustrating operations of the distribution model assignment unit 431 that performs assignment of a distribution model to the distribution of the color feature data in the intraluminal image at step S241 illustrated in FIG. 24. Further, FIG. 62 to FIG. 64 are schematic diagrams illustrating the operations of the distribution model assignment unit 431.

First, at step s411, the low ratio distribution model determination unit 431*a* assigns, on the candidate determination axis (G/R axis), one or more distribution models to the distribution of the color feature data, and determines whether or not a low ratio distribution model having a mixing ratio equal to or less than the specified value is included in the assigned distribution model/models. For example, mixing ratios of two normal distributions $f_6$ and $f_7$ when the normal distributions $f_6$ and $f_7$ are assigned to a density function "F" corresponding to the distribution of the color feature data (see FIG. 62(*a*)), are denoted as $\omega_6$ and $\omega_7$ respectively (see FIG. 62(*b*)). The assignment of the normal distributions $f_6$ and $f_7$ may be performed by using the EM algorithm described in the second embodiment, for example.

The low ratio distribution model determination unit 431*a* determines, based on the mixing ratios $\omega_6$ and $\omega_7$, whether or not the normal distributions $f_6$ and $f_7$ are low ratio distribution models. For example, in FIG. 62(*b*), if the mixing ratio $\omega_7$ is equal to or less than a specified value, the normal distribution $f_7$ is determined to be a low ratio distribution model.

If a low ratio distribution model is included (step s412: Yes), the high ratio distribution model acquiring unit 441*b* excludes the low ratio distribution model from the distribution model assigned to the distribution of the color feature data and acquires a distribution range over which the rest of the distribution model (high ratio distribution model) is distributed (step s413). For example, if the normal distribution $f_7$ is the low ratio distribution model, the high ratio distribution model acquiring unit 431*b* acquires, as illustrated in FIG. 63, an average $\mu$ and a variance $\sigma^2$, which are parameters of the remaining normal distribution $f_6$ and takes a range $\mu \pm 2\sigma$ including 95.45% of the color feature data as a distribution range $\Delta_2$.

Subsequently, at step s414, the distribution model modification unit 431*c* assigns again, in the distribution range of the high ratio distribution model, one or more distribution models to the distribution of the color feature data. Specifically, as illustrated in FIG. 64, to a distribution of color feature data in the distribution range $\Delta_2$, two normal distributions $f_8$ and $f_9$ are assigned by an EM algorithm, for example. Thereafter, the operations return to the main routine.

At step s412, if a low ratio distribution model is not included (step s412: No), the operations return directly to the main routine.

Figure 65:
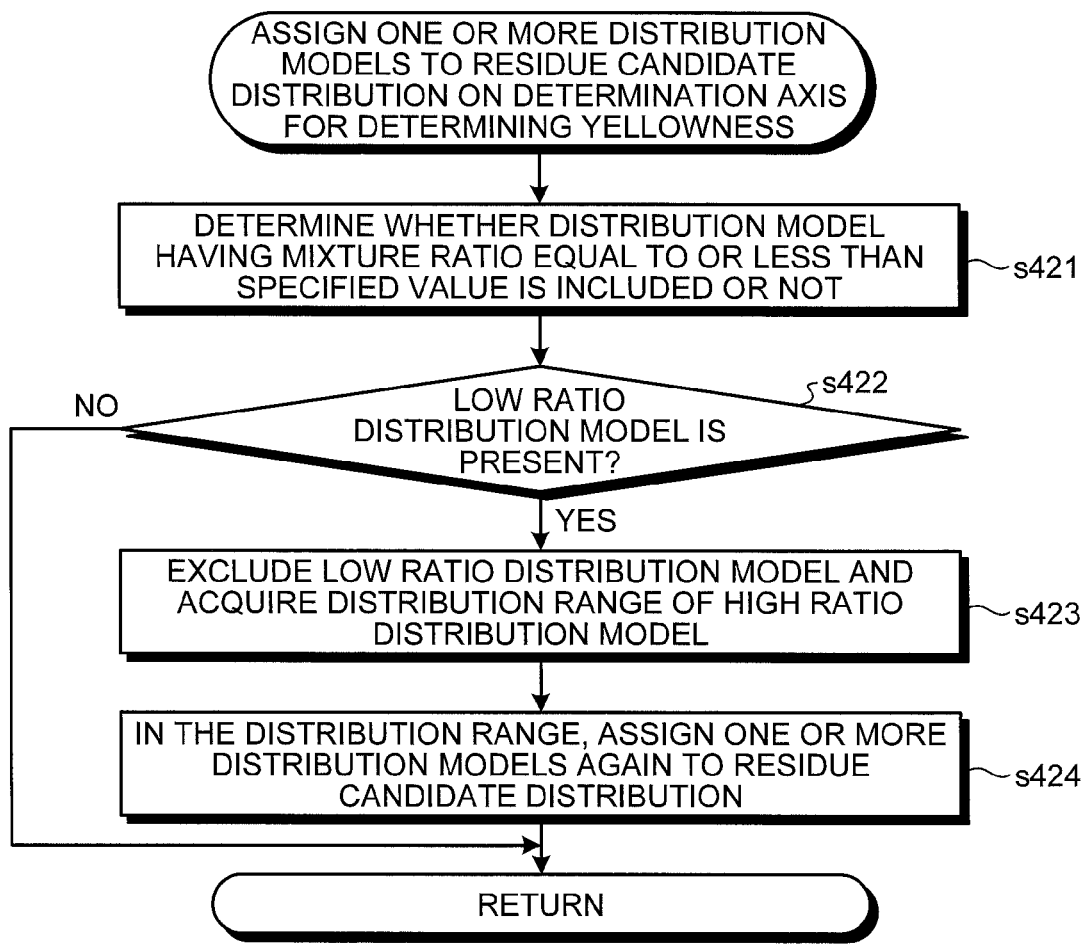
FIG. 65 is a flow chart illustrating the operations of the distribution model assignment unit that performs assignment of a distribution model to a distribution of color feature data determined to be a residue candidate.

FIG. 65 is a flow chart illustrating operations of the distribution model assignment unit 441 that performs assignment of a distribution model to the distribution of the color feature data determined to be a residue candidate at step S251 illustrated in FIG. 39. Hereinafter, while assuming the candidate determination axis (G/R axis) illustrated in FIG. 62 to FIG. 64 to be replaced by a determination axis (B/G axis), description is made with reference to these drawings.

First, at step s421, the low ratio distribution model determination unit 441*a* assigns, on the determination axis (B/G axis), one or more distribution models to the distribution of the color feature data determined to be the residue candidate, and determines whether or not a low ratio distribution model having a mixing ratio equal to or less than a specified value is included in the assigned distribution model/models (see FIG. 62).

If a low ratio distribution model is included (step s422: Yes), the high ratio distribution model acquiring unit 441*b* excludes the low ratio distribution model from the distribution model/models assigned to the distribution of the color feature data, and acquires a distribution range over which the rest of the distribution model/models (high ratio distribution model/models) is distributed (step s423). For example, if the normal distribution $f_7$ is a low ratio distribution model, as illustrated in FIG. 63, the high ratio distribution model acquiring unit 441*b* takes a range $\mu \pm 2\sigma$ of the remaining normal distribution $f_6$ that is the high ratio distribution model as the distribution range $\Delta_2$.

Subsequently, at step s424, the distribution model modification unit 441*c* assigns again, in the distribution range of the high ratio distribution model, one or more distribution models to the distribution of the color feature data determined to be the residue candidate (see FIG. 64). Thereafter, the operations return to the main routine.

At step s422, if a low ratio distribution model is not included (step s422: No), the operations return directly to the main routine.

According to the above described fourth embodiment, even if a low peak is present in a distribution of color feature data, a distribution model is appropriately assignable. Therefore, accurate identification of a residue region becomes possible.

As illustrated in FIG. 62(a) for example, if two normal distributions are attempted to be assigned to a density function in which three peaks P4 to P6 are present, as illustrated in FIG. 62(b), influenced by the peak P6, the normal distribution $f_7$ of a low ratio is generated, and a boundary Th3 is set between the normal distributions $f_6$ and $f_7$. If a process of setting a candidate threshold value (or threshold value) at a later stage is performed based on this boundary Th3, in a determination process of a residue region, a result not reflecting at all a distribution of color feature data represented by the peak P5 is obtained.

Accordingly, in the fourth embodiment, being limited to the distribution range $\Delta_2$ of the distribution model remaining after excluding the low ratio distribution model, assignment of the two normal distributions $f_6'$ and $f_7'$ is performed again. Thereby, a boundary Th4 that matches more to the actual distribution of the color feature data is obtainable, and an appropriate candidate threshold value (or threshold value) is settable.

The image processing apparatuses according to the above described first to fourth embodiments and the modified examples thereof may be realized by executing an image processing program recorded on a recording medium by a computer system such as a personal computer or a work station. Further, such a computer system may be used by being connected to an apparatus such as another computer system or a server, via a local area network, a wide area network (LAN/WAN), or a public line such as the Internet. In that case, the image processing apparatuses according to the embodiments and the modified examples may acquire image data of intraluminal images via these networks, output image processing results to various output devices (a viewer, a printer, and the like) connected via these networks, or store the image processing results in storage devices (a recording medium, a reading device therefor, and the like) connected via these networks.

The present invention is not limited to the first to fourth embodiments and the modified examples thereof, and by combining as appropriate the plural structural elements disclosed in the embodiments and the respective modified examples, formation of various inventions is possible. For example, formation by excluding some of the structural elements from the whole structural elements illustrated in the respective embodiments and modified examples may be made, or formation by combining as appropriate the structural elements illustrated in the different embodiments and modified examples may be made.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for distinguishing, from an intraluminal image obtained by imaging inside of a lumen of a subject, a residue region where a residue is photographed, the image processing apparatus comprising:
    a color feature data calculation unit configured to calculate color feature data of each pixel in the intraluminal image or color feature data of each small region obtained by dividing the intraluminal image into a plurality of small regions;
    a residue candidate distribution determination unit configured to determine, from among the color feature data, color feature data distributed on a side comparatively strong in redness to be a mucosa distribution and determine color feature data distributed on a side comparatively weak in redness to be a residue candidate distribution; and
    a residue distribution determination unit configured to determine, from among distributions of the color feature data determined to be the residue candidate distribution, a residue candidate distribution distributed on a side strong in yellowness with reference to the mucosa distribution to be a residue distribution.

2. The image processing apparatus according to claim 1, wherein the candidate distribution determination unit includes:
    a candidate determination axis setting unit configured to set, as a candidate determination axis to be used in distinguishing between the mucosa distribution and the residue candidate distribution, an axis corresponding to color feature data that change at least in strength of redness;
    a first histogram generation unit configured to generate, with respect to the candidate determination axis, a frequency distribution of the color feature data that the each pixel or small region has;
    a first determination threshold value setting unit configured to set, on the candidate determination axis, a determination threshold value for determining a range of color feature data corresponding to the mucosa distribution; and
    a candidate determination unit configured to distinguish between the mucosa distribution and the residue candidate distribution, based on the frequency distribution and the determination threshold value.

3. The image processing apparatus according to claim 1, wherein the residue distribution determination unit includes:
    a determination axis setting unit configured to set, as a determination axis to be used in determining whether or not the residue candidate distribution corresponds to the residue distribution, an axis corresponding to color feature data that change at least in strength of yellowness;
    a second histogram generation unit configured to generate, with respect to the determination axis, a frequency distribution of color feature data in the residue candidate distribution;
    a second determination threshold value setting unit configured to set a determination threshold value, based on the frequency distribution and a representative value of the mucosa distribution; and
    a determination unit configured to determine a residue candidate distribution present on a side stronger in yellowness than the determination threshold value, to be a residue distribution.

4. The image processing apparatus according to claim 1, further comprising a color feature data calculation unit configured to calculate color feature data in units of small regions obtained by dividing the intraluminal image based on edges of luminance components of the intraluminal image.

5. The image processing apparatus according to claim 2, wherein
    the intraluminal image has each of "R", "G", and "B" color components at each pixel position, and
    the candidate determination axis corresponds to G/R values.

6. The image processing apparatus according to claim 2, wherein the first histogram generation unit includes an unnecessary region exclusion unit configured to detect at least one of a bubble region, a dark region, and a red lesion region from the intraluminal image, and to determine and exclude the detected region as a region unnecessary in distinguishing between the mucosa distribution and the residue candidate distribution.

7. The image processing apparatus according to claim 2, wherein the first determination threshold value setting unit generates a frequency distribution of a mucosa obtained by accumulating, with respect to the candidate determination axis, color feature data in mucosa regions acquired from a plurality of intraluminal images beforehand, and holds, as the determination threshold value, color feature data where a frequency first becomes minimum or locally minimum when in the frequency distribution of the mucosa, a side weak in redness is seen from color feature data where a frequency is maximum.

8. The image processing apparatus according to claim 2, wherein the first determination threshold value setting unit evaluates a bimodal shape of the frequency distribution, calculates a boundary position in the frequency distribution based on a result of the evaluation, and sets the boundary position as the determination threshold value.

9. The image processing apparatus according to claim 2, wherein the first determination threshold value setting unit includes a composite histogram generation unit configured to divide the intraluminal image into a plurality of rectangular regions each having a specified size, generate a frequency distribution of the color feature data for each of the plurality of rectangular regions, and extract and combine maximum values or mode values of frequencies of the color feature data among the plurality of rectangular regions.

10. The image processing apparatus according to claim 1, wherein
the intraluminal image has each of "R", "G", and "B"color components at each pixel position, and
the candidate determination unit performs clustering on the distribution of the color feature data in a color feature data space having G/R values as one of components, compares a representative value of the G/R values in each cluster obtained by the clustering with the determination threshold value, and performs determination for each cluster.

11. The image processing apparatus according to claim 3, wherein
the intraluminal image has each of "R", "G", and "B" color components at each pixel position, and
the determination axis corresponds to B/G values.

12. The image processing apparatus according to claim 3, wherein the second determination threshold value setting unit approximates the frequency distribution of the color feature data by one normal distribution or two normal distributions, and sets the determination threshold value based on a representative value of the one normal distribution or a boundary position between the two normal distributions, and the representative value of the mucosa distribution.

13. The image processing apparatus according to claim 3, wherein
the intraluminal image has each of "R", "G", and "B" color components at each pixel position, and
the determination unit performs clustering on the distribution of the color feature data in a color feature data space having B/G values as one of components, compares a representative value of the B/G values in each cluster obtained by the clustering with a representative value of the B/G values in the mucosa distribution, and performs determination for each cluster.

14. An image processing method of distinguishing, from an intraluminal image obtained by imaging inside of a lumen of a subject, a residue region where a residue is photographed, the image processing method comprising:
calculating color feature data of each pixel in the intraluminal image or color feature data of each small region obtained by dividing the intraluminal image into a plurality of small regions;
determining, from among the color feature data, color feature data distributed on a side comparatively strong in redness to be a mucosa distribution and determining color feature data distributed on a side comparatively weak in redness to be a residue candidate distribution; and
determining, from the residue candidate distribution, a residue candidate distribution distributed on a side strong in yellowness with reference to the mucosa distribution to be a residue distribution.

15. A computer-readable recording device with an executable program stored thereon, wherein the program instructs a processor for distinguishing, from an intraluminal image obtained by imaging inside of a lumen of a subject, a residue region where a residue is photographed, to execute:
calculating color feature data of each pixel in the intraluminal image or color feature data of each small region obtained by dividing the intraluminal image into a plurality of small regions;
determining, from among the color feature data, color feature data distributed on a side comparatively strong in redness to be a mucosa distribution and determining color feature data distributed on a side comparatively weak in redness to be a residue candidate distribution; and
determining, from the residue candidate distribution, a residue candidate distribution distributed on a side strong in yellowness with reference to the mucosa distribution to be a residue distribution.

16. An image processing apparatus for distinguishing, from an intraluminal image obtained by imaging inside of a lumen of a subject, a residue region where a residue is photographed, the image processing apparatus comprising:
a color feature data calculation unit configured to calculate color feature data of each pixel in the intraluminal image or color feature data of each small region obtained by dividing the intraluminal image into a plurality of small regions;
a residue candidate distribution determination unit configured to assign, on a first determination axis of color feature data for determining redness, one or more distribution models to a distribution of the color feature data, and determine, based on redness of the one or more distribution models, color feature data representing a residue candidate; and
a residue distribution determination unit configured to assign, on a second determination axis of color feature data for determining yellowness, one or more distribution models to the color feature data determined to represent the residue candidate by the residue candidate distribution determination unit and determine, based on yellowness of the one or more distribution models, color feature data representing a residue.

17. The image processing apparatus according to claim 16, wherein the residue distribution determination unit includes:
a distribution model assignment unit configured to generate one or more distribution models by assigning a specified distribution model to the distribution of the color feature data determined to represent the residue candidate, on the second determination axis;
a distribution model determination unit configured to determine whether or not each of the one or more distribution models is a residue distribution by comparing the one or more distribution models with a specified threshold value;
a threshold value setting unit configured to set, based on a result of the determination by the distribution model determination unit, a threshold value for determining color feature data representing a residue; and
a determination unit configured to determine the color feature data representing a residue from among the color feature data determined to be the residue candidate, based on the threshold value set by the threshold value setting unit.

18. The image processing apparatus according to claim 16, further comprising an unnecessary region exclusion unit configured to exclude a region unnecessary for determination of the residue from the intraluminal image.

19. The image processing apparatus according to claim 16, wherein the residue candidate distribution determination unit includes:
a distribution model assignment unit configured to generate one or more distribution models by assigning a specified distribution model to the distribution of the color feature data on the first determination axis;
a distribution model determination unit configured to determine whether or not each of the one or more distribution models is a residue candidate distribution by comparing the one or more distribution models with a specified threshold value;
a candidate threshold value setting unit configured to set, based on a result of the determination by the distribution model determination unit, a candidate threshold value for determining color feature data representing a residue candidate; and
a candidate determination unit configured to determine, based on the candidate threshold value, the color feature data representing a residue candidate from among the color feature data in the intraluminal image.

20. The image processing apparatus according to claim 19, wherein the distribution model assignment unit includes:
a brief distribution model assignment unit configured to assign to the distribution of the color feature data, a distribution model or models fewer than distribution models assignable to the distribution of the color feature data, as a brief distribution model or models;
a brief distribution model range acquiring unit configured to acquire a distribution range of the brief distribution model or models on the first determination axis; and
a distribution model modification unit configured to assign one or more distribution models to the distribution of the color feature data in the distribution range.

21. The image processing apparatus according to claim 19, wherein the distribution model assignment unit includes:
a low ratio distribution model determination unit configured to determine whether or not a low ratio distribution model having a mixing ratio among the one or more distribution models equal to or less than a specified value is included in the one or more distribution models;
a high ratio distribution model range acquiring unit configured to acquire, if the low ratio distribution model is included in the one or more distribution models, a distribution range over which a distribution model remaining after excluding the low ratio distribution model from the one or more distribution models is distributed on the first determination axis; and
a distribution model modification unit configured to assign again one or more distribution models to the distribution of the color feature data in the distribution range.

22. The image processing apparatus according to claim 19, wherein the distribution model determination unit includes:
a representative value calculation unit configured to calculate a representative value of the one or more distribution models on the first determination axis; and
a threshold value processing unit configured to determine, based on a threshold value set beforehand corresponding to the representative value on the first determination axis, a distribution model distributed on a side weak in redness to be the residue candidate distribution.

23. The image processing apparatus according to claim 19, wherein the candidate threshold value setting unit includes:
an inter-distribution-model candidate threshold value setting unit configured to set, if a plurality of distribution models are assigned to the distribution of the color feature data by the distribution model assignment unit and determination resulting differently from one another among the plurality of distribution models is made by the distribution model determination unit, a value among the plurality of distribution models on the first determination axis as the candidate threshold value; and
an out-of-distribution-model candidate threshold value setting unit configured to set, if a plurality of distribution models are assigned to the distribution of the color feature data by the distribution model assignment unit and determination resulting identically to one another among the plurality of distribution models is made by the distribution model determination unit, or if one distribution model is assigned to the distribution of the color feature data by the distribution model assignment unit, a value outside the one or more distribution models on the first determination axis as the candidate threshold value.

24. The image processing apparatus according to claim 19, wherein the candidate determination unit performs determination on each of clusters obtained by clustering the distribution of the color feature data, by using a representative value of each of the clusters.

25. The image processing apparatus according to claim 17, wherein the distribution model assignment unit includes:
a brief distribution model assignment unit configured to assign to the distribution of the color feature data, a distribution model or models fewer than distribution models assignable to the distribution of the color feature data, as a brief distribution model or models;
a brief cluster range acquiring unit configured to acquire a distribution range of the brief distribution model or models on the second determination axis; and
a distribution model modification unit configured to assign one or more distribution models to the distribution of the color feature data in the distribution range.

26. The image processing apparatus according to claim 17, wherein the distribution model assignment unit includes:
a low ratio distribution model determination unit configured to determine whether or not a low ratio distribution model having a mixing ratio among the one or more distribution models equal to or less than a specified value is included in the one or more distribution models;
a high ratio distribution model range acquiring unit configured to acquire, if the low ratio distribution model is included in the one or more distribution models, a distribution range over which a distribution model remaining after excluding the low ratio distribution model from the one or more distribution models is distributed on the second determination axis; and a distribution model modification unit configured to assign again one or more distribution models to the distribution of the color feature data determined to be the residue candidate, in the distribution range.

27. The image processing apparatus according to claim 17, wherein the distribution model determination unit includes:

a representative value calculation unit configured to calculate a representative value of the one or more distribution models on the second determination axis; and a threshold value processing unit configured to determine, based on a threshold value set beforehand corresponding to the representative value on the second determination axis, a distribution model distributed on a side strong in yellowness to be the residue distribution.

28. The image processing apparatus according to claim 27, wherein the threshold value processing unit includes a mucosa reference threshold value setting unit configured to treat a distribution of color feature data not determined to be the residue candidate by the residue candidate distribution determination unit, from among the one or more distribution models, as a mucosa distribution, and calculate a representative value of the mucosa distribution on the second determination axis.

29. The image processing apparatus according to claim 27, wherein the threshold value processing unit includes:

an inter-distribution-model threshold value setting unit configured to set, if a plurality of distribution models are assigned to the distribution of the color feature data by the distribution model assignment unit and determination resulting differently from one another among the plurality of distribution models is made by the distribution model determination unit, a value among the plurality of distribution models on the second determination axis as the threshold value; and an out-of-distribution-model threshold value setting unit configured to set, if a plurality of distribution models are assigned to the distribution of the color feature data by the distribution model assignment unit and determination resulting identically to one another among the plurality of distribution models is made by the distribution model determination unit, or if one distribution model is assigned to the distribution of the color feature data by the distribution model assignment unit, a value outside the one or more distribution models on the second determination axis as the threshold value.

30. The image processing apparatus according to claim 17, wherein the determination unit performs determination on each of clusters obtained by clustering the distribution of the color feature data, by using a representative value of each of the clusters.

31. An image processing method of distinguishing, from an intraluminal image obtained by imaging inside of a lumen of a subject, a residue region where a residue is photographed, the image processing method comprising:

calculating color feature data of each pixel in the intraluminal image or color feature data of each small region obtained by dividing the intraluminal image into a plurality of small regions;

assigning, on a first determination axis of color feature data for determining redness, one or more distribution models to a distribution of the color feature data and determining, based on redness of the one or more distribution models, color feature data representing a residue candidate; and assigning, on a second determination axis of color feature data for determining yellowness, one or more distribution models to the color feature data determined to represent the residue candidate, and determining, based on yellowness of the one or more distribution models, color feature data representing a residue.

32. A computer-readable recording device with an executable program stored thereon, wherein the program instructs a processor for distinguishing, from an intraluminal image obtained by imaging inside of a lumen of a subject, a residue region where a residue is photographed, to execute:

calculating color feature data of each pixel in the intraluminal image or color feature data of each small region obtained by dividing the intraluminal image into a plurality of small regions;

assigning, on a first determination axis of color feature data for determining redness, one or more distribution models to a distribution of the color feature data and determining, based on redness of the one or more distribution models, color feature data representing a residue candidate; and assigning, on a second determination axis of color feature data for determining yellowness, one or more distribution models to the color feature data determined to represent the residue candidate, and determining, based on yellowness of the one or more distribution models, color feature data representing a residue.

* * * * *